United States Patent

Johnson

(10) Patent No.: US 8,124,607 B2
(45) Date of Patent: Feb. 28, 2012

(54) POLY AROMATIC PYRAZINOYLGUANIDINE SODIUM CHANNEL BLOCKERS

(75) Inventor: Michael Ross Johnson, Chapel Hill, NC (US)

(73) Assignee: Parion Sciences, Inc., Durham, NC (US)

(*) Notice: Subject to any disclaimer, the term of this patent is extended or adjusted under 35 U.S.C. 154(b) by 0 days.

(21) Appl. No.: 12/393,252

(22) Filed: Feb. 26, 2009

(65) Prior Publication Data

US 2009/0214444 A1 Aug. 27, 2009

Related U.S. Application Data

(60) Provisional application No. 61/031,466, filed on Feb. 26, 2008.

(51) Int. Cl.
A61K 31/4965 (2006.01)
(52) U.S. Cl. .................... 514/255.06; 544/409
(58) Field of Classification Search .......... 514/255.06; 544/409
See application file for complete search history.

(56) References Cited

U.S. PATENT DOCUMENTS

| | | | |
|---|---|---|---|
| 3,313,813 A | 4/1967 | Cragoe, Jr. et al. | |
| 4,604,394 A | 8/1986 | Kaczorowski et al. | |
| 4,894,376 A | 1/1990 | Morad et al. | |
| 6,858,614 B2 | 2/2005 | Johnson | |
| 6,858,615 B2 | 2/2005 | Johnson | |
| 6,903,105 B2 | 6/2005 | Johnson | |
| 6,995,160 B2 | 2/2006 | Johnson | |
| 7,026,325 B2 | 4/2006 | Johnson | |
| 7,030,117 B2 | 4/2006 | Johnson | |
| 7,064,129 B2 | 6/2006 | Johnson et al. | |
| 7,186,833 B2 | 3/2007 | Johnson | |
| 7,189,719 B2 | 3/2007 | Johnson | |
| 7,192,958 B2 | 3/2007 | Johnson | |
| 7,192,959 B2 | 3/2007 | Johnson | |
| 7,192,960 B2 | 3/2007 | Johnson | |
| 7,241,766 B2 | 7/2007 | Johnson | |
| 7,247,636 B2 | 7/2007 | Johnson | |
| 7,247,637 B2 | 7/2007 | Johnson et al. | |
| 7,317,013 B2 | 1/2008 | Johnson | |
| 7,332,496 B2 | 2/2008 | Johnson | |
| 7,345,044 B2 | 3/2008 | Johnson | |
| 7,368,447 B2 | 5/2008 | Johnson et al. | |
| 7,368,450 B2 | 5/2008 | Johnson | |
| 7,368,451 B2 | 5/2008 | Johnson et al. | |
| 7,375,107 B2 | 5/2008 | Johnson | |
| 7,388,013 B2 | 6/2008 | Johnson et al. | |
| 7,399,766 B2 | 7/2008 | Johnson | |
| 7,410,968 B2 | 8/2008 | Johnson et al. | |
| 2004/0116415 A1 | 6/2004 | Sun et al. | |
| 2004/0195160 A1 | 10/2004 | Max et al. | |
| 2004/0198744 A1 | 10/2004 | Johnson | |
| 2004/0198745 A1 | 10/2004 | Johnson | |
| 2004/0198746 A1 | 10/2004 | Johnson | |
| 2004/0198747 A1 | 10/2004 | Johnson | |
| 2004/0198748 A1 | 10/2004 | Johnson | |
| 2004/0198749 A1 | 10/2004 | Johnson | |
| 2004/0199456 A1 | 10/2004 | Flint et al. | |
| 2004/0204424 A1 | 10/2004 | Johnson | |
| 2004/0204425 A1 | 10/2004 | Johnson | |
| 2004/0229884 A1 | 11/2004 | Johnson | |
| 2005/0059676 A1 | 3/2005 | Johnson | |
| 2005/0080092 A1 | 4/2005 | Johnson et al. | |
| 2005/0080093 A1 | 4/2005 | Johnson et al. | |
| 2005/0090505 A1 | 4/2005 | Johnson et al. | |
| 2005/0113388 A1 | 5/2005 | Johnson | |
| 2005/0113389 A1 | 5/2005 | Johnson | |
| 2005/0113390 A1 | 5/2005 | Johnson | |
| 2006/0142306 A1 | 6/2006 | Johnson | |
| 2006/0142581 A1 | 6/2006 | Johnson | |
| 2007/0032509 A1 | 2/2007 | Johnson et al. | |
| 2007/0265280 A1 | 11/2007 | Johnson | |
| 2008/0076782 A1 | 3/2008 | Johnson | |
| 2008/0090841 A1 | 4/2008 | Johnson et al. | |
| 2008/0096896 A1 | 4/2008 | Johnson | |
| 2008/0103148 A1 | 5/2008 | Johnson | |
| 2008/0167466 A1 | 7/2008 | Johnson et al. | |
| 2008/0171879 A1 | 7/2008 | Johnson | |
| 2008/0171880 A1 | 7/2008 | Johnson et al. | |
| 2008/0176863 A1 | 7/2008 | Johnson et al. | |
| 2008/0177072 A1 | 7/2008 | Johnson | |
| 2008/0200476 A1 | 8/2008 | Johnson | |
| 2008/0249109 A1 | 10/2008 | Johnson et al. | |
| 2008/0293740 A1 | 11/2008 | Johnson et al. | |

(Continued)

FOREIGN PATENT DOCUMENTS

WO    WO 03/070182    8/2003

(Continued)

OTHER PUBLICATIONS

Jordan, V. C. Nature Reviews: Drug Discovery, 2, 2003, 205.*

(Continued)

*Primary Examiner* — James O Wilson
*Assistant Examiner* — Douglas M Willis
(74) *Attorney, Agent, or Firm* — Oblon, Spivak, McClelland, Maier & Neustadt, L.L.P.

(57) ABSTRACT

Polyaromatic sodium channel blockers represented by the formula:

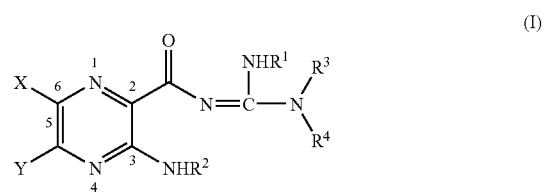

(I)

are provided where the structural variables are defined herein. The invention also includes a variety of compositions, combinations and methods of treatment using these inventive sodium channel blockers.

39 Claims, No Drawings

U.S. PATENT DOCUMENTS

| | | |
|---|---|---|
| 2009/0018144 A1 | 1/2009 | Johnson et al. |
| 2009/0062308 A1 | 3/2009 | Johnson |
| 2009/0076273 A1 | 3/2009 | Johnson |
| 2009/0082287 A1 | 3/2009 | Johnson et al. |

FOREIGN PATENT DOCUMENTS

| | | | |
|---|---|---|---|
| WO | WO 2005/018644 | | 3/2005 |
| WO | WO 2007/018640 A1 | | 2/2007 |
| WO | WO 2007/071396 | | 6/2007 |
| WO | WO 2007/071400 | * | 6/2007 |
| WO | WO 2008/135557 | | 11/2008 |
| WO | WO 2009/074575 | | 6/2009 |
| WO | WO 2009/138378 | | 11/2009 |
| WO | WO 2009/150137 | | 12/2009 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
U.S. Appl. No. 10/920,527, filed Aug. 18, 2004, Hopkins.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 11/696,003, filed Apr. 3, 2007, Johnson.
U.S. Appl. No. 11/573,413, filed Feb. 8, 2007, Johnson.
U.S. Appl. No. 11/573,421, filed Feb. 8, 2007, Johnson.
U.S. Appl. No. 60/909,818, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al.
U.S. Appl. No. 11/835,902, filed Aug. 8, 2007, Johnson, et al.
U.S. Appl. No. 61/030,313, filed Feb. 21, 2008, Johnson.
U.S. Appl. No. 61/031,466, filed Feb. 26, 2008, Johnson.
U.S. Appl. No. 12/171,867, filed Jul. 11, 2008, Johnson, et al.
U.S. Appl. No. 12/171,897, filed Jul. 11, 2008, Johnson, et al.
U.S. Appl. No. 61/079,989, filed Jul. 11, 2008, Boucher, et al.
U.S. Appl. No. 12/179,353, filed Jul. 24, 2008, Johnson.
U.S. Appl. No. 12/249,175, filed Oct. 10, 2008, Boucher, et al.
U.S. Appl. No. 12/304,006, filed Dec. 9, 2008, Johnson, et al.
U.S. Appl. No. 12/304,042, filed Dec. 9, 2008, Johnson.
U.S. Appl. No. 12/304,040, filed Dec. 9, 2008, Johnson.
U.S. Appl. No. 60/909,802, filed Apr. 3, 2007, Johnson, et al.
U.S. Appl. No. 12/501,654, filed Jul. 13, 2009, Boucher, et al.
U.S. Appl. No. 12/939,579, filed Nov. 4, 2010, Johnson, et al.
Extended European Search Report filed in Application No. 09747034.8 on Mar. 23, 2011.
European Communication filed in Application No. 09747034.8 on Apr. 11, 2011.

* cited by examiner

POLY AROMATIC PYRAZINOYLGUANIDINE SODIUM CHANNEL BLOCKERS

CONTINUING APPLICATION DATA

This application claims priority to U.S. provisional application Ser. No. 61/031,466 filed on Feb. 26, 2008, and incorporated herein by reference.

BACKGROUND OF THE INVENTION

1. Field of the Invention

The present invention relates to sodium channel blockers. The present invention also includes a variety of methods of treatment using these inventive sodium channel blockers.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic obstructive pulmonary diseases are characterized by dehydration of airway surfaces and the retention of mucous secretions in the lungs. Examples of such diseases include cystic fibrosis, chronic bronchitis, and primary or secondary ciliary dyskinesia. Such diseases affect approximately 15 million patients in the United States, and are the sixth leading cause of death. Other airway or pulmonary diseases characterized by the accumulation of retained mucous secretions include sinusitis (an inflammation of the paranasal sinuses associated with upper respiratory infection) and pneumonia.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

R. C. Boucher, in U.S. Pat. No. 6,926,911, suggests the use of the relatively impotent sodium channel blockers such as amiloride, with osmolytes for the treatment of airway diseases. This combination gives no practical advantage over either treatment alone and is clinically not useful, see Donaldson et al, N Eng J. Med., 2006; 353:241-250. Amiloride was found to block the water permeability of airways and negate the potential benefit of concurrent use of hypertonic saline and amiloride.

U.S. Pat. No. 5,817,028 to Anderson describes a method for the provocation of air passage narrowing (for evaluating susceptibility to asthma) and/or the induction of sputum in subjects via the inhalation of mannitol. It is suggested that the same technique can be used to induce sputum and promote mucociliary clearance. Substances suggested include sodium chloride, potassium chloride, mannitol and dextrose.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete Cl– (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

Fifty million Americans and hundreds of millions of others around the world suffer from high blood pressure and the subsequent sequale leading to congestive heart failure and increasing mortality. It is the Western World's leading killer and there is a need there for new medicines to treat these diseases. Thus, in addition, some of the novel sodium channel blockers of this invention can be designed to target the kidney and as such they may be used as diuretics for the treatment of hypertension, congestive heart failure (CHF) and other cardiovascular diseases. These new agents may be used alone or in combination with beta-blockers, ACE inhibitors, HMG-CoA reductase inhibitors, calcium channel blockers and other cardiovascular agents.

SUMMARY OF THE INVENTION

It is an object of the present invention to provide compounds that are more potent and/or absorbed less rapidly from mucosal surfaces, and/or are less reversible as compared to known compounds.

It is another aspect of the present invention to provide compounds that are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds.

It is another object of the present invention to provide compounds which are (1) absorbed less rapidly from mucosal surfaces, especially airway surfaces, as compared to known compounds and; (2) when absorbed from mucosal surfaces after administration to the mucosal surfaces, are converted in vivo into metabolic derivatives thereof which have reduced efficacy in blocking sodium channels as compared to the administered parent compound. It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on mucosal surfaces as compared to previous compounds.

It is another object of the present invention to provide compounds that target the kidney for use in the treatment of cardiovascular disease.

It is another object of the present invention to provide methods of treatment that take advantage of the pharmacological properties of the compounds described above.

In particular, it is an object of the present invention to provide methods of treatment which rely on rehydration of mucosal surfaces.

In particular, it is an object of the present invention to provide methods of treating cardiovascular disease.

The objects of the present invention may be accomplished with a class of pyrazinoylguanidine represented by a compound of formula (I)

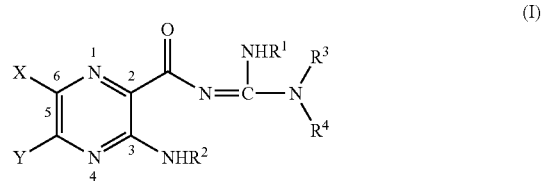

(I)

and includes racemates, enantiomers, diastereomers, tautomers, polymorphs, pseudopolymorphs and pharmaceutically acceptable salts, thereof, wherein:

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R^2)_2$;

$R^1$ is hydrogen or lower alkyl;

each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-(Z)_g-R^7$, $-(CH_2)_m-NR^{10}-CH_2(CHOR^8)(CHOR^8)_n-CH_2OR^8$, $-(CH_2)_n-CO_2R^7$, or

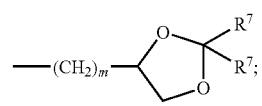

$R^3$ and $R^4$ are each, independently, hydrogen, lower alkyl, hydroxyl-lower alkyl, phenyl, (phenyl)-lower alkyl, (halophenyl)-lower alkyl, ((lower-alkyl)phenyl)-lower-alkyl, ((lower-alkoxy)phenyl))-lower alkyl, (naphthyl)-lower alkyl, or (pyridyl)-lower alkyl, or a group represented by formula A or formula B, with the proviso that at least one of $R^3$ and $R^4$ is a group represented by the formula A or formula B;

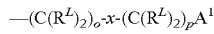  formula A

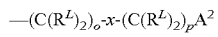  formula B $A^1$ is a $C_7$-$C_{15}$-membered aromatic carbocycle substituted with at least one $R^5$ and the remaining substituents are $R^6$;

$A^2$ is a seven to fifteen-membered aromatic heterocycle substituted with at least one $R^5$ and the remaining substituents are $R^6$ wherein said aromatic heterocycle comprises 1-4 heteroatoms selected from the group consisting of O, N, and S;

each $R^L$ is, independently, —$R^7$, —$(CH_2)_n$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_n$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

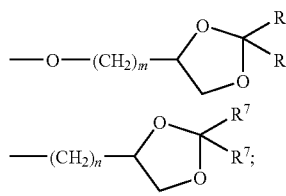

each o is, independently, an integer from 0 to 10;

each p is, independently, an integer from 0 to 10;

with the proviso that the sum of o and p in each contiguous chain is from 1 to 10;

each x is, independently, O, $NR^{10}$, C(=O), CHOH, C(=N—$R^{10}$), $CHNR^7R^{10}$, or a single bond;

each $R^5$ is, independently, OH, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—$C(=O)NR^7R^{10}$, —O—$(CH_2)_m$—$C(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

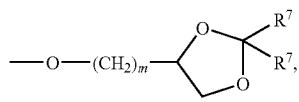

-continued

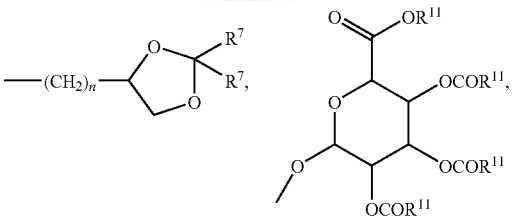

—$(CH_2)_n$—$CO_2R^{13}$, -Het-$(CH_2)_m$—$CO_2R^{13}$, —$(CH_2)_n$—$(Z)_g$—$CO_2R^{13}$, -Het-$(CH_2)_m$—$(Z)_g$—$CO_2R^{13}$, —$(CH_2)_n$—$NR^{10}$—$(CH_2)_m(CHOR^8)_n$—$CO_2R^{13}$, -Het-$(CH_2)_m$—$NR^{10}$—$(CH_2)_m(CHOR^8)_n$—$CO_2R^{13}$, —$(CH_2)_n$—$(CHOR^8)_m$—$CO_2R^{13}$, -Het-$(CH_2)_m$—$(CHOR^8)_m$—$CO_2R^{13}$, —$(CH_2)_n$—$(CHOR^8)_m(Z)_g$—$CO_2R^{13}$, -Het-$(CH_2)_n$—$(CHOR^8)_m$—$(Z)_g$—$CO_2R^{13}$, —$(CH_2)_n$—$(Z)_g$—$(CH_2)_m$—$CO_2R^{13}$, —$(CH_2)_n$—$(Z)_g$—$(CHOR^8)_m$—$(Z)_g$—$CO_2R^{13}$, -Het-$(CH_2)_n$—$(Z)_g$—$(CHOR^8)_m$—$(Z)_g$—$CO_2R^{13}$, —$(CH_2)_n$—$CONH$—$C(=NR^{13})$—$NR^{13}R^{13}$, -Het-$(CH_2)_n$—$CO$—$NH$—$C(=NR^{13})$—$NR^{13}R^{13}$, —$(CH_2)_n$—$(Z)_g$—$CONH$—$C(=NR^{13})$—$NR^{13}R^{13}$, -Het-$(CH_2)_n$—$(Z)_g$—$CONH$—$C(=NR^{13})$—$NR^{13}R^{13}$, —$(CH_2)_n$—$NR^{10}$—$(CH_2)_m(CHOR^8)_n$—$CONH$—$C(=NR^{13})$—$NR^{13}R^{13}$, -Het-$(CH_2)_n$—$NR^{10}$—$(CH_2)_m(CHOR^8)_n$—$CONH$—$C(=NR^{13})$—$NR^{13}R^{13}$, —$(CH_2)_n$—$(CHOR^8)_m$—$CONH$—$C(=NR^{13})$—$NR^{13}R^{13}$, -Het-$(CH_2)_n$—$(CHOR^8)_m$—$CONH$—$C(=NR^{13})$—$NR^{13}R^{13}$, —$(CH_2)_n$—$(CHOR^8)_m$—$(Z)_g$—$CONH$—$C(=NR^{13})$—$NR^{13}R^{13}$, -Het-$(CH_2)_n$—$(CHOR^8)_m$—$(Z)_g$—$CONH$—$C(=NR^{13})$—$NR^{13}R^{13}$, —$(CH_2)_n(Z)_g$—$(CH_2)_m$$CONH$—$C(=NR^{13})$—$NR^{13}R^{13}$, -Het-$(CH_2)_n$—$(Z)_g$—$(CH_2)_m$$CONH$—$C(=NR^{13})$—$NR^{13}R^{13}$, —$(CH_2)_n$—$(Z)_g$—$(CHOR^8)_m$—$(Z)_g$—$CONH$—$C(=NR^{13})$—$NR^{13}R^{13}$, Het-$(CH_2)_n$—$(Z)_g$—$(CHOR^8)_m$—$(Z)_g$—$CONH$—$C(=NR^{13})$—$NR^{13}R^{13}$, —$(CH_2)_n$—$CONR^7$—$CONR^{13}R^{13}$, -Het-$(CH_2)_n$—$CONR^7$—$CONR^{13}R^{13}$, —$(CH_2)_n$—$(Z)_g$—$CONR^7CONR^{13}R^{13}$, —$(CH_2)_n$—$(Z)_g$—$CONR^7$—$CONR^{13}R^{13}$, —$(CH_2)_n$—$NR^{10}$—$(CH_2)_m(CHOR^8)_m$—$CONR^7CONR^{13}R^{13}$, -Het-$(CH_2)_n$—$NR^{10}$—$(CH_2)_m$$(CHOR^8)_m$—$CONR^7$—$CONR^{13}R^{13}$, —$(CH_2)_n$—$(CHOR^8)_m$—$CONR^7$—$CONR^{13}R^{13}$, Het-$(CH_2)_n$—$(CHOR^8)_m$—$CONR^7$—$CONR^{13}R^{13}$, —$(CH_2)_n$—$(CHOR^8)_m$—$CONR^7$—$CONR^{13}R^{13}$, —$(CH_2)_n$—$(CHOR^8)_m$—$(Z)_g$—$CONR^7$—$CONR^{13}R^{13}$, -Het-$(CH_2)_n$—$(CHOR^8)_m$—$(Z)_g$—$CNR^7$—$CONR^{13}R^{13}$, —$(CH_2)_n$—$(Z)_g$—$(CH_2)_m$$CONR^7$—$CONR^{13}R^{13}$, -Het-$(CH_2)_n$—$(Z)_g$—$(CH_2)_m$ $CONR^7$—$CONR^{13}R^{13}$, —$(CH_2)_n$—$(Z)_g$—$(CHOR^8)_m$—$(Z)_g$—$CONR^7$—$CONR^{13}R^{13}$, -Het-$(CH_2)_n$—$(Z)_g$$(CHOR^8)_m$—$(Z)_g$—$CONR^7$—$CONR^{13}R^{13}$, —$(CH_2)_n$—$CONR^7SO_2NR^{13}R^{13}$, -Het-$(CH_2)_m$—$CONR^7SO_2$$NR^{13}R^{13}$, —$(CH_2)_n$—$(Z)_g$—$CONR^7SO_2NR^{13}R^{13}$, -Het-$(CH_2)_m$—$(Z)_g$—$CONR^7SO_2NR^{13}R^{13}$, —$(CH_2)_n$—$NR^{10}$—$(CH_2)_m(CHOR^8)_n$—$CONR^7SO_2NR^{13}R^{13}$, -Het-$(CH_2)_m$—$NR^{10}$—$(CH_2)_m(CHOR^8)_n$—$CONR^7SO_2NR^{13}R^{13}$, —$(CH_2)_n$—$(CHOR^8)_m$—$CONR^7SO_2NR^{13}R^{13}$, -Het-$(CH_2)_m$—$(CHOR^8)_m$—$CONR^7SO_2NR^{13}R^{13}$, —$(CH_2)_n$—$(CHOR^8)_m$—$(Z)_g$—$CONR^7SO_2NR^{13}R^{13}$, -Het-$(CH_2)_n$—$(CHOR^8)_m$—$(Z)_g$—$CONR^7SO_2NR^{13}R^{13}$, —$(CH_2)_n$—$(Z)_g$—$(CH_2)_m$ $CONR^7SO_2NR^{13}R^{13}$, -Het-$(CH_2)_n$—$(Z)_g$—$(CH_2)_m$$CONR^7SO_2NR^{13}R^{13}$, —$(CH_2)_n$—$(Z)_g$$(CHOR^8)_m$—$(Z)_g$—$CONR^7SO_2NR^{13}R^{13}$, -Het-$(CH_2)_n$—$(Z)_g$—$(CHOR^8)_m$—$(Z)_g$—$CONR^7SO_2NR^{13}R^{13}$, —$(CH_2)_9$—$SO_2NR^{13}R^{13}$, -Het-$(CH_2)_m$—$SO_2NR^{13}R^{13}$, —$(CH_2)_n$—N$(Z)_g$—$SO_2NR^{13}R^{13}$, -Het-$(CH_2)_m$—$(Z)_g$—$SO_2NR^{13}R^{13}$, —$(CH_2)_n$—$NR^{10}$—$(CH_2)_m$—$(CHOR^8)_n$—$SO_2NR^{13}R^{13}$, -Het-$(CH_2)$—$NR^{10}$—$(CH_2)_m(CHOR^8)_n$—$SO_2NR^{13}R^{13}$,

—(CH$_2$)$_n$—(CHOR$^8$)$_m$—SO$_2$NR$^{13}$R$^{13}$, -Het(CH$_2$)$_m$(CHOR$^8$)$_m$—SO$_2$NR$^{13}$R$^{13}$, —(CH$_2$)$_n$—(CHOR$^8$)$_m$—(Z)$_g$—SO$_2$NR$^{13}$R$^{13}$, -Het-(CH$_2$)$_n$—(CHOR$^8$)$_m$—(Z)$_g$—SO$_2$NR$^{13}$R$^{13}$, —(CH$_2$)$_n$—(Z)$_g$—(CH$_2$)$_m$SO$_2$NR$^{13}$R$^{13}$, -Het-(CH$_2$)$_n$—(Z)$_g$—(CH$_2$)$_m$SO$_2$NR$^{13}$R$^{13}$, —(CH$_2$)$_n$—(Z)$_g$—(CHOR$^8$)$_m$—(Z)$_g$—SO$_2$NR$^{13}$R$^{13}$, -Het-(CH$_2$)$_n$—(Z)$_g$—(CHOR$^8$)$_m$—(Z)$_g$—SO$_2$NR$^{13}$R$^{13}$, —(CH$_2$)$_n$—CONR$^{13}$R$^{13}$, -Het-(CH$_2$)$_m$—CONR$^{13}$R$^{13}$, —(CH$_2$)$_n$—(Z)$_g$—CONR$^{13}$R$^{13}$, -Het-(CH$_2$)$_m$—(Z)$_g$—CONR$^{13}$R$^{13}$, —(CH$_2$)$_n$—NR$^{10}$—(CH$_2$)$_m$(CHOR$^8$)$_n$—CONR$^{13}$R$^{13}$, -Het-(CH$_2$)$_m$NR$^{10}$—(CH$_2$)$_m$(CHOR$^8$)$_n$—CONR$^{13}$R$^{13}$, —(CH$_2$)$_n$—(CHOR$^8$)$_m$—CONR$^{13}$R$^{13}$, -Het-(CH$_2$)$_m$—(CHOR$^8$)$_m$—CONR$^{13}$R$^{13}$, —(CH$_2$)$_n$—(CHOR$^8$)$_m$—(Z)$_g$—CONR$^{13}$R$^{13}$, -Het-(CH$_2$)$_n$—(CHOR$^8$)$_m$—(Z)$_g$—CONR$^{13}$R$^{13}$, —(CH$_2$)$_n$—(Z)$_g$—(CH$_2$)$_m$CONR$^{13}$R$^{13}$, -Het-(CH$_2$)$_n$—(Z)$_g$—(Z)$_g$—CONR$^{13}$R$^{13}$, —(CH$_2$)$_n$—CONR$^7$COR$^{13}$, -Het-(CH$_2$)$_m$—CONR$^7$COR$^{13}$, —(CH$_2$)$_n$—(Z)$_g$—CONR$^7$COR$^{13}$, -Het(CH$_2$)$_m$—(Z)$_g$—CONR$^7$COR$^{13}$, —(CH$_2$)$_n$—NR$^{10}$—(CH$_2$)$_m$ (CHOR$^8$)$_m$—CONR$^7$COR$^{13}$, -Het-(CH$_2$)$_m$NR$^{10}$—(CH$_2$)$_m$(CHOR$^8$)$_m$—CONR$^7$COR$^{13}$, —(CH$_2$)$_n$(CHOR$^8$)$_n$—CONR$^7$COR$^{13}$, -Het-(CH$_2$)$_m$—(CHOR$^8$)$_m$—(Z)$_g$—CONR$^7$COR$^{13}$, —(CH$_2$)$_n$—(Z)$_g$—(CH$_2$)$_m$CONR$^7$COR$^{13}$, —(CH$_2$)$_n$—(Z)$_g$—(CH$_2$)$_m$CONR$^7$COR$^{13}$, -Het-(CH$_2$)$_n$—(Z)$_g$—(CHOR$^8$)$_n$—(Z)$_g$—CONR$^7$COR$^{13}$, —(CH$_2$)$_n$—CONR$^7$CO$_2$R$^{13}$, —(CH$_2$)$_n$—(Z)$_g$—CONR$^7$CO$_2$R$^{13}$, -Het-(CH$_2$)$_n$—(Z)$_g$—CONR$^7$CO$_2$R$^{13}$, —(CH$_2$)$_n$—NR$^{10}$—(CH$_2$)$_m$(CHOR$^8$)$_n$—CONR$^7$CO$_2$R$^{13}$, -Het-(CH$_2$)$_m$—NR$^{10}$—(CH$_2$)$_m$(CHOR$^8$)$_n$—CONR$^7$CO$_2$R$^{13}$, —(CH$_2$)$_n$—(CHOR$^8$)$_m$—CONR$^7$CO$_2$R$^{13}$, -Het-(CH$_2$)$_m$—(CHOR$^8$)$_m$—CONR$^7$CO$_2$R$^{13}$, —(CH$_2$)$_n$—(CHOR$^8$)$_m$—(Z)$_g$—CONR$^7$CO$_2$R$^{13}$, -Het-(CH$_2$)$_m$—(CHOR$^8$)$_m$—(Z)$_g$—CONR$^7$CO$_2$R$^{13}$, —(CH$_2$)$_n$—(Z)$_g$—(CH$_2$)$_m$—CONR$^7$CO$_2$R$^{13}$, -Het-(CH$_2$)$_n$—(Z)$_g$-(CH$_2$)$_m$(CONR$^7$CO$_2$R$^{13}$, —(CH$_2$)$_n$—(Z)$_g$—(CHOR$^8$)$_m$—Z$_g$—CONR$^7$CO$_2$R$^{13}$, -Het-(CH$_2$)$_n$—(Z)$_g$-(CHOR$^8$)$_m$—(Z)$_g$—CONR$^7$CO$_2$R$^{13}$, —(CH$_2$)$_n$—NH—C(=NR$^{13}$)—NR$^{13}$R$^{13}$, -Het-(CH$_2$)$_m$—NH—C(=NR$^{13}$)—NR$^{13}$R$^{13}$, —(CH$_2$)$_n$—(Z)$_g$—NH—C(=NR$^{13}$)—NR$^{13}$R$^{13}$-Het-(CH$_2$)$_n$—(Z)$_g$—NH—C(=NR$^{13}$)—NR$^{13}$R$^{13}$, —(CH$_2$)$_n$—NR$^{10}$—(CH$_2$)$_m$(CHOR$^8$)$_n$—NH—C(=NR$^{13}$)—NR$^{13}$R$^{13}$, -Het-(CH$_2$)$_m$—NR$^{10}$—(CH$_2$)$_m$(CHOR$^8$)$_n$—NH—C(=NR$^{13}$)—NR$^{13}$R$^{13}$, —(CH$_2$)$_n$—(CHOR$^8$)$_m$—NH—C(=NR$^{13}$)—NR$^{13}$R$^{13}$, -Het-(CH$_2$)$_m$—(CHOR$^8$)$_m$—NH—C(=NR$^{13}$)—NR$^{13}$R$^{13}$, —(CH$_2$)$_n$—(CHOR$^8$)$_m$—(Z)$_g$—NH—C(=NR$^{13}$)—NR$^{13}$R$^{13}$, -Het-(CH$_2$)$_n$—(CHOR$^8$)$_m$—(Z)$_g$—NH—C(=NR$^{13}$)—NR$^{13}$R$^{13}$, —(CH$_2$)$_n$—(Z)$_g$(CH$_2$)$_m$NH—C(=NR$^{13}$)—NR$^{13}$R$^{13}$, -Het-(CH$_2$)$_n$—(Z)$_g$—(CH$_2$)$_m$NH—C(=NR$^{13}$)—NR$^{13}$R$^{13}$, —(CH$_2$)$_n$—Z$_g$—(CHOR$^8$)$_m$—(Z)$_g$—NH—C(=NR$^{13}$)—NR$^{13}$R$^{13}$, -Het-(CH$_2$)$_n$—(Z)$_g$—(CHOR$^8$)$_m$—(Z)$_g$—NH—C(=NR$^{13}$)—NR$^{13}$R$^{13}$, —(CH$_2$)$_n$—C(=NR$^{13}$)—NR$^{13}$R$^{13}$, Het-(CH$_2$)$_m$—C(=NH)—NR$^{13}$R$^{13}$, —(CH$_2$)$_n$—(Z)$_g$—C(=NH)—NR$^{13}$R$^{13}$, Het-(CH$_2$)$_m$—(Z)$_g$—C(=NH)—NR$^{13}$R$^{13}$, —(CH$_2$)$_n$—NR$^{10}$—(CH$_2$)$_m$—(CHOR$^8$)$_n$—C(=NR$^{13}$)—NR$^{13}$R$^{13}$, Het-(CH$_2$)$_m$—NR$^{10}$—(CH$_2$)$_m$(CHOR$^8$)$_n$—C(=NR$^{13}$)—NR$^{13}$R$^{13}$, —(CH$_2$)$_n$—(CHOR$^8$)$_m$—C(=NR$^{13}$)—NR$^{13}$R$^{13}$, -Het-(CH$_2$)$_n$—(CHOR$^8$)$_m$—C(=NR$^{13}$)—NR$^{13}$R$^{13}$, —(CH$_2$)$_n$—(CHOR$^8$)$_m$—(Z)$_g$—C(=NR$^{13}$)—NR$^{13}$R$^{13}$—NR$^{13}$R$^{13}$, -Het-(CH$_2$)$_n$—(Z)$_g$—(CH$_2$)$_m$—C(=NR$^{13}$)—NR$^{13}$R$^{13}$, —(CH$_2$)$_n$—(Z)$_g$—(CHOR$^8$)$_m$—(Z)$_g$—C(=NR$^{13}$)—NR$^{13}$R$^{13}$, -Het-(CH$_2$)$_n$—(Z)$_g$—(CHOR$^8$)$_m$—(Z)$_g$—C(=NR$^{13}$)—NR$^{13}$R$^{13}$, —(CH$_2$)$_n$—NR$^{12}$R$^{12}$, —O—(CH$_2$)$_m$—NR$^{12}$R$^{12}$, —O—(CH$_2$)$_m$(Z)$_g$—R$^{12}$, —(CH$_2$)$_n$NR$^{11}$R$^{11}$, —O—(CH$_2$)$_m$NR$^{11}$R$^{11}$, —(CH$_2$)$_n$—N$^{\oplus}$—(R$^{11}$)$_3$, —O—(CH$_2$)$_m$—N$^{\oplus}$—(R$^{11}$)$_3$, —(CH$_2$)$_n$—(Z)$_g$—(CH$_2$)$_m$—NR$^{10}$R$^{10}$, —O—(CH$_2$)$_m$—(Z)$_g$—(CH$_2$)$_m$—NR$^{10}$R$^{10}$, —(CH$_2$CH$_2$O)$_m$—CH$_2$CH$_2$NR$^{12}$R$^{12}$, —O—(CH$_2$CH$_2$O)$_m$—CH$_2$CH$_2$NR$^{12}$R$^{12}$, —(CH$_2$)$_n$—(C=O)NR$^{12}$R$^{12}$, —O—(CH$_2$)$_m$—(C=O)NR$^{12}$R$^{12}$, —O—(CH$_2$)$_m$—(CHOR$^8$)$_m$CH$_2$NR$^{10}$—(Z)$_g$—R$^{10}$, —(CH$_2$)$_n$—(CHOR$^8$)$_m$—CH$_2$—NR$^{10}$—(Z)$_g$—R$^{10}$, —(CH$_2$)$_n$NR$^{10}$—O(CH$_2$)$_m$(CHOR$^8$)$_n$CH$_2$NR$^{10}$—(Z)$_g$—R$^{10}$, —O(CH$_2$)$_m$—NR$^{10}$—(CH$_2$)$_m$—(CHOR$^8$)$_n$CH$_2$NR$^{10}$—(Z)$_g$—R$^{10}$, -(Het)-(CH$_2$)$_m$—OR$^8$, -(Het)-(CH$_2$)$_m$—NR$^7$R$^{10}$, -(Het)-(CH$_2$)$_m$(CHOR$^8$)(CHOR$^8$)$_n$—CH$_2$OR$^8$, -(Het)-(CH$_2$CH$_2$O)$_m$—R$^8$, -(Het)-(CH$_2$CH$_2$O)$_m$—CH$_2$CH$_2$NR$^7$R$^{10}$, -(Het)-(CH$_2$)$_m$—C(=O)NR$^7$R$^{10}$, -(Het)-(CH$_2$)$_m$—(Z)$_g$—R$^7$, -(Het)-(CH$_2$)$_m$—NR$^{10}$—CH$_2$(CHOR$^8$)(CHOR$^8$)$_n$—CH$_2$OR$^8$, -(Het)-(CH$_2$)$_m$—CO$_2$R$^7$, -(Het)-(CH$_2$)$_m$—NR$^{12}$R$^{12}$, -(Het)-(CH$_2$)$_n$—NR$^{12}$R$^{12}$, -(Het)-(CH$_2$)$_m$—(Z)$_g$R$^{12}$, -(Het)-(CH$_2$)$_m$NR$^{11}$R$^{11}$, -(Het)-(CH$_2$)$_m$—N$^{\oplus}$—(R$^{11}$)$_3$, -(Het)-(CH$_2$)$_m$—(Z)$_g$—(CH$_2$)$_m$—NR$^{10}$R$^{10}$, -(Het)-(CH$_2$CH$_2$O)$_m$—CH$_2$CH$_2$NR$^{12}$R$^{12}$, -(Het)-(CH$_2$)$_m$—(C=O)NR$^{12}$R$^{12}$, -(Het)-(CH$_2$)$_m$—(CHOR$^8$)$_m$CH$_2$NR$^{10}$—(Z)$_g$—R$^{10}$, —(CH$_2$)$_m$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$)$_n$—NR$^{10}$—CH$_2$(CHOR$^8$)(CHOR$^8$)$_n$—CH$_2$OR$^8$, —O—(CH$_2$)$_n$—NR$^{10}$—CH$_2$(CHOR$^8$)(CHOR$^8$)$_n$—CH$_2$OR$^8$, Link-(CH$_2$)$_n$-CAP, Link-(CH$_2$)$_n$(CHOR$^8$)(CHOR$^8$)$_n$-CAP, Link-(CH$_2$CH$_2$O)$_m$—CH$_2$-CAP, Link-(CH$_2$CH$_2$O)$_m$—CH$_2$CH$_2$-CAP, Link-(CH$_2$)$_n$—(Z)$_g$-CAP, Link-(CH$_2$)$_n$(Z)$_g$—(CH$_2$)$_m$-CAP, Link-(CH$_2$)$_n$—NR$^{13}$—CH$_2$(CHOR$^8$)(CHOR$^8$)$_n$-CAP, Link-(CH$_2$)$_n$—(CHOR$^8$)$_m$CH$_2$—NR$^{13}$—(Z)$_g$-CAP, Link-(CH$_2$)$_n$NR$^{13}$—(CH$_2$)$_m$(CHOR$^8$)$_n$CH$_2$NR$^{13}$—(Z)$_g$-CAP, -Link-(CH$_2$)$_n$—(Z)$_g$—(CH$_2$)$_m$-CAP, Link-NH—C(=O)—NH—(CH$_2$)$_m$-CAP, Link (CH$_2$)$_m$—C(=O)NR$^{13}$—(CH$_2$)$_m$—C(=O)NR$^{10}$R$^{10}$, Link-(CH$_2$)$_m$—C(=O)NR$^{13}$—(CH$_2$)$_m$-CAP, Link-(CH$_2$)$_m$—C(=O)NR$^{11}$R$^{11}$, Link-(CH$_2$)$_m$C(=O)NR$^{12}$R$^{12}$, Link-(CH$_2$)$_n$—(Z)$_g$—(CH$_2$)$_m$—(Z)$_g$-CAP, Link (Z)$_g$—(CH$_2$)$_m$-Het-(CH$_2$)$_m$-CAP, Link (CH$_2$)$_n$—CR$^{11}$R$^{11}$-CAP, Link-(CH$_2$)$_n$(CHOR$^8$)(CHOR$^8$)$_n$—CR$^{11}$R$^{11}$-CAP, Link-(CH$_2$CH$_2$O)$_m$—CH$_2$—CR$^{11}$R$^{11}$-CAP, Link-(CH$_2$CH$_2$O)$_m$—CH$_2$CH$_2$—CR$^{11}$R$^{11}$-CAP, Link-(CH$_2$)$_n$—(Z)$_g$—CR$^{11}$R$^{11}$-CAP, Link-(CH$_2$)$_n$(Z)$_g$—(CH$_2$)$_m$—CR$^{11}$R$^{11}$-CAP, Link-(CH$_2$)$_n$—NR$^{13}$—CH$_2$(CHOR$^8$)(CHOR$^8$)$_n$—CR$^{11}$R$^{11}$-CAP, Link-(CH$_2$)$_n$—(CHOR$^8$)$_m$CH$_2$—NR$^{13}$—(Z)$_g$—CR$^{11}$R$^{11}$-CAP, Link-(CH$_2$)$_n$NR$^{13}$—(CH$_2$)$_m$(CHOR$^8$)$_n$CH$_2$NR$^{13}$—(Z)$_g$—CR$^{11}$R$^{11}$-CAP, Link-(CH$_2$)$_n$—(Z)$_g$-(CH$_2$)$_m$—CR$^{11}$R$^{11}$-CAP, Link NH—C(=O)—NH—(CH$_2$)$_m$—CR$^{11}$R$^{11}$-CAP, Link-(CH$_2$)$_m$—C(=O)NR$^{13}$—(CH$_2$)$_m$—CR$^{11}$R$^{11}$-CAP, Link-(CH$_2$)$_n$—(Z)$_g$—(CH$_2$)$_m$—(Z)$_g$—CR$^{11}$R$^{11}$-CAP, or Link-(Z)$_g$—(CH$_2$)$_m$-Het-(CH$_2$)$_m$—CR$^{11}$R$^{11}$-CAP;

each R$^6$ is, independently, R$^5$, —R$^7$, —OR$^{11}$, —N(R$^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_m$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—O(CH$_2$)$_n$—(Z)$_g$—R$^7$, —(CH$_2$)$_m$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$), —CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

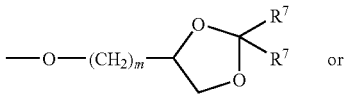 or

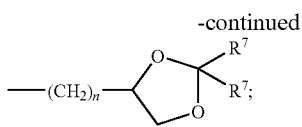

wherein when two $R^6$ are $-OR^{11}$ and are located adjacent to each other on the aromatic carbocycle or aromatic heterocycle, the two $OR^{11}$ may form a methylenedioxy group;

each $R^7$ is, independently, hydrogen, lower alkyl, phenyl, substituted phenyl or $-CH_2(CHOR^8)_m-CH_2OR^8$;

each $R^8$ is, independently, hydrogen, lower alkyl, $-C(=O)-R^{11}$, glucuronide, 2-tetrahydropyranyl, or

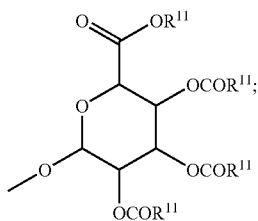

each $R^9$ is, independently, $-CO_2R^7$, $-CON(R^7)_2$, $-SO_2CH_3$, $-C(=O)R^7$, $-CO_2R^{13}$, $-CON(R^{13})_2$, $-SO_2CH_2R^{13}$, or $-C(=O)R^{13}$;

each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;

each Z is, independently, $-(CHOH)-$, $-C(=O)-$, $-(CHNR^7R^{10})-$, $-(C=NR^{10})-$, $-NR^{10}-$, $-(CH_2)_n-$, $-(CHNR^{13}R^{13})-$, $-(C=NR^{13})-$, or $-NR^{13}-$;

each $R^{11}$ is, independently, hydrogen, lower alkyl, phenyl lower alkyl or substituted phenyl lower alkyl;

each $R^{12}$ is, independently, $-SO_2CH_3$, $-CO_2R^7$, $-C(=O)NR^7R^9$, $-C(=O)R^7$, $-CH_2(CHOH)_n-CH_2OH$, $-CO_2R^{13}$, $-C(=O)NR^{13}R^{13}$, or $-C(=O)R^{13}$;

each $R^{13}$ is, independently, $R^7$, $R^{10}$, $-(CH_2)_m-NR^7R^{10}$, $-(CH_2)_m-NR^7R^7$, $-(CH_2)_m-NR^{11}R^{11}$, $-(CH_2)_m-(NR^{11}R^{11}R^{11})^+$, $-(CH_2)_m-(CHOR^8)_m-(CH_2)_mNR^{11}R^{11}$, $-(CH_2)_m-(CHOR^8)_m-(CH_2)_mNR^7R^{10}$, $-(CH_2)_m-NR^{10}R^{10}$, $-(CH_2)_m-(CHOR^8)_m-(CH_2)_m-(NR^{11}R^{11}R^{11})^+$, $-(CH_2)_m-(CHOR^8)_m-(CH_2)_mNR^7R^7$,

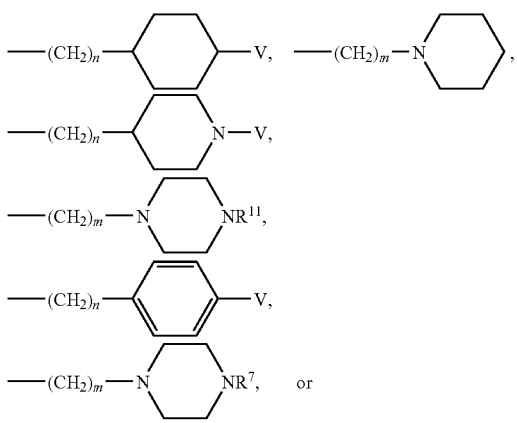

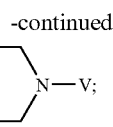

with the proviso that in the moiety $-NR^{13}R^{13}$, the two $R^{13}$ along with the nitrogen to which they are attached may, optionally, form a ring selected from:

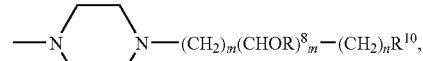

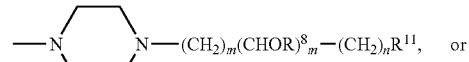

each V is, independently, $-(CH_2)_m-NR^7R^{10}$, $-(CH_2)_m-NR^7R^7$, $-(CH_2)_m-(NR^{11}R^{11}R^{11})^+$, $-(CH_2)_m-(CHOR^8)_m-(CH_2)_n-NR^7R^{10}$, $-(CH_2)_n-NR^{10}R^{10}$, $-(CH_2)_n-(CHOR^8)_m-(CH_2)_mNR^7R^7$, $-(CH_2)_n-(CHOR^8)_m-(CH_2)_m-(NR^{11}R^{11}R^{11})^+$ with the proviso that when V is attached directly to a nitrogen atom, then V can also be, independently, $R^7$, $R^{10}$, or $(R^{11})_2$;

each $R^{14}$ is, independently, H, $R^{12}$, $-(CH_2)_n-SO_2CH_3$, $-(CH_2)$, $-CO_2R^{13}$, $-(CH_2)_n-C(=O)NR^{13}R^{13}$, $-(CH_2)_n-C(=O)R^{13}$, $-(CH_2)_n-(CHOH)_n-CH_2OH$, $-NH-(CH_2)_n-SO_2CH_3$, $NH-(CH_2)_n-C(=O)R^{11}$, $NH-C(=O)-NH-C(=O)R^{11}$, $-C(=O)NR^{13}R^{13}$, $-OR^{11}$, $-NH-(CH_2)_n-R^{10}$, $-Br$, $-Cl$, $-F$, $-I$, $SO_2NHR^{11}$, $-NHR^{13}$, $-NH-C(=O)-NR^{13}R^{13}$, $-(CH_2)_n-NHR^{13}$, or $-NH-(CH_2)_n-C(=O)-R^{13}$;

each g is, independently, an integer from 1 to 6;

each m is, independently, an integer from 1 to 7;

each n is, independently, an integer from 0 to 7;

each -Het- is, independently, $-N(R^7)-$, $-N(R^{10})-$, $-S-$, $-SO-$, $-SO_2-$, $-O-$, $-SO_2NH-$, $-NHSO_2-$, $-NR^7CO-$, $-CONR^7-$, $-N(R^{13})-$, $-SO_2NR^{13}-$, $-NR^{13}CO-$, or $-CONR^{13}-$;

each Link is, independently, $-O-$, $-(CH_2)_m-$, $-O(CH_2)_m-$, $-NR^{13}-C(=O)-NR^{13}-$, $-NR^{13}-C(=O)-(CH_2)_m-$, $-C(=O)NR^{13}-(CH_2)_m-$, $-(CH_2)_n-(Z)_g-(CH_2)_n-$, $-S-$, $-SO-$, $-SO_2-$, $-SO_2NR^7-$, $-SO_2NR^{10}-$, or -Het-;

each CAP is, independently, thiazolidinedione, oxazolidinedione, -heteroaryl-C(=O)N $R^{13}R^{13}$, heteroaryl-W, $-CN$, $-O-C(=S)NR^{13}R^{13}$, $-(Z)_gR^{13}$, $-CR^{10}((Z)_gR^{13})((Z)_gR^{13})$, $-C(=O)OAr$, $-C(=O)NR^{13}Ar$, imidazoline, tetrazole, tetrazole amide, $-SO_2NHR^{13}$, $-SO_2NH-C(R^{13}R^{13})-(Z)_g-R^{13}$, a cyclic sugar or oligosaccharide, a cyclic amino sugar, oligosaccharide, $-CR^{10}(-(CH_2)_m-R^9)(-(CH_2)_m-R^9)$, $-N(-(CH_2)_m-R^9)(-(CH_2)_m-R^9)$, $-NR^{13}(-(CH_2)_n-CO_2R^{13})$,

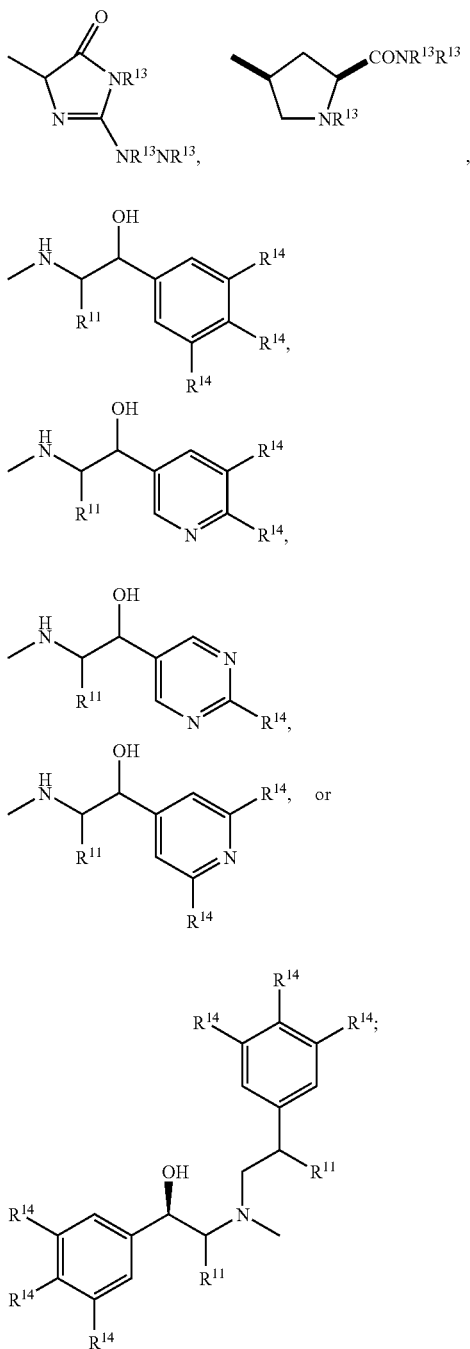

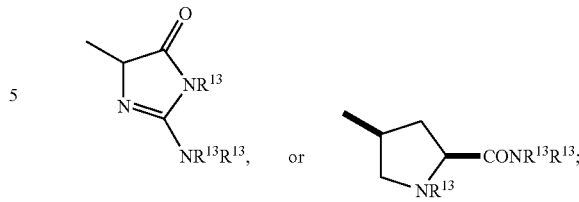

with the proviso that when any —CHOR$^8$— or CH$_2$OR$^8$ groups are located 1,2- or 1,3- with respect to each other, the R$^8$ groups may, optionally, be taken together to form a cyclic mono- or di-substituted 1,3-dioxane or 1,3-dioxolane.

The present also provides pharmaceutical compositions which comprise a compound described herein.

The present invention also provides a method of promoting hydration of mucosal surfaces, comprising:

administering an effective amount of a compound described herein to a mucosal surface of a subject.

The present invention also provides a method of restoring mucosal defense, comprising:

topically administering an effective amount of compound described herein to a mucosal surface of a subject in need thereof.

The present invention also provides a method of blocking ENaC, comprising:

contacting sodium channels with an effective amount of a compound represented by described herein.

The present invention also provides a method of promoting mucus clearance in mucosal surfaces, comprising:

administering an effective amount of a compound represented described herein to a mucosal surface of a subject.

The present invention also provides a method of treating chronic bronchitis, comprising:

administering an effective amount of a compound described herein to a subject in need thereof.

The present invention also provides a method of treating cystic fibrosis, comprising:

administering an effective amount of compound described herein to a subject in need thereof.

The present invention also provides a method of treating rhinosinusitis, comprising:

administering an effective amount of a compound described herein to a subject in need thereof.

The present invention also provides a method of treating nasal dehydration, comprising:

administering an effective amount of a compound described herein to the nasal passages of a subject in need thereof.

In a specific embodiment, the nasal dehydration is brought on by administering dry oxygen to the subject.

The present invention also provides a method of treating sinusitis, comprising:

administering an effective amount of a compound described herein to a subject in need thereof.

The present invention also provides a method of treating pneumonia, comprising:

administering an effective amount of a compound described herein to a subject in need thereof.

The present invention also provides a method of treating ventilator-induced pneumonia, comprising:

administering an effective compound described herein to a subject by means of a ventilator.

The present invention also provides a method of treating asthma, comprising:

each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl; and each W is, independently, thiazolidinedione, oxazolidinedione, heteroaryl-C(=O)N R$^{13}$R$^{13}$, —CN, —O—C(=S)NR$^{13}$R$^{13}$, —(Z)$_g$R$^{13}$, —CR$^{10}$((Z)$_g$R$^{13}$)((Z)$_g$R$^{13}$), —C(=O)OAr, —C(=O)N R$^{13}$Ar, imidazoline, tetrazole, tetrazole amide, —SO$_2$NHR$^3$, —SO$_2$NH—C(R$^{13}$R$^{13}$) —(Z)$_g$—R$^{13}$, a cyclic sugar or oligosaccharide, a cyclic amino sugar, oligosaccharide, administering an effective amount of a compound described herein to a subject in need thereof.

The present invention also provides a method of treating primary ciliary dyskinesia, comprising:
administering an effective amount of a compound described herein to a subject in need thereof.

The present invention also provides a method of treating otitis media, comprising:
administering an effective amount of a compound described herein to a subject in need thereof.

The present invention also provides a method of inducing sputum for diagnostic purposes, comprising:
administering an effective amount of compound described herein to a subject in need thereof.

The present invention also provides a method of treating chronic obstructive pulmonary disease, comprising:
administering an effective amount of a compound described herein to a subject in need thereof.

The present invention also provides a method of treating emphysema, comprising:
administering an effective amount of a compound described herein to a subject in need thereof.

The present invention also provides a method of treating dry eye, comprising:
administering an effective amount of a compound described herein to the eye of the subject in need thereof.

The present invention also provides a method of promoting ocular hydration, comprising:
administering an effective amount of a compound described herein to the eye of the subject.

The present invention also provides a method of promoting corneal hydration, comprising:
administering an effective amount of a compound described herein to the eye of the subject.

The present invention also provides a method of treating Sjögren's disease, comprising:
administering an effective amount of compound described herein to a subject in need thereof.

The present invention also provides a method of treating vaginal dryness, comprising:
administering an effective amount of a compound described herein to the vaginal tract of a subject in need thereof.

The present invention also provides a method of treating dry skin, comprising:
administering an effective amount of a compound described herein to the skin of a subject in need thereof.

The present invention also provides a method of treating dry mouth (xerostomia), comprising:
administering an effective amount of compound described herein to the mouth of the subject in need thereof.

The present invention also provides a method of treating distal intestinal obstruction syndrome, comprising:
administering an effective amount of compound described herein to a subject in need thereof.

The present invention also provides a method of treating esophagitis, comprising:
administering an effective amount of a compound described herein to a subject in need thereof.

The present invention also provides a method of treating bronchiectasis, comprising:
administering an effective amount of a compound described herein to a subject in need thereof.

The present invention also provides a method of treating constipation, comprising:
administering an effective amount of a compound described herein to a subject in need thereof. In one embodiment of this method, the compound is administered either orally or via a suppository or enema.

The present invention also provides a method of treating chronic diverticulitis comprising:
administering an effective amount of a compound described herein to a subject in need thereof.

The present invention also provides a method of treating hypertension, comprising administering the compound described herein to a subject in need thereof.

The present invention also provides a method of reducing blood pressure, comprising administering the compound described herein to a subject in need thereof.

The present invention also provides a method of treating edema, comprising administering the compound described herein to a subject in need thereof.

The present invention also provides a method of promoting diuresis, comprising administering the compound described herein to a subject in need thereof.

The present invention also provides a method of promoting natriuresis, comprising administering the compound described herein to a subject in need thereof.

The present invention also provides a method of promoting saluresis, comprising administering the compound described herein to a subject in need thereof.

It is an object of the present invention to provide treatments comprising the use of osmolytes together with sodium channel blockers of formula (I) that are more potent, more specific, and/or absorbed less rapidly from mucosal surfaces, and/or are less reversible as compared to compounds such as amiloride, benzamil, and phenamil.

It is another aspect of the present invention to provide treatments using sodium channel blockers of formula (I) that are more potent and/or absorbed less rapidly and/or exhibit less reversibility, as compared to compounds such as amiloride, benzamil, and phenamil when administered with an osmotic enhancer. Therefore, such sodium channel blockers when used in conjunction with osmolytes will give a prolonged pharmacodynamic half-life on mucosal surfaces as compared to either compound used alone.

It is another object of the present invention to provide treatments using sodium channel blockers of formula (I) and osmolytes together which are absorbed less rapidly from mucosal surfaces, especially airway surfaces, as compared to compounds such as amiloride, benzamil, and phenamil.

It is another object of the invention to provide compositions which contain sodium channel blockers of formula (I) and osmolytes.

The objects of the invention may be accomplished with a method of treating a disease ameliorated by increased mucociliary clearance and mucosal hydration comprising administering an effective amount of a compound of formula (I) as defined herein and an osmolyte to a subject to a subject in need of increased mucociliary clearance and mucosal hydration.

The objects of the invention may also be accomplished with a method of inducing sputum for diagnostic purposes, comprising administering an effective amount of a compound of formula (I) as defined herein and an osmolyte to a subject in need thereof.

The objects of the invention may also be accomplished with a method of treating anthrax, comprising administering an effective amount of a compound of formula (I) as defined herein and an osmolyte to a subject in need thereof.

The objects of the invention may also be accomplished with a method of prophylactic, post-exposure prophylactic, preventive or therapeutic treatment against diseases or conditions caused by pathogens, particularly pathogens which may be used in bioterrorism, comprising administering an effective amount of a compound of formula (I) to a subject in need thereof.

The objects of the invention may also be accomplished with a composition, comprising a compound of formula (I) as defined herein and an osmotically active compound.

DETAILED DESCRIPTION OF THE INVENTION

The present invention is based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels as compared to the parent administered compound, after they are absorbed from mucosal surfaces after administration. This important property means that the compounds will have a lower tendency to cause undesired side-effects by blocking sodium channels located at untargeted locations in the body of the recipient, e.g., in the kidneys.

The present invention is also based on the discovery that certain compounds embraced by formula (I) target the kidney and thus may be used as cardiovascular agents.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1,2,3, 4, 5, 6, and 7 carbon atoms. The term "alkyl" embraces all types of such groups, e.g., linear, branched, and cyclic alkyl groups. This description is applicable to the tern "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or $—N(R^2)_2$. The alkyl moiety of the lower alkoxy groups is the same as described above. Examples of mononuclear aryl include phenyl groups. The phenyl group may be unsubstituted or substituted as described above. The preferred identity of Y is $—N(R^2)_2$. Particularly preferred are such compounds where each $R^2$ is hydrogen.

$R^1$ may be hydrogen or lower alkyl. Hydrogen is preferred for $R^1$.

Each $R^2$ may be, independently, $—R^7$, $—(CH_2)_m—OR^8$, $—(CH_2)_m—NR^7R^{10}$, $—(CH_2)_n(CHOR^8)(CHOR^8)_n—CH_2OR^8$, $—(CH_2CH_2O)_m—R^8$, $—(CH_2CH_2O)_m—CH_2CH_2NR^7R^{10}$, $—(CH_2)_n—C(=O)NR^7R^{10}$, $—(CH_2)_n—(Z)_g—R^7—(CH_2)_m—NR^{10}—CH_2(CHOR^8)(CHOR^8)_n—CH_2OR^8$, $—(CH_2)_n—CO_2R^7$, or 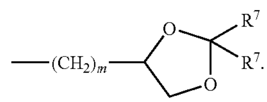 Hydrogen and lower alkyl, particularly $C_1$-$C_3$ alkyl, are preferred for $R^2$. Hydrogen is particularly preferred.

$R^3$ and $R^4$ may be, independently, hydrogen, lower alkyl, hydroxyl-lower alkyl, phenyl, (phenyl)-lower alkyl, (halophenyl)-lower alkyl, ((lower-alkyl)phenyl)-lower-alkyl), (lower-alkoxyphenyl)-lower alkyl, (naphthyl)-lower alkyl, (pyridyl)-lower alkyl or a group represented by $—(C(R^L)_2)_o$-x-$(C(R^L)_2)_pA^1$ or $—(C(R^L)_2)_o$-x-$(C(R^L)_2)_pA^2$, provided that at least one of $R^3$ and $R^4$ is a group represented by $—(C(R^L—)_2)_o$-x-$(C(R^L)_2)A^1$ or $—(C(R^L)_2)_o$-x-$(C(R^L—)_2)_pA^2$.

Preferred compounds are those where one of $R^3$ and $R^4$ is hydrogen and the other is represented by $—(C(R^L—)_2)_o$-x-$(C(R^L)_2)_pA^1$ or $—(C(R^L)_2)_o$-x-$(C(R^L)_2)_pA^2$. In a particularly preferred aspect one of $R^3$ and $R^4$ is hydrogen and the other of $R^{33}$ or $R^{44}$ is represented by $—(C(R^L)_2)_o$-x-$(C(R^L)_2)_pA^1$. In another particularly preferred aspect one of $R^3$ and $R^4$ is hydrogen and the other of $R^3$ or $R^4$ is represented by $—(C(R^L)_2)_o$-x-$(C(R^L)_2)_pA^2$.

A moiety $—(C(R^L)_2)_o$-x-$(C(R^L)_2)_p—$ defines an alkylene group bonded to the group $A^1$ or $A^2$. The variables o and p may each, independently, be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, C(=O), CHOH, C(=N—$R^{10}$), $CHNR^7R^{10}$, or a single bond;

Therefore, when x is a single bond, the alkylene chain bonded to the ring is represented by the formula $—(C(R^L)_2)_{o+p}$, in which the sum o+p is from 1 to 10.

Each $R^L$ may be, independently, $—R^7$, $—(CH_2)_n—OR^8$, $—O—(CH_2)_m—OR^8$, $—(CH_2)_n—NR^7R^{10}$, $—O—(CH_2)_n—NR^7R^{10}$, $—(CH_2)_n(CHOR^8)(CHOR^8)_n—CH_2OR^8$, $—O—(CH_2)_m(CHOR^8)(CHOR^8)_n—CH_2OR^8$, $—(CH_2CH_2O)_m—R^8$, $—O—(CH_2CH_2O)_m—R^8$, $—(CH_2CH_2O)_m—CH_2CH_2NR^7R^{10}$, $—O—(CH_2CH_2O)_m—CH_2CH_2NR^7R^{10}$, $—(CH_2)_n—C(=O)NR^7R^{10}$, $—O—(CH_2)_m—C(=O)NR^7R^{10}$, $—(CH_2)_n—(Z)_g—R^7$, $—O—(CH_2)_m—(Z)_g—R^7$, $—(CH_2)_n—NR^{10}—CH_2(CHOR^8)(CHOR^8)_n—CH_2OR^8$, $—O—(CH_2)_m—NR^{10}—CH_2(CHOR^8)(CHOR^8)_n—CH_2OR^8$, $—(CH_2)_n—CO_2R^7$, $—O—(CH_2)_m—CO_2R^7$, $—OSO_3H$, —O-glucuronide, —O-glucose, 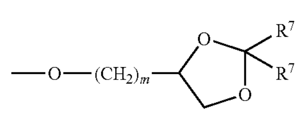 or The term O-glucuronide, unless otherwise specified, means a group represented by

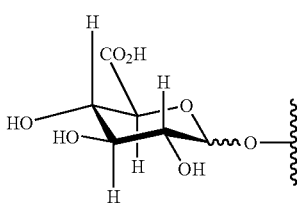

wherein the ⟿O means the glycosidic linkage can be above or below the plane of the ring.

The term —O-glucose, unless otherwise specified, means a group represented by

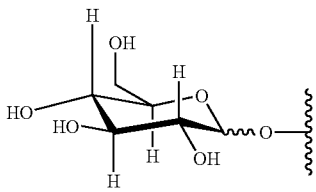

wherein the ⟿O means the glycosidic linkage can be above or below the plane of the ring.

The preferred $R^L$ groups include —H, —OH, —N($R^7$)$_2$, especially where each $R^7$ is hydrogen.

In the alkylene chain in —(C($R^L$)$_2$)$_o$-x-(C($R^L$)$_2$)$_p$$A^1$ or —(C($R^L$)$_2$)$_o$-x-(C($R^L$)$_2$)$_p$$A^2$, it is preferred that when one $R^L$ group bonded to a carbon atoms is other than hydrogen, then the other $R^L$ bonded to that carbon atom is hydrogen, i.e., the formula —CHR$^L$—. It is also preferred that at most two $R^L$ groups in an alkylene chain are other than hydrogen, wherein the other $R^L$ groups in the chain are hydrogens. Even more preferably, only one $R^L$ group in an alkylene chain is other than hydrogen, wherein the other $R^L$ groups in the chain are hydrogens. In these embodiments, it is preferable that x is a single bond.

In another particular embodiment of the invention, all of the $R^L$ groups in the alkylene chain are hydrogen. In these embodiments, the alkylene chain is represented by the formula —(CH$_2$)$_o$-x-(CH$_2$)$_p$—.

$A^1$ is a $C_7$-$C_{15}$-membered aromatic carbocycle substituted with at least one $R^5$ and the remaining substituents are $R^6$. The term aromatic is well known term of chemical art and designates conjugated systems of 4n'+2 electrons that are within a ring system, that is with 6, 10, 14, etc. π-electrons wherein, according to the rule of Huckel, n' is 1, 2, 3, etc. The 4n'+2 electrons may be in any size ring including those with partial saturation so long as the electrons are conjugated. For instance, but not by way of limitation, 5H-cyclohepta-1,3,5-triene, benzene, naphthalene, 1,2,3,4-tetrahydronaphthalene etc. would all be considered aromatic.

The $C_7$-$C_{15}$ aromatic carbocycle may be monocyclic, bicyclic, or tricyclic and may include partially saturated rings. Non-limiting examples of these aromatic carbocycles comprise 5H-cyclohepta-1,3,5-triene, naphthalene, phenanthrene, azulene, anthracene, 1,2,3,4-tetrahydronapthalene, 1,2-dihydronapthalene, indene, 5H-dibenzo[a,d]cycloheptene, etc.

The $C_7$-$C_{15}$ aromatic carbocycle may be attached to the —(C($R^L$)$_2$)$_o$-x-(C($R^L$)$_2$)$_p$— moiety through any ring carbon atom as appropriate, unless otherwise specified. Therefore, when partially saturated bicyclic aromatic is 1,2-dihydronapthalene, it may be 1,2-dihydronapthalen-1-yl, 1,2-dihydronapthalen-3-yl, 1,2-dihydronapthalen-5-yl, etc. In a preferred embodiment $A^1$ is indenyl, napthalenyl, 1,2-dihydronapthalenyl, 1,2,3,4-tetrahydronapthalenyl, anthracenyl, fluorenyl, phenanthrenyl, azulenyl, cyclohepta-1,3,5-trienyl or 5H-dibenzo[a,d]cycloheptenyl. In another preferred embodiment, $A^1$ is napthalen-1-yl. In another preferred embodiment, $A^1$ is napthalen-2-yl.

In another preferred embodiment, $A^1$ is

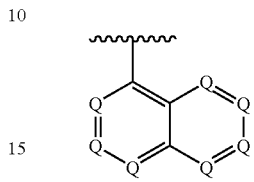

wherein each Q is, independently, C—H, C—$R^5$, or C—$R^6$, with the proviso that at least one Q is C—$R^5$. Therefore, Q may be 1, 2, 3, 4, 5, or 6 C—H. Therefore, Q may be 1, 2, 3, 4, 5, or 6 C—$R^6$. In a particularly preferred embodiment, each $R^6$ is H.

In another preferred embodiment, $A^1$ is

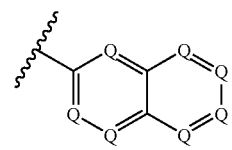

wherein each Q is, independently, C—H, C—$R^5$, C—$R^6$, with the proviso that at least one Q is C—$R^5$. Therefore, Q may be 1, 2, 3, 4, 5, or 6 C—H. Therefore, Q may be 1, 2, 3, 4, 5, or 6 C—$R^6$. In a particularly preferred embodiment, each $R^6$ is H.

In a particularly preferred embodiment, $A^1$ is

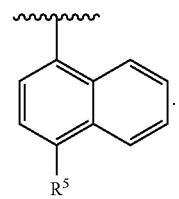

In another particularly preferred embodiment, $A^1$ is

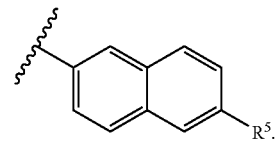

$A^2$ is a seven to fifteen-membered aromatic heterocycle substituted with at least one $R^5$ and the remaining substituents are $R^6$ wherein the aromatic heterocycle comprises 1-4 heteroatoms selected from the group consisting of O, N, and S.

The seven to fifteen-membered aromatic heterocycle may be monocyclic, bicyclic, or tricyclic and may include partially saturated rings. Non limiting examples of these aromatic heterocycles include 1H-azepine, benzo[b]furan, benzo[b]thiophene, isobenzofuran, isobenzothiophene, 2,3-dihydrobenzo[b]furan, benzo[b]thiophene, 2,3-dihydrobenzo[b]thiophene, indolizine, indole, isoindole benzoxazole, benzimidazole, indazole, benzisoxazole, benzisothizole, benzopyrazole, benzoxadiazole, benzothiadiazole, benzotriazole, purine, quinoline, 1,2,3,4-tetrahydroquinoline, 3,4-dihydro-2H-chromene, 3,4-dihydro-2H-thiochromene, isoquinoline, cinnoline, quinolizine, phthalazine, quinoxaline, quinazoline, naphthiridine, pteridine, benzopyrane, pyrrolopyridine, pyrrolopyrazine, imidazopyrdine, pyrrolopyrazine, thienopyrazine, furopyrazine, isothiazolopyrazine, thiazolopyrazine, isoxazolopyrazine, oxazolopyrazine, pyrazolopyrazine, imidazopyrazine, pyrrolopyrimidine, thienopyrimidine, furopyrimidine, isothiazolopyrimidine, thiazolopyrimidine, isoxazolopyrimidine, oxazolopyrimidine, pyrazolopyrimidine, imidazopyrimidine, pyrrolopyridazine, thienopyridazine, furopyridazine, isothiazolopyridazine, thiazolopyridazine, oxazolopyridazine, thiadiazolopyrazine, oxadiazolopyrimidine, thiadiazolopyrimidine, oxadiazolopyridazine, thiazolopyridazine, imidazooxazole, imidazothiazole, imidazoimidazole, isoxazolotriazine, isothiazolotriazine, oxazolotriazine, thiazolotriazine, carbazole, acridine, phenazine, phenothiazine, phenooxazine, and 5H-dibenz[b,f]azepine, 10,11-dihydro-5H-dibenz[b,f]azepine, etc.

The seven to fifteen-membered aromatic heterocycle may be attached to the $—(C(R^L)_2)_o$-x-$(C(R^L)_2)_p$— moiety through any ring carbon atom or ring nitrogen atom so long as a quanternary nitrogen atom is not formed by the attachment. Therefore, when partially saturated aromatic heterocycle is 1H-azepine, it may be 1H-azepin-1-yl, 1H-azepin-2-yl, 1H-azepin-3-yl, etc. Preferred aromatic heterocycles are indolizinyl, indolyl, isoindolyl, indolinyl, benzo[b]furanyl, 2,3-dihydrobenzo[b]furanyl, benzo[b]thiophenyl, 2,3-dihydrobenzo[b]thiophenyl, indazolyl, benzimidazolyl, benzthiazolyl, purinyl, quinolinyl, 1,2,3,4-tetrahydroquinolinyl, 3,4-dihydro-2H-chromenyl, 3,4-dihydro-2H-thiochromenyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, dibenzofuranyl, dibenzothiophenyl, 1H-azepinyl, 5H-dibenz[b,f]azepinyl, are 10,11-dihydro-5H-dibenz[b,f]azepinyl.

In another preferred embodiment, $A^2$ is

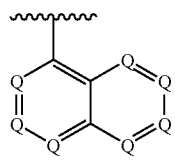

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, in any one ring, each Q may be 1, 2, or 3 nitrogen atoms. In a preferred embodiment, only one Q in each ring is nitrogen. In another preferred embodiment, only a single Q is nitrogen. Optionally, 1, 2, 3, 4, or 5 Q may be C—$R^6$. Optionally, Q may be 1, 2, 3, 4, or 5 C—H. In a particularly preferred embodiment, each $R^6$ is H.

In another preferred embodiment, $A^2$ is

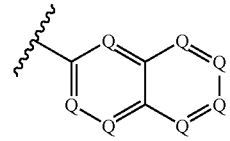

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, in any one ring, each Q may be 1, 2, or 3 nitrogen atoms. In a preferred embodiment, only one Q in each ring is nitrogen. In another preferred embodiment, only a single Q is nitrogen. Optionally, Q may be 1, 2, 3, 4, or 5 C—H. Optionally, 1, 2, 3, 4, or 5 Q may be C—$R^6$. In a particularly preferred embodiment, each $R^6$ is H.

Each $R^5$ is, independently, OH, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{11}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

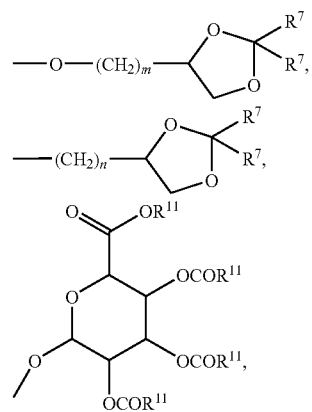

—$(CH_2)_n$—$CO_2R^{13}$, -Het-$(CH_2)_m$—$CO_2R^{13}$, —$(CH_2)_n$—$(Z)_g$—$CO_2R^{13}$, -Het-$(CH_2)_n$—$(Z)_g$—$CO_2R^{13}$, —$(CH_2)_n$—$NR^{10}$—$(CH_2)_m(CHOR^8)_n$—$CO_2R^{13}$, -Het-$(CH_2)_m$—$NR^{10}$—$(CH_2)_m(CHOR^8)_n$—$CO_2R^{13}$, —$(CH_2)_n$—$(CHOR^8)_m$—$CO_2R^{13}$, -Het-$(CH_2)_m$—$(CHOR^8)_m$—$CO_2R^{13}$, —$(CH_2)_n$—$(CHOR^8)_m(Z)_g$—$CO_2R^{13}$, -Het-$(CH_2)_n$—$(CHOR^8)_m$—$(Z)_g$—$CO_2R^{13}$, —$(CH_2)_n$—$(Z)_g$—$(CH_2)_n$—$CO_2R^{13}$, —$(CH_2)_n$—$(Z)_g$-$(CH_2)_m$—$CO_2R^{13}$, —$(CH_2)_n$—$(Z)_g(CHOR^8)_m$—$(Z)_g$—$CO_2R^{13}$, -Het-$(CH_2)_n$—$(Z)_g$—$(CHOR^8)_m$—$(Z)_g$—$CO_2R^{13}$, —$(CH_2)_n$—CONH—C(=$NR^{13}$)—$NR^{13}R^{13}$, -Het-$(CH_2)_n$—CO—NH—C(=$NR^{13}$)—$NR^{13}R^{13}$, —$(CH_2)_n$—$(Z)_g$—CONH—C(=$NR^{13}$)—$NR^{13}R^{13}$, -Het-$(CH_2)_n$—$(Z)_g$—CONH—C(=$NR^{13}$)—$NR^{13}R^{13}$, —$(CH_2)_n$—$NR^{10}$—$(CH_2)_m$(CHOR^8)_n$—CONH—C(=$NR^{13}$)—$NR^{13}R^{13}$, -Het-$(CH_2)_n$—$NR^{10}$—$(CH_2)_m(CHOR^8)_n$—CONH—C(=$NR^{13}$)—$NR^{13}R^{13}$, —$(CH_2)_n$—$(CHOR^8)_m$—CONH—C $(=NR^{13})-NR^{13}R^{13}$, $-Het-(CH_2)_n-(CHOR^8)_m-CONH-C(=NR^{13})-NR^{13}R^{13}$, $-(CH_2)_n-(Z)_g-CONH-C(=NR^{13})-NR^{13}R^{13}$, $-(CH_2)_n-(CHOR^8)_m-(Z)_g-CONH-C(=NR^{13})-NR^{13}R^{13}$, $-(CH_2)_n-(Z)_g-(CH_2)_mCONH-C(=NR^{13})-NR^{13}R^{13}$, $-Het-(CH_2)_n-(Z)_g-(CH_2)_mCONH-C(=NR^{13})-NR^{13}R^{13}$, $-(CH_2)_n-(Z)_g-(CHOR^8)_m-(Z)_g-CONH-C(=NR^{13})-NR^{13}R^{13}$, $Het-(CH_2)_n-(Z)_g-(CHOR^8)_m-(Z)_g-CONH-C(=NR^{13})-NR^{13}R^{13}$, $-(CH_2)_n-CONR^7-CONR^{13}R^{13}$, $-Het-(CH_2)_n-CONR^7-CONR^{13}R^{13}$, $-(CH_2)_n-(Z)_g-CONR^7-CONR^{13}R^{13}$, $-(CH_2)_n-(Z)_g-CONR^7-CONR^{13}R^{13}$, $-(CH_2)_n-NR^{10})(CH_2)_m(CHOR^8)_m-CONR^7-CONR^{13}R^{13}$, $-Het-(CH_2)_n-NR^{10}-(CH_2)_m-(CHOR^8)_n-CONR^7-CONR^{13}R^{13}$, $-(CH_2)_n-(CHOR^8)_m-CONR^7-CONR^{13}R^{13}$, $Het-(CH_2)_n-(CHOR^8)_m-CONR^7-CONR^{13}R^{13}$, $-(CH_2)-(CHOR^8)_m-(Z)_g-CONR^7-CONR^{13}R^{13}$, $-Het-(CH_2)_n-(CHOR^8)_m-(Z)_g-CNR^7-CONR^{13}R^{13}$, $-(CH_2)_n-(Z)_g-(CH_2)_mCONR^7-CONR^{13}R^{13}$, $-Het-(CH_2)_n-(Z)_g-(CH_2)_mCONR^7-CONR^{13}R^{13}$, $-(CH_2)_n-(Z)_g(CHOR^8)_m-(Z)_g-CONR^7-CONR^{13}R^{13}$, $-Het-(CH_2)_n-(Z)_g(CHOR^8)_m-(Z)_g$ $CONR^7-CONR^{13}R^{13}$, $-(CH_2)_n-CONR^7SO_2NR^{13}R^{13}$, $-Het-(CH_2)_m-CONR^7SO_2NR^{13}R^{13}$, $-(CH_2)_n-(Z)_gCONR^7SO_2NR^{13}R^{13}$, $-Het-(CH_2)_m-(Z)_n-CONR^7SO_2NR^{13}R^{13}$, $-(CH_2)_n-NR^{10}-(CH_2)_m(CHOR^8)_n-CONR^7SO_2NR^{13}R^{13}$, $-Het-(CH_2)_m-NR^{10}-(CH_2)_m(CHOR^8)_n-CONR^7SO_2NR^{13}R^{13}$, $-(CH_2)_n-(CHOR^8)_m-CONR^7SO_2NR^{13}R^{13}$, $-Het-(CH_2)_m-(CHOR^8)_m-CONR^7SO_2NR^{13}R^{13}$, $-(CH_2)_m(CHOR^8)_m-(Z)_g-CONR^7SO_2NR^{13}R^{13}$, $-Het-(CH_2)_n-(CHOR^8)_m-(Z)_gCONR^7SO_2NR^{13}R^{13}$, $-(CH_2)_m-(Z)_g-(CH_2)_mCONR^7SO_2NR^{13}R^{13}$, $-Het-(CH_2)_n-(Z)_g-(CH_2)_nCONR^7SO_2NR^{13}R^{13}$, $-(CH_2)_n-(Z)_g-(CHOR^8)_m-(Z)_g-CONR^7SO_2NR^{13}R^{13}$, $-Het-(CH_2)_n-(Z)_g-(CHOR^8)_m-(Z)_g-CONR^7SO_2NR^{13}R^{13}$, $-(CH_2)_n-SO_2NR^{13}R^{13}$, $-Het-(CH_2)_m-SO_2NR^{13}R^{13}$, $-(CH_2)_n-(Z)_g-SO_2NR^{13}R^{13}$, $-Het-(CH_2)_m-(Z)_g-SO_2NR^{13}R^{13}$, $-(CH_2)_n-NR^{10}-(CH_2)_m(CHOR^8)_n-SO_2NR^{13}R^{13}$, $-Het-(CH_2)_m-NR^{10}-(CH_2)_m(CHOR^8))_n-SO_2NR^{13}R^{13}$, $-(CH_2)_n-(CHOR^8)_m-SO_2NR^{13}R^{13}$, $-Het-(CH_2)_m-(CHOR^8)_m-SO_2NR^{13}R^{13}$, $-(CH_2)_n-(CHOR^8)_m-(Z)_g-SO_2NR^{13}R^{13}$, $-Het-(CH_2)_n-(CHOR^8)_m-(Z)_n-(Z)_g-SO_2NR^{13}R^{13}$, $-(CH_2)_n-(Z)_g-(CH_2)_mSO_2NR^{13}R^{13}$, $-Het-(CH_2)_n-(Z)_g-(CH_2)_m-SO_2NR^{13}R^{13}$, $-(CH_2)_n-(Z)_g-(CHOR^8)_m-(Z)_g-SO_2NR^{13}R^{13}$, $-Het-(CH_2)_n-(Z)_g-(CHOR^8)_m-(Z)_g-SO_2NR^{13}R^{13}$, $-(CH_2)_n-CONR^{13}R^{13}$, $-Het-(CH_2)_m-CONR^{13}SR^{13}$, $-(CH_2)_n-(Z)_g-CONR^{13}R^{13}$, $-Het-(CH_2)_m-(Z)_g-CONR^{13}R^{13}$, $-(CH_2)_n-NR^{10}-(CH_2)_m(CHOR^8)_n-CONR^{13}R^{13}$, $-Het-(C_{1-2})_m-NR^{10}-(CH_2)_m(CHOR^8)_n-CONR^{13}R^{13}$, $-(CH_2)_n-(CHOR^8)_m-CONR^{13}R^{13}$, $-Het-(CH_2)_m-NR^{10}-(CH_2)_m(CHOR^8)_n-CONR^{13}R^{13}$, $-(CH_2)_n-(CHOR^8)_m-(Z)_g-CONR^{13}R^{13}$, $-Het-(CH_2)_n-(CHOR^8)_m-(Z)_g-CONR^{13}R^{13}$, $-(CH_2)_n-(Z)_g-(CH_2)_mCONR^{13}R^{13}$, $-Het-(CH_2)_n-(Z)_g-(CH_2)_mCONR^{13}R^{13}$, $-(CH_2)_n-(Z)_g-(CHOR^8)_m-(Z)_gOCONR^{13}R^{13}$, $-Het-(CH_2)_n-(Z)_g-(CHOR^8)_m-(Z)_g-CONR^{13}R^{13}$, $-(CH_2)_n-CONR^7COR^{13}$, $-Het-(CH_2)_m-CONR^7COR^{13}$, $-(CH_2)_n-(Z)_g-CONR^7COR^{13}$, $-Het-(CH_2)_m-(Z)_g-CONR^7COR^{13}$, $-(CH_2)_n-NR^{10}-(CH_2)_m-(CHOR^8)_m-CONR^7COR^{13}$, $-Het-(CH_2)_m-NR^{10}-(CH_2)_m(CHOR^8)_n-CONR^7COR^{13}$, $-(CH_2)_n-(CHOR^8)_m-CONR^7COR^{13}$, $-Het-(CH_2)_m-(CHOR^8)_m-CONR^7COR^{13}$, $-(CH_2)_n-(CHOR^8)_m-(Z)_g-CONR^7COR^{13}$, $-Het-(CH_2)_m-(CHOR^8)_m-(Z)_g-CONR^7COR^{13}$, $-(CH_2)_n-(Z)_g-(CH_2)_mCONR^7COR^{13}$, $-Het-(CH_2)_n-(Z)_g-(CH_2)_mCONR^7COR^{13}$, $-(CH_2)_n-(Z)_g-(CHOR^8)_m-(Z)_g-CONR^7COR^{13}$, $-Het-(CH_2)_n-(Z)_g-(CHOR^8)_m-(Z)_g-CONR^7CO_2R^{13}$, $-Het-(CH_2)_m-(Z)_g-CONR^7CO_2R^{13}$, $-(CH_2)_n-NR^{10}-(CH_2)_m(CHOR^8)_m-CONR^7CO_2R^{13}$, $-Het-(CH_2)_m-NR^{10}-(CH_2)_m(CHOR^8)_n-CONR^7CO_2R^{13}$, $-(CH_2)_n-(CHOR^8)_m-CONR^7CO_2R^{13}$, $-Het-(CH_2)_m-(CHOR^8)_m-CONR^7CO_2R^{13}$, $-(CH_2)_n-(CHOR^8)_m-(Z)_g-CONR^7CO_2R^{13}$, $-Het-(CH_2)_n-(CHOR^8)_m-(Z)_g-CONR^7CO_2R^{13}$, $-(CH_2)_n-(Z)_g-(CH_2)_mCONR^7CO_2R^{13}$, $-Het-(CH_2)_n-(Z)_g-(CH_2)_mCONR^7CO_2R^{13}$, $-(CH_2)_n-(Z)_g-(CHOR^8)_m-(Z)_g-CONR^7CO_2R^{13}$, $-Het-(CH_2)_n-(Z)_g-(CHOR^8)_m-(Z)_g-CONR^7CO_2R^{13}$, $-(CH_2)_n-NH-C(=NR^{13})-NR^{13}R^{13}$, $-Het-(CH_2)_m-NH-C(=NR^{13})-NR^{13}R^{13}$, $-(CH_2)_n-(Z)_g-NH-C(=NR^{13})-NR^{13}R^{13}$, $-Het-(CH_2)_n-(Z)_g-NH-C(=NR^{13})-NR^{13}R^{13}$, $-(CH_2)_n-NR^{10}-(CH_2)_m(CHOR^8)_n-NH-C(=NR^{13})-NR^{13}R^{13}$, $-Het-(CH_2)_n-NR^{10}-(CH_2)_m(CHOR^8)_n-NH-C(=NR^{13})-NR^{13}R^{13}$, $-(CH_2)_n-(CHOR^8)_m-NH-C(=NR^{13})-NR^{13}R^{13}$, $-Het-(CH_2)_m-(CHOR^8)_m-NH-C(=NR^{13})-NR^{13}R^{13}$, $-(CH_2)_n-(CHOR^8)_m-(Z)_g-NH-C(=NR^{13})-NR^{13}R^{13}$, $-Het-(CH_2)_n-(CHOR^8)_m-(Z)_g-(CH_2)_mNH-C(=NR^{13})-NR^{13}R^{13}$, $-Het-(CH_2)_n-(Z)_g-(CH_2)_mNH-C(=NR^{13})-NR^{13}R^{13}$, $-(CH_2)_n-(Z)_g-(CHOR^8)_m-(Z)_g-NH-C(=NR^{13})-NR^{13}R^{13}$, $-Het-(CH_2)_n-(Z)_g-(CHOR^8)_m-(Z)_g-NH-C(=NR^{13})-NR^{13}R^{13}$, $-(CH_2)_n-C(=NR^{13})-NR^{13}R^{13}$, $Het-(CH_2)_m-C(=NH)-NR^{13}R^{13}$, $-(CH_2)_n-(Z)_g-C(=NH)-NR^{13}R^{13}$, $Het-(CH_2)_m-(Z)_g-C(=NH)-NR^{13}R^{13}$, $-(CH_2)_n-NR^{10}-(CH_2)_n-(CHOR^8)_m-C(=NR^{13})-NR^{13}R^{13}$, $Het-(CH_2)_n-NR^{10}-(CH_2)_m(CHOR^8)_n-C(=NR^{13})-NR^{13}R^{13}$, $-Het-(CH_2)_m-(CHOR^8)_m-C(=NR^{13})-NR^{13}R^{13}$, $-(CH_2)_n-(CHOR^8)_m-(Z)_g-C(=NR^{13})-NR^{13}R^{13}$, $-Het-(CH_2)_n-(CHOR^8)_m-(Z)_g-C(=NR^{13})-NR^{13}R^{13}$, $-(CH_2)_n-(Z)_g-(CH_2)_n-C(=NHC(=NR^{13})-NR^{13}R^{13}$, $Het-(CH_2)_n-(Z)_g-(CH_2)_m-C(=NR^{13})-NR^{13}R^{13}$, $-(CH_2)_n-(Z)_g-(CHOR^8)_m-(Z)_g-C(=NR^{13})-NR^{13}R^{13}$, $-Het-(CH_2)_n-(Z)_g-(CHOR^8)_m-(Z)_g-C(=NR^{13})-NR^{13}R^{13}$, $-(CH_2)_n-NR^{12}R^{12}$, $-O-(CH_2)_m-NR^{12}R^{12}$, $-O-(CH_2)_n-NR^{12}R^{12}$, $-O-(CH_2)_m(Z)_gR^{12}$, $-(CH_2)_nNR^{11}R^{11}$, $-O-(CH_2)_mNR^{11}R^{11}$, $-(CH_2)_n-N^{\oplus}-(R^{11})_3$, $-O-(CH_2)_m-N^{\oplus}-(R^{11})_3$, $-(CH_2)_n-(Z)_g-(CH_2)_m-NR^{10}R^{10}$, $-O-(CH_2)_m-(Z)_g-(CH_2)_m-NR^{10}R^{10}$, $-(CH_2CH_2O)_m-CH_2CH_2NR^{12}R^{12}$, $-O-(CH_2CH_2O)_m-CH_2CH_2NR^{12}R^{12}$, $-(CH_2)_n-(C=O)NR^{12}R^{12}$, $-O-(CH_2)_m-(C=O)NR^{12}R^{12}$, $-(CHOR^8)_mCH_2NR^{10}-(Z)_g-R^{10}$, $-(CH_2)_n-(CHOR^8)_mCH_2-NR^{10}-(Z)_g-R^{10}$, $-(CH_2)_nNR^{10}-O(CH_2)_m(CHOR^8)_nCH_2NR^{10}-(Z)_g-R^{10}$, $-O(CH_2)_m-NR^{10}-(CH_2)_m-(CHOR^8)_nCH_2NR^{10}-(Z)_g-R^{10}$, $-(Het)-(CH_2)_m-OR^8$, $-(Het)-(CH_2)_m-NR^7R^{10}$, $-(Het)-(CH_2)_m(CHOR^8)(CHOR^8)_n-CH_2OR^8$, $-(Het)-(CH_2CH_2O)_m-R^8$, $-(Het)-(CH_2CH_2O)_m-CH_2CH_2NR^7R^{10}$, $-(Het)-(CH_2)_m-C(=O)NR^7R^{10}$, $-(Het)-(CH_2)_m-(Z)_g-R^7$, $-(Het)-(CH_2)_m-NR^{10}-CH_2(CHOR^8)(CHOR^8)_n-CH_2OR^8$, $-(Het)-(CH_2)_m-CO_2R^7$, $-(Het)-(CH_2)_m-NR^{12}R^{12}$, $-(Het)-(CH_2)_n-NR^{12}R^{12}$, $-(Het)-(CH_2)_m-(Z)_gR^{12}$, $-(Het)-(CH_2)_mNR^{11}R^{11}$, $-(Het)-(CH_2)_m-N^{\oplus}-(R^{11})_3$, $-(Het)-(CH_2)_m-(Z)_g-(CH_2)_m-NR^{10}R^{10}$, $-(Het)-CH_2CH_2O)_m-CH_2CH_2NR^{12}R^{12}$, $-(Het)-(CH_2)_m-(CHOR^8)_mCH_2NR^{10}-(Z)_g-R^{10}$, $-(Het)-(CH_2)_n-(C=O)NR^{12}R^{12}$, $-(Het)-(CH_2)_m-(CHOR^8)_mCH_2NR^{10}-(Z)_g-R^{10}$, $-(Het)-(CH_2)_n-(CHOR^8)_nCH_2NR^{10}-(Z)_g-R^{10}$, $-(CH_2)_n-(CHOR^8)(CHOR^8)_n-CH_2OR^8$, $-O-(CH_2)_n-(CHOR^8)(CHOR^8)_n-CH_2OR^8$, $-(CH_2)_n-NR^{10}-CH_2(CHOR^8)(CHOR^8)_n-CH_2OR^8$, —O—(CH$_2$)$_n$—NR$^{10}$—CH$_2$(CHOR$^8$)(CHOR$^8$)$_n$—CH$_2$OR$^8$, Link-(CH$_2$)$_n$-CAP, Link-(CH$_2$)$_n$(CHOR$^8$)(CHOR$^8$)$_n$-CAP, Link-(CH$_2$CH$_2$O)$_m$—CH$_2$-CAP, Link-(CH$_2$CH$_2$O)$_m$—CH$_2$CH$_2$-CAP, Link-(CH$_2$)$_n$—(Z)$_g$-CAP, Link-(CH$_2$)$_n$(Z)$_g$—(CH$_2$)$_m$-CAP, Link-(CH$_2$)$_n$—NR$^{13}$—CH$_2$(CHOR$^8$)(CHOR$^8$)$_n$-CAP, Link-(CH$_2$)$_n$—(CHOR$^8$)$_m$CH$_2$—NR$^{13}$—(Z)$_g$-CAP, Link-(CH$_2$)$_n$NR$^{13}$—(CH$_2$)$_m$(CHOR$^8$)$_n$CH$_2$NR$^{13}$—(Z)$_g$-CAP, -Link-(CH$_2$)$_m$—(Z)$_g$—(CH$_2$)$_m$-CAP, Link-NH—C(O)—NH—(CH$_2$)$_m$-CAP, Link (CH$_2$)$_n$-CAP, Link-(CH$_2$)$_n$—C(=O)NR$^{13}$—(CH$_2$)$_m$—C(=O)NR$^{10}$R$^{10}$, Link-(CH$_2$)$_m$—C(=O)NR$^{13}$—(CH$_2$)$_m$-CAP, Link-(CH$_2$)$_m$—C(=O)NR$^{11}$R$^{11}$, Link-(CH$_2$)$_m$—C(=O)NR$^{12}$R$^{12}$, Link-(CH$_2$)$_n$—(Z)$_g$—(CH$_2$)$_m$—(Z)$_g$-CAP, Link-(Z)$_g$—(CH$_2$)$_m$-Het-(CH$_2$)$_m$-CAP, Link-(CH$_2$)$_n$—CR$^{11}$R$^{11}$-CAP, Link-(CH$_2$)$_n$(CHOR$^8$)(CHOR$^8$)$_n$CR$^{11}$R$^{11}$-CAP, Link-(CH$_2$CH$_2$O)$_m$—CH$_2$—CR$^{11}$R$^{11}$-CAP, Link-(CH$_2$CH$_2$O)$_m$—CH$_2$CH$_2$—CR$^{11}$R$^{11}$CAP, Link-(CH$_2$)$_n$—(Z)$_g$—CR$^{11}$R$^{11}$-CAP, Link-(CH$_2$)$_n$(Z)$_g$—(CH$_2$)$_m$—CR$^{11}$R$^{11}$-CAP, Link-(CH$_2$)$_n$—NR$^{13}$—CH$_2$(CHOR$^8$)(CHOR$^8$))$_n$—CR$^{11}$R$^{11}$-CAP, Link-(CH$_2$)$_n$—(CHOR$^8$)$_m$CH$_2$—NR$^{13}$—(Z)$_g$—CR$^{11}$R$^{11}$-CAP, Link-(CH$_2$)$_n$NR$^{13}$—(CH$_2$)$_m$(CHOR$^8$)$_n$CH$_2$NR$^{13}$—(Z)$_g$—CR$^{11}$R$^{11}$-CAP, Link-(CH$_2$)$_m$—(Z)$_g$-(CH$_2$)$_m$—CR$^{11}$R$^{11}$-CAP, Link NH—C(=O)—NH—(CH$_2$)$_m$—CR$^{11}$R$^{11}$-CAP, Link (CH$_2$)$_m$—C(=O)NR$^{13}$—(CH$_2$)$_m$—CR$^{11}$R$^{11}$-CAP, Link-(CH$_2$)$_n$—(Z)$_g$—(CH$_2$)$_m$—(Z)$_g$—CR$^{11}$R$^{11}$-CAP, or Link-(Z)$_g$—(CH$_2$)$_m$-Het-(CH$_2$)$_m$—CR$^{11}$R$^{11}$-CAP.

In a preferred embodiment, R$^5$ is —OH, —O—(CH$_2$)$_m$(Z)$_g$R$^{12}$, -Het-(CH$_2$), —NH—C(=NR$^{13}$)—NR$^{13}$R$^{13}$, -Het-(CH$_2$)$_n$—(Z)$_g$—(CH$_2$)$_m$NH—C(=NR$^{13}$)—NR$^{13}$R$^{13}$, -Link-(CH$_2$)$_m$—(Z)$_g$-(CH$_2$)$_m$-CAP, -Het-(CH$_2$)$_m$—CONR$^{13}$R$^{13}$, —(CH$_2$)$_n$—NR$^{12}$R$^{12}$, —O—(CH$_2$)$_m$NR$^{11}$R$^{11}$, O—(CH$_2$)$_m$—N$^{⊕}$—(R$^{11}$)$_3$, —(CH$_2$)$_n$—(Z)$_g$—(CH$_2$)$_m$—NR$^{10}$R$^{10}$, -Het-(CH$_2$)$_n$—(Z)$_g$—NH—C(=NR$^{13}$)—NR$^{13}$R$^{13}$, —O—(CH$_2$)$_m$(CHOR$^8$)(CHOR$^8$)$_n$—CH$_2$OR$^8$, —O—(CH$_2$)$_m$—C(=O)NR$^7$R$^{10}$, —O—(CH$_2$)$_m$—(Z)$_g$—R$^7$, or —O—(CH$_2$)$_n$—NR$^{10}$—CH$_2$(CHOR$^8$)(CHOR$^8$)$_n$—CH$_2$OR$^8$.

In another preferred embodiment R$^5$ is one of the following:
—(CH$_2$)$_m$—OR$^8$, —(CH$_2$)$_4$—OH, —O—(CH$_2$)$_n$—OR$^8$, —O—(CH$_2$)$_4$—OH, —(CH$_2$)$_n$—NR$^7$R$^{10}$, —NHSO$_2$CH$_3$, —CH$_2$NH(C=O)—(OCH$_3$)$_3$, —NH(C=O)CH$_3$, —CH$_2$NH$_2$, —NH—CO$_2$C$_2$H$_5$, —CH$_2$NH(C=O)CH$_3$, —CH$_2$NHCO$_2$CH$_3$, —CH$_2$NHSO$_2$CH$_3$, —(CH$_2$)$_4$—NH(C=O)O(CH$_3$)$_3$, —(CH$_2$)$_4$—NH$_2$, —(CH$_2$)$_3$—NH(C=O)O(CH$_3$)$_3$, —(CH$_2$)$_3$—NH$_2$, —O—(CH$_2$)$_m$—NR$^7$R$^{10}$, —OCH$_2$CH$_2$NHCO$_2$(CH$_3$)$_3$, —OCH$_2$CH$_2$NHCO$_2$C$_2$H$_5$, —O—(CH$_2$)$_3$—NH—CO$_2$—(CH$_3$)$_3$, —O(CH$_2$)$_3$—NH$_2$, —OCH$_2$CH$_2$NHSO$_2$CH$_3$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —OCH$_2$CHOHCH$_2$O-glucuronide, —OCH$_2$CH$_2$CHOHCH$_2$OH, —OCH$_2$—(α-CHOH)$_2$CH$_2$OH, —OCH$_2$—(CHOH)$_2$CH$_2$OH, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —C(=O)NH$_2$, —O—(CH$_2$)$_m$—C(=O)NR$^7$R$^{10}$, —O—CH$_2$—(C=O)NHCH$_2$CHOH, —O—CH$_2$—(C=O)NHCH$_2$CHOHCH$_2$OH, —O—CH$_2$(C=O)NHCH$_2$(CHOH)$_2$CH$_2$OH, —O—CH$_2$C(=O)NHSO$_2$CH$_3$, —O—CH$_2$C(=O)NHCO$_2$CH$_3$, —O—CH$_2$—C(=O)NH—C(=O)NH$_2$, —O—CH$_2$—(C=O)NH—(C=O)CH$_3$, —(CH$_2$)$_n$—(Z)$_g$—R$^7$, —(CH$_2$)$_n$—(C=N)—NH$_2$, —(C=NH)NH$_2$, —(CH$_2$)$_n$—NH—C(=NH)—NH$_2$, —(CH$_2$)$_3$—NH—C(=NH)—NH$_2$, —CH$_2$NH—C(=NH)—NH$_2$, —(CH$_2$)$_n$—CONHCH$_2$(CHOH)$_n$—CH$_2$OH, —NH—C(=O)—CH$_2$—(CHOH)$_n$CH$_2$OH, —NH—(C=O)—NH—CH$_2$(CHOH)$_2$CHOH, —NHC(C=O)NHCH$_2$CH$_2$OH, —O—(CH$_2$)$_m$—(Z)$_g$—R$^7$, —O—(CH$_2$)$_m$—NH—C(=NH)—N(R$^7$)$_2$, —O(CH$_2$)$_3$—NH—C(=NH)—NH$_2$, —O—(CH$_2$)$_m$—CHNH$_2$—CO$_2$NR$^7$R$^{10}$, —OCH$_2$—CHNH$_2$—CO$_2$NH$_2$, —O—(CH$_2$)$_m$—CHNH$_2$—CO$_2$NR$^7$R$^{10}$ (anomeric center is the (R) enantiomer), —O—(CH$_2$)$_m$—CHNH$_2$—CO$_2$NR$^7$R$^{10}$ (anomeric center is the (S) enantiomer), —OCH$_2$CHOH—CH$_2$NHCO$_2$(CH$_3$)$_3$, —(CH$_2$)$_n$—NR$^{10}$—CH$_2$(CHOR$^8$)(CHOR$^8$)$_n$—CH$_2$OR$^8$, —NHCH$_2$(CHOH)$_2$CH$_2$OH, —O—(CH$_2$)$_m$—NR$^{10}$—CH$_2$(CHOR$^8$)(CHOR$^8$)$_n$—CH$_2$OR$^8$, —O—(CH$_2$)$_m$—CO$_2$R$^7$, —OCH$_2$CH$_2$CO$_2$(CH$_3$)$_3$, —OCH$_2$CO$_2$H, —OCH$_2$CO$_2$C$_2$H$_5$, —O—(CH$_2$)$_m$-Boc, —(CH$_2$)$_m$-Boc, —O—(CH$_2$)$_m$—NH—C(=NH)—N(R$^7$)$_2$, —(CH$_2$)$_n$—NH—C(=NH)—N(R$^7$)$_2$, —(CH$_2$)$_m$—NH—C(=O)—OR$^7$, —O—(CH$_2$)$_n$—NH—C(=O)—OR$^7$—(CH$_2$)$_n$—NH—C(=O)—R$^{11}$, —O—(CH$_2$)$_m$—NH—C(=O)—R$^{11}$, —O—(CH$_2$)$_m$—C(=O)N(R$^7$)$_2$, —(CH$_2$)$_m$—CHOH—CH$_2$—NH-Boc, —O—(CH$_2$)$_m$—CHOH—CH$_2$—NHBoc, —(CH$_2$)$_m$—NHC(O)OR$^7$, —O—(CH$_2$)$_m$—NHC(O)OR$^7$, —O—(CH$_2$)$_m$—C(=NH)—N(R$^7$)$_2$, or —(CH$_2$)$_n$—C(=NH)—N(R$^7$)$_2$.

In another embodiment, R$^5$ is selected from the group consisting of —O—(CH$_2$)$_3$—OH, —NH$_2$, —O—CH$_2$—(CHOH)$_2$—CH$_2$OH, —O—CH$_2$—CHOH—CH$_2$OH, —O—CH$_2$CH$_2$—O-tetrahydropyran-2-yl, —O—CH$_2$CHOH—CH$_2$—O-glucuronide, —O—CH$_2$CH$_2$OH, —O—(CH$_2$CH$_2$O)$_4$—CH$_3$, —O—CH$_2$CH$_2$OCH$_3$, —O—CH$_2$—(CHOC(=O)CH$_3$)—CH$_2$—OC(=O)CH$_3$, —O—(CH$_2$CH$_2$O)$_2$—CH$_3$, —OCH$_2$—CHOH—CHOH—CH$_2$OH, —CH$_2$OH, —CO$_2$CH$_3$,

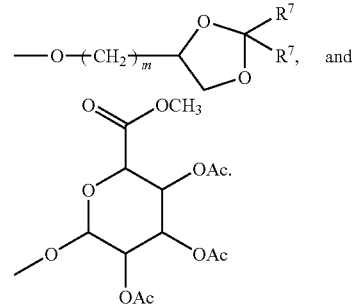

In another embodiment, R$^5$ is selected from the group consisting of —O—(CH$_2$)$_3$—OH, —NH$_2$, —O—CH$_2$—(CHOH)$_2$—CH$_2$OH, —O—CH$_2$—CHOH—CH$_2$OH, —O—CH$_2$CH$_2$—O-tetrahydropyran-2-yl, —O—CH$_2$CHOH—CH$_2$—O-glucuronide, —O—CH$_2$CH$_2$OH, —O—(CH$_2$CH$_2$O)$_4$—CH$_3$, —O—CH$_2$CH$_2$OCH$_3$, —O—CH$_2$—(CHOC(=O)CH$_3$)—CH$_2$—OC(=O)CH$_3$, —O—(CH$_2$CH$_2$O)$_2$—CH$_3$, —OCH$_2$—CHOH—CHOH—CH$_2$OH, —CH$_2$OH, —CO$_2$CH$_3$, —SO$_3$H, —O-glucuronide,

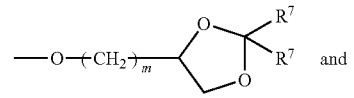

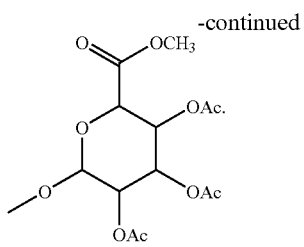

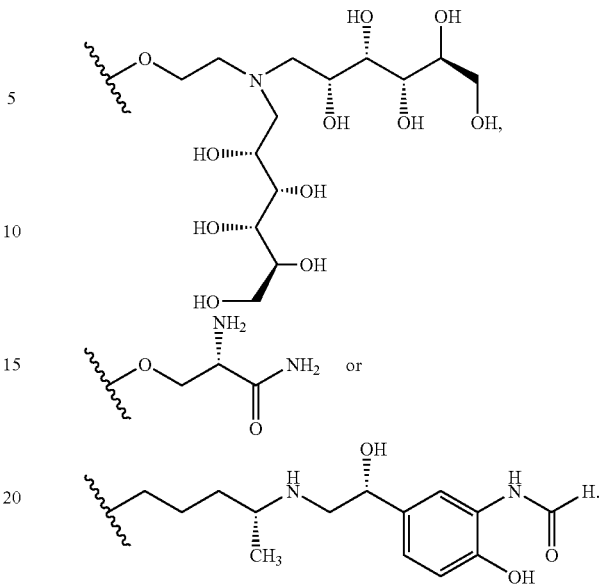

In a preferred embodiment, each —(CH$_2$)$_n$—(Z)$_g$—R$^7$ falls within the scope of the structures described above and is, independently, —(CH$_2$)$_n$—(C=N)—NH$_2$, —(CH$_2$)$_n$—NH—C(=NH)NH$_2$, —(CH$_2$)$_n$—CONHCH$_2$(CHOH)$_n$—CH$_2$OH, or —NH—C(=O)—CH$_2$—(CHOH)$_n$CH$_2$OH.

In another a preferred embodiment, each —O—(CH$_2$)$_m$—(Z)$_g$—R$^7$ falls within the scope of the structures described above and is, independently, —O—(CH$_2$)$_m$—NH—C(=NH)—N(R$^7$)$_2$, or —O—(CH$_2$)$_m$—CHNH$_2$—CO$_2$NR$^7$R$^{10}$.

In another preferred embodiment, R$^5$ may be one of the following: —O—CH$_2$CHOHCH$_2$O-glucuronide, —OCH$_2$CHOHCH$_3$, —OCH$_2$CH$_2$NH$_2$, —OCH$_2$CH$_2$NHCO(CH$_3$)$_3$, —CH$_2$CH$_2$OH, —OCH$_2$CH$_2$OH, —O—(CH$_2$)$_m$-Boc, —(CH$_2$)$_m$-Boc, —OCH$_2$CH$_2$OH, —OCH$_2$CO$_2$H, —O—(CH$_2$)$_m$—NH—C(=NH)—N(R$^7$)$_2$, —(CH$_2$)$_m$—NH—C(=NH)—N(R$^7$)$_2$, —NHCH$_2$(CHOH)$_2$—CH$_2$OH, —OCH$_2$CO$_2$Et, —NHSO$_2$CH$_3$, —(CH$_2$)$_n$—NH—C(=O)—OR$^7$, —O—(CH$_2$)., —NH—C(=O)—OR$^7$, —(CH$_2$)$_n$—NH—C(=O)—R$^{11}$, —O—(CH$_2$)$_m$—NH—C(=O)—R$^{11}$, —O—CH$_2$C(=O)NH$_2$, —CH$_2$NH$_2$, —NHCO$_2$Et, —OCH$_2$CH$_2$CH$_2$OH, —CH$_2$NHSO$_2$CH$_3$, —OCH$_2$CH$_2$CHOHCH$_2$OH, —OCH$_2$CH$_2$NHCO$_2$Et, —NH—C(=NH2)-NH$_2$, —OCH$_2$-(α-CHOH)$_2$—CH$_2$OH, —OCH$_2$CHOHCH$_2$NH$_2$, —(CH$_2$)$_n$—CHOH—CH$_2$—NH-Boc, —O—(CH$_2$)$_m$—CHOH—CH$_2$—NHBoc, —(CH$_2$)$_m$—NHC(O)OR$^7$, —O—(CH$_2$)$_m$—NHC(O)OR$^7$, —OCH$_2$CH$_2$CH$_2$NH$_2$, —OCH$_2$CH$_2$NHCH$_2$(CHOH)$_2$CH$_2$OH, —OCH$_2$CH$_2$NH(CH$_2$[(CHOH)$_2$CH$_2$OH])$_2$, —(CH$_2$)$_4$—NHBoc, —(CH$_2$)$_4$—NH$_2$, —(CH$_2$)$_4$—OH, —OCH$_2$CH$_2$NHSO$_2$CH$_3$, —O—(CH$_2$)$_m$—C(=NH)—N(R$^7$)$_2$, —(CH$_2$)$_m$—C(=NH)—N(R$^7$)$_2$, —(CH$_2$)$_3$—NH Boc, —(CH$_2$)$_3$NH$_2$, —O—(CH$_2$)$_m$—NH—NH—C(=NH)—N(R$^7$)$_2$, —(CH$_2$)$_n$—NH—NH—C(=NH)—N(R$^7$)$_2$, or —O—CH$_2$—CHOH—CH$_2$—NH—C(=NH)—N(R$^7$)$_2$.

In another preferred embodiment, R$^5$ is —OH, O—(CH$_2$)$_m$(Z)$_g$R$^{12}$, -Het-(CH$_2$), —NH—C(=NR$^{13}$)—NR$^{13}$R$^{13}$, -Het-(CH$_2$)$_n$—(Z)$_g$—(CH$_2$)$_m$NH—C(=NR$^{13}$)—NR$^{13}$R$^{13}$, -Link-(CH$_2$)$_m$—(Z)$_g$-(CH$_2$)$_m$-CAP, Link-(CH$_2$)$_n$—CR$^{11}$R$^{11}$-CAP, -Het-(CH$_2$)$_m$—CONR$^{13}$R$^{13}$, —(CH$_2$)$_n$—NR$^{12}$R$^{12}$, —O—(CH$_2$)$_m$NR$^{11}$R$^{11}$, —O—(CH$_2$)$_m$—N$^⊕$—(R$^{11}$)$_3$, —(CH$_2$)$_n$—(Z)$_g$—(CH$_2$)$_n$—NR$^{10}$R$^{10}$, -Het-(CH$_2$)$_n$—(Z)$_g$—NH—C(=NR$^{13}$)—NR$^{13}$R$^{13}$, —O—(CH$_2$)$_m$(CHOR$^8$)(CHOR$^8$)$_n$—CH$_2$OR$^8$, —O—(CH$_2$)$_m$—C(=O)NR$^7$R$^{10}$, —O—(CH$_2$)$_m$—(Z)$_g$—R$^7$, or —O—(CH$_2$)$_m$—NR$^{10}$—CH$_2$(CHOR$^8$)(CHOR$^8$)$_n$—CH$_2$OR$^8$.

In a particularly preferred embodiment, R$^5$ is —O—CH$_2$—(CHOH)—CH$_2$OH, —OH, —O—(CH$_2$)$_3$NH$_2$, —O—(CH$_2$)$_3$NH(C=NH)NH$_2$, —O—(CH$_2$)$_2$NH(C=NH)NH$_2$, —O—CH$_2$(CO)NH$_2$, —O—(CH$_2$)$_2$—N$^⊕$—(CH$_3$)$_3$, Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, R$^9$ contains a R$^{13}$ substituent. R$^{13}$ can contain an R$^{10}$ substituent and R$^{10}$ can contain a R$^9$ substituent. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, R$^9$, R$^{13}$ and R$^{10}$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, R$^9$ will occur 0 to 8 times in a given embodiment, R$^{13}$ will occur 0 to 6 times in a given embodiment and R$^{10}$ will occur 0 to 6 times in a given embodiment. Even more typically yet, R$^9$ will occur 0 to 6 times in a given embodiment, R$^{13}$ will occur 0 to 4 times in a given embodiment and R$^{10}$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Each -Het- is, independently, —N(R$^7$)—, —N(R$^{10}$)—, —S—, —SO—, —SO$_2$—; —O—, —SO$_2$NH—, —NHSO$_2$—, —NR$^7$CO—, —CONR$^7$—, —N(R$^{13}$)—, —SO$_2$NR$^{13}$—, —NR$^{13}$CO—, or —CONR$^{13}$—. In a preferred embodiment, -Het- is —O—, —N(R$^7$)—, or —N(R$^{10}$)—. Most preferably, -Het- is —O—.

Each -Link- is, independently, —O—, —(CH$_2$)$_n$—, —O(CH$_2$)$_m$—, —NR$^{13}$—C(=O)—NR$^{13}$—, —NR$^{13}$—C(=O)—(CH$_2$)$_m$—, —C(=O)NR$^{13}$—(CH$_2$)$_m$—, —(CH$_2$)$_n$—

$(Z)_g$—$(CH_2)_n^-$, —S—, —SO—, —SO$_2$—, —SO$_2$NR$^{10}$—, or -Het-. In a preferred embodiment, -Link- is —O—, —(CH$_2$)$_n$—, —NR$^{13}$—C(=O)—(CH$_2$)$_m$—, or —C(=O)NR$^{13}$—(CH$_2$)$_m^-$.

Each -CAP is, independently, thiazolidinedione, oxazolidinedione, -heteroaryl-C(=O)NR$^{13}$R$^{13}$, heteroaryl-W, —CN, —O—C(=S)NR$^{13}$R$^{13}$, —(Z)$_g$R$^{13}$, —CR$^{10}$((Z)$_g$R$^{13}$)((Z)$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)—(Z)$_g$—R$^{13}$, a cyclic sugar or oligosaccharide, a cyclic amino sugar, oligosaccharide, —CR$^{10}$(—(CH$_2$)$_m$—R$^9$)(—(CH$_2$)$_m$—R$^9$), —N(—(CH$_2$)$_m$—R$^9$)(—(CH$_2$)$_m$—R$^9$), —NR$^{13}$(—(CH$_2$)$_m$—CO$_2$R$^{13}$),

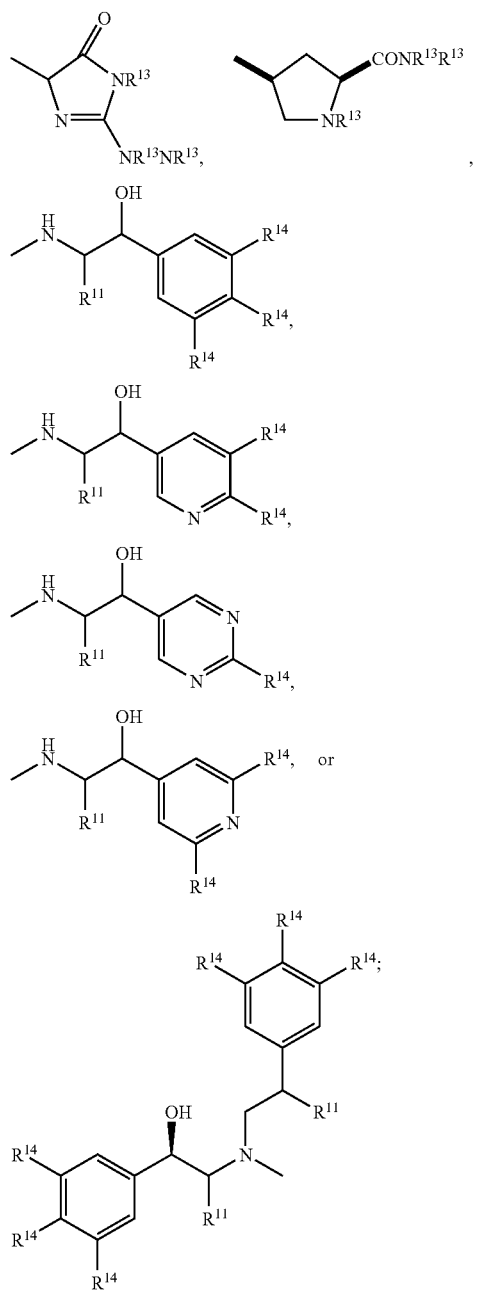

In a preferred embodiment, CAP is

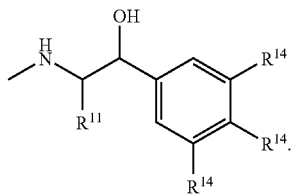

Each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl.

Examples of heteroaryl include pyridinyl, pyrazinyl, furanyl, thienyl, tetrazolyl, thiazolidinedionyl, imidazoyl, pyrrolyl, quinolinyl, indolyl, adeninyl, pyrazolyl, thiazolyl, isoxazolyl, benzimidazolyl, purinyl, isoquinolinyl, pyridazinyl, pyrimidinyl, 1,2,3-triazinyl, 1,2,4-triazinyl, 1,3,5-triazinyl, cinnolinyl, phthalazinyl, quinazolinyl, quinoxalinyl, and pterdinyl groups.

Each W is, independently, thiazolidinedione, oxazolidinedione, heteroaryl-C(=O)N R$^{13}$R$^{13}$, —CN, —O—C(=S)NR$^{13}$R$^{13}$, —(Z)$_g$R$^{13}$, —CR$^{10}$((Z)$_g$R$^{13}$)((Z)$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)—(Z)$_g$—R$^{13}$, a cyclic sugar or oligosaccharide, a cyclic amino sugar, oligosaccharide,

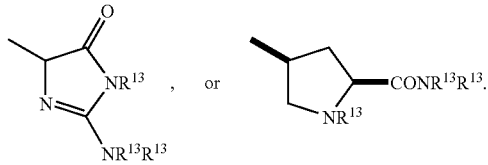

There is at least one R$^5$ on A$^1$ and A$^2$ and the remaining substituents are R$^6$. Each R$^6$ is, independently, R$^5$, —R$^7$, —OR$^{11}$, —N(R$^7$)$_2$, —(CH$_2$)$_m$—OR$^8$, —O—(CH$_2$)$_m$—OR$^8$, —(CH$_2$)$_m$—NR$^7$R$^{10}$, —O—(CH$_2$)$_m$—NR$^7$R$^{10}$, —(CH$_2$)$_m$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$), —(CH$_2$)$_n$—C(=O)NR$^7$R$^{10}$, —O—(CH$_2$)$_n$—C(=O)NR$^7$R$^{10}$, —(CH$_2$)$_n$—(Z)$_g$—R$^7$, —O—(CH$_2$)$_n$—(Z)$_g$—R$^7$, —(CH$_2$)$_n$NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

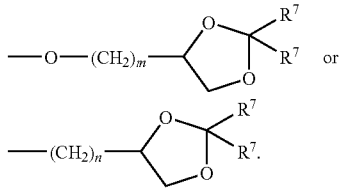

When two R$^6$ are —OR$^{11}$ and are located adjacent to each other on the aromatic carbocycle or aromatic heterocycle, the two OR$^{11}$ may form a methylenedioxy group; i.e., a group of the formula —O—CH$_2$—O—.

In addition, one or more of the $R^6$ groups can be one of the $R^5$ groups which fall within the broad definition of $R^6$ set forth above.

$R^6$ may be hydrogen. Therefore, provided that the aromatic carbocycle or aromatic heterocycle is substituted with $R^5$, the remaining $R^6$ may be hydrogen. Preferably, at most, 3 of the $R^6$ groups are other than hydrogen. More preferably, provided that the aromatic carbocycle or aromatic heterocycle is substituted with $R^5$, then $R^6$ is H.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—. As designated by (Z)$_g$ in certain embodiments, Z may occur one, two, three, four, five or six times and each occurance of Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—. Therefore, by way of example and not by way of limitation, (Z)$_g$ can be —(CHOH)—(CHNR$^7$R$^{10}$)—, —(CHOH)—(CHNR$^7$R$^{10}$)—C(=O)—, —(CHOH)—(CHNR$^7$R$^{10}$)—C(=O)—(CH$_2$)$_n$—, —(CHOH)—(CHNR$^7$R$^{10}$)—C(=O)—(CH$_2$)$_n$—(CHNR$^{13}$R$^{13}$)—, —(CHOH)—(CHNR$^7$R$^{10}$)—C(=O)—(CH$_2$)$_n$—(CHNR$^{13}$R$^{13}$)—C(=O)—, and the like.

In any variable containing —CHOR$^8$— or —CH$_2$OR$^8$ groups, when any —CHOR$^8$— or —CH$_2$OR$^8$ groups are located 1,2- or 1,3- with respect to each other, the $R^8$ groups may, optionally, be taken together to form a cyclic mono- or di-substituted 1,3-dioxane or 1,3-dioxolane.

More specific examples of suitable compounds represented by formula (I) are shown in formulas II and III below wherein $A^1$ and $A^2$ are defined as above:

formula II

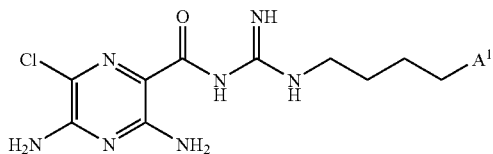

formula III

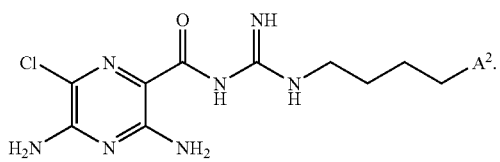

In a preferred aspect of formula II, $A^1$ is selected from indenyl, napthalenyl, 1,2-dihydronapthalenyl, 1,2,3,4-tetrahydronapthalenyl, anthracenyl, fluorenyl, phenanthrenyl, azulenyl, cyclohepta-1,3,5-trienyl or 5H-dibenzo[a,d]cycloheptenyl.

In another preferred aspect of formula II, $A^1$ is

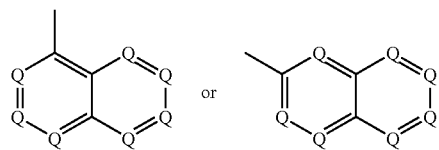

wherein each Q is, independently, C—H, C—R$^5$, or C—R$^6$, with the proviso that at least one Q is C—R$^5$. Preferably, six Q are C—H. Preferably, each $R^6$ is H. Preferably, $R^5$ is —OH, —O—(CH$_2$)$_m$(Z)$_g$R$^{12}$, -Het-(CH$_2$)$_m$—NH—C(=NR$^{13}$)—NR$^{13}$R$^{13}$, -Het-(CH$_2$)$_n$—(Z)$_g$—(CH$_2$)$_m$NH—C(=NR$^{13}$)—NR$^{13}$R$^{13}$, -Link-(CH$_2$)$_m$—(Z)$_g$—(CH$_2$)$_m$-CAP, Link-(CH$_2$)$_n$—CR$^{11}$R$^{11}$-CAP, -Het-(CH$_2$)$_m$—CONR$^{13}$R$^{13}$, —(CH$_2$)$_n$—NR$^{12}$R$^{12}$, —O—(CH$_2$)$_m$NR$^{11}$R$^{11}$, —O—(CH$_2$)$_m$—N$^⊕$—(R$^{11}$)$_3$, —(CH$_2$)$_n$—(Z)$_g$—(CH$_2$)$_n$—NR$^{10}$R$^{10}$, -Het-(CH$_2$)$_n$—(Z)$_g$—NH—C(=NR$^{13}$)—NR$^{13}$R$^{13}$, —O—(CH$_2$)$_m$(CHOR$^8$)(CHOR$^8$)$_n$—CH$_2$OR$^8$, —O—(CH$_2$)$_m$—C(=O)NR$^7$R$^{10}$, —O—(CH$_2$)$_n$—(Z)$_g$—R$^7$, or —O—(CH$_2$)$_n$—NR$^{10}$—CH$_2$(CHOR$^8$)(CHOR$^8$)$_n$—CH$_2$OR$^8$. More preferably, six Q are C—H and $R^5$ is —OH, —O—(CH$_2$)$_m$(Z)$_g$R$^2$, -Het-(CH$_2$)$_m$—NH—C(=NR$^{13}$)—NR$^{13}$R$^{13}$, -Het-(CH$_2$)$_n$—(Z)$_g$—(CH$_2$)$_m$NH—C(=NR$^{13}$)—NR$^{13}$R$^{13}$, -Link-(CH$_2$)$_n$—(Z)$_g$—(CH$_2$)$_m$-CAP, Link-(CH$_2$)$_n$—CR$^{11}$R$^{11}$-CAP, -Het-(CH$_2$)$^m$—CONR$^{13}$R$^{13}$, —(CH$_2$)$_n$—NR$^{12}$R$^{12}$, —O—(CH$_2$)$_m$NR$^{11}$R$^{11}$, —O—(CH$_2$)$_m$—N$^⊕$-(R$^{11}$)$_3$, —(CH$_2$)$_n$—(Z)$_g$—(CH$_2$)$_m$—NR$^{10}$R$^{10}$, -Het-(CH$_2$)$_m$—(Z)$_g$—NH—C(=NR$^{13}$)—NR$^{13}$R$^{13}$, —O—(CH$_2$)$_m$(CHOR$^8$)(CHOR$^8$)$_n$—CH$_2$OR$^8$, —O—(CH$_2$)$_m$—C(=O)NR$^7$R$^{10}$, —O—(CH$_2$)$_m$—(Z)$_g$—R$^7$, or —O—(CH$_2$)$_m$—NR$^{10}$—CH$_2$(CHOR$^8$)(CHOR$^8$)$_n$—CH$_2$OR$^8$. More preferably, $R^5$ is —O—CH$_2$—(CHOH)—CH$_2$OH, —OH, —O—(CH$_2$)$_3$NH$_2$, —O—(CH$_2$)$_3$NH(C=NH)NH$_2$, —O—(CH$_2$)$_2$NH(C=NH)NH$_2$, —O—CH$_2$(CO)NH$_2$, —O—(CH$_2$)$_2$—N$^⊕$—(CH$_3$)$_3$,

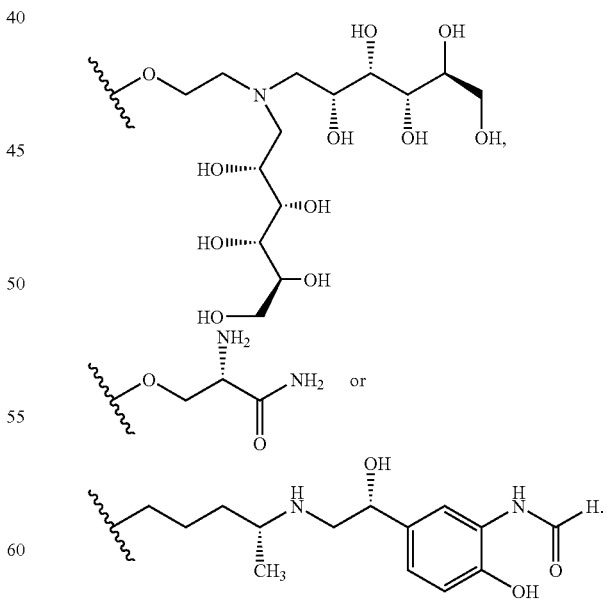

Most preferably, $R^5$—O—CH$_2$—(CHOH)—CH$_2$OH, —OH, —O—(CH$_2$)$_3$NH$_2$, —O—(CH$_2$)$_3$NH(C=NH)NH$_2$, —O—(CH$_2$)$_2$NH(C=NH)NH$_2$, —O—CH$_2$(CO)NH$_2$, —O—(CH$_2$)$_2$—N$^⊕$—(CH$_3$)$_3$,

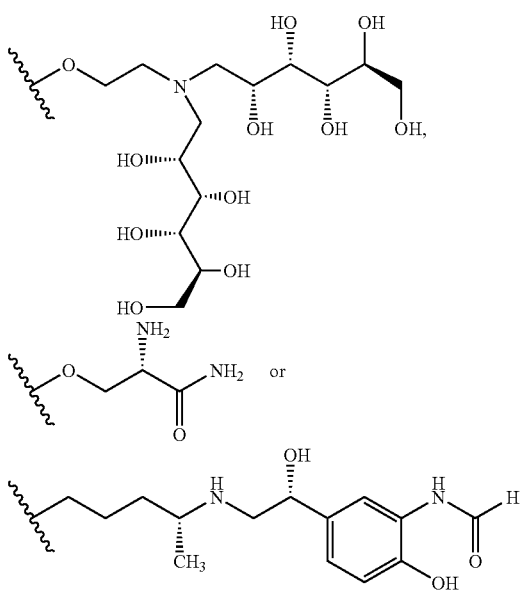

and six Q are C—H.

In another preferred aspect of formula II, $A^1$ is

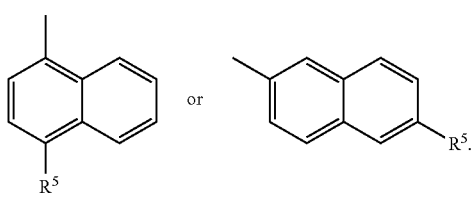

Preferably, $R^5$ is —OH, —O—$(CH_2)_m(Z)_gR^{12}$, -Het-$(CH_2)_m$—NH—C(=$NR^{13}$)—$NR^{13}R^{13}$, -Het-$(CH_2)_n$—$(Z)_g$—$(CH_2)_m$NH—C(=$NR^{13}$)—$NR^{13}R^{13}$, -Link-$(CH_2)_m$—$(Z)_g$—$(CH_2)_m$-CAP, Link-$(CH_2)_n$—$CR^{11}R^{11}$-CAP, -Het-$(CH_2)_m$—$CONR^{13}R^{13}$, —$(CH_2)_n$—$NR^{12}R^{12}$, —O—$(CH_2)_m$$NR^{11}R^{11}$, —O—$(CH_2)_m$—$N^{\oplus}$—$(R^{11})_3$, —$(CH_2)_n$—$(Z)_g$—$(CH_2)_m$—$NR^{10}R^{10}$, -Het-$(CH_2)_m$—$(Z)_g$—NH—C(=$NR^{13}$)—$NR^{13}R^{13}$, —O—$(CH_2)_m$(CHOR$^8$)(CHOR$^8$)$_n$—CH$_2$OR$^8$, —O—$(CH_2)_m$—C(=O)$NR^7R^{10}$, —O—$(CH_2)_m$—$(Z)_g$—$R^7$, or —O—$(CH_2)_m$—$NR^{10}$—CH$_2$(CHOR$^8$)(CHOR$^8$)$_n$—CH$_2$OR$^8$. Most preferably, $R^5$ is —O—CH$_2$—(CHOH)—CH$_2$OH, —OH, —O—(CH$_2$)$_3$NH$_2$, —O—(CH$_2$)$_3$ NH(C=NH)NH$_2$, —O—(CH$_2$)$_2$NH(C=NH)NH$_2$, —O—CH$_2$(CO)NH$_2$, —O—(CH$_2$)$_2$—$N^{\oplus}$—(CH$_3$)$_3$,

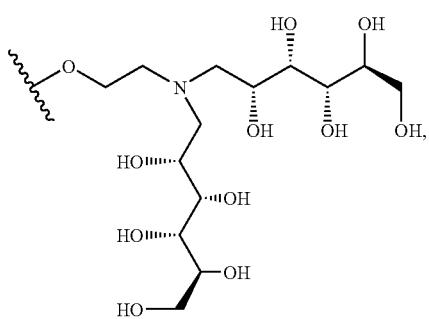

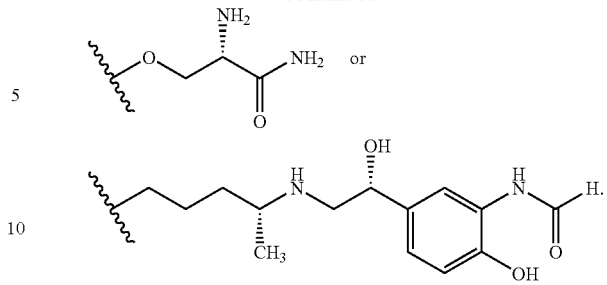

In a preferred aspect of formula III, $A^2$ is selected from indolizinyl, indolyl, isoindolyl, indolinyl, benzo[b]furanyl, 2,3-dihydrobenzo[b]furanyl, benzo[b]thiophenyl, 2,3-dihydrobenzo[b]thiophenyl, indazolyl, benzimidazolyl, benzthiazolyl, purinyl, quinolinyl, 1,2,3,4-tetrahydroquinolinyl, 3,4-dihydro-2H-chromenyl, 3,4-dihydro-2H-thiochromenyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, dibenzofuranyl, dibenzothiophenyl, 1H-azepinyl, 5H-dibenz[b,f]azepinyl, or 10,11-dihydro-5H-dibenz[b,f]azepinyl.

In another preferred aspect of formula III, $A^2$ is

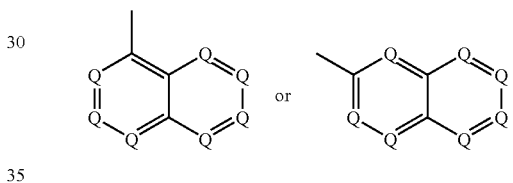

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. In a preferred embodiment, only one Q in each ring is nitrogen. In another preferred embodiment, only a single Q is nitrogen. In a particularly preferred embodiment, a single Q is nitrogen, one Q is C—$R^5$, and the remaining Q are C—H. In another preferred embodiment, each $R^6$ is H. Preferably, $R^5$ is —OH, —O—$(CH_2)_m(Z)_gR^{12}$, -Het-$(CH_2)_m$—NH—C(=$NR^{13}$)—$NR^{13}R^{13}$, -Het-$(CH_2)_n$—$(Z)_g$—$(CH_2)_m$NH—C(=$NR^{13}$)—$NR^{13}R^{13}$, -Link-$(CH_2)_n$—$(Z)_g$—$(CH_2)_n$-CAP, Link-$(CH_2)_n$—$CR^{11}R^{11}$-CAP, -Het-$(CH_2)_m$—$CONR^{13}R^{13}$, —$(CH_2)_n$—$NR^{12}R^{12}$, —O—$(CH_2)_m$$NR^{11}R^{11}$, —O—$(CH_2)_m$—$N^{\oplus}$—$(R^{11})_3$, —$(CH_2)_n$—$(Z)_g$—$(CH_2)_m$—$NR^{13}R^{13}$, -Het-$(CH_2)_n$—$(Z)_g$—NH—C(=$NR^{13}$)—$NR^{13}R^{13}$, —O—$(CH_2)_m$(CHOR$^8$)(CHOR$^8$)$_n$—CH$_2$OR$^8$, —O—$(CH_2)_m$—C(=O)$NR^7R^{10}$, —O—$(CH_2)_m$—$(Z)_g$—$R^7$, or —O—$(CH_2)_m$—$NR^{10}$—CH$_2$(CHOR$^8$)(CHOR$^8$)$_n$—CH$_2$OR$^8$. More preferably, one Q is nitrogen, five Q are C—H and $R^5$ is —OH, —O—$(CH_2)_m(Z)_gR^{12}$, -Het-$(CH_2)_m$—NH—C(=$NR^{13}$)—$NR^{13}R^{13}$, -Het-$(CH_2)_n$—$(Z)_g$—$(CH_2)_m$NH—C(=$NR^{13}$)—$NR^{13}R^{13}$, -Link-$(CH_2)_m$—$(Z)_g$—$(CH_2)_m$-CAP, Link-$(CH_2)_n$—$CR^{11}R^{11}$-CAP, -Het-$(CH_2)_m$—$CONR^{13}R^{13}$, —$(CH_2)_n$—$NR^{12}R^{12}$, —O—$(CH_2)_m$$NR^{11}R^{11}$, —O—$(CH_2)_m$—$N^{\oplus}$—$(R^{11})_3$, —$(CH_2)_n$—$(Z)_g$—$(CH_2)_m$—$NR^{10}R^{10}$, -Het-$(CH_2)_n$—$(Z)_g$—NH—C(=$NR^{13}$)—$NR^{13}R^{13}$, —O—$(CH_2)_m$(CHOR$^8$)(CHOR$^8$)$_n$—CH$_2$OR$^8$, —O—$(CH_2)_m$—C(=O)$NR^7R^{10}$, —O—$(CH_2)_m$—$(Z)_g$—$R^7$, or —O—$(CH_2)_m$—$NR^{10}$—CH$_2$(CHOR$^8$)(CHOR$^8$)$_n$—CH$_2$OR$^8$. More preferably, $R^5$ is

33

—O—CH$_2$—(CHOH)—CH$_2$OH, —OH, —O—(CH$_2$)$_3$NH$_2$, —O—(CH$_2$)$_3$NH(C=NH)NH$_2$, —O—(CH$_2$)$_2$NH(C=NH)NH$_2$, —O—CH$_2$(CO)NH$_2$, —O—(CH$_2$)$_2$—N$^\oplus$—(CH$_3$)$_3$,

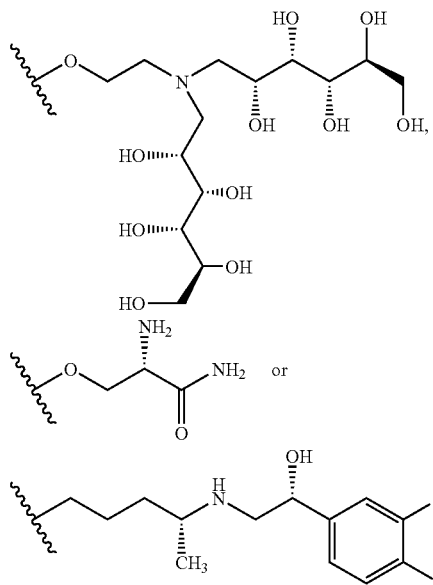

Most preferably, R$^5$ is —O—CH$_2$—(CHOH)—CH$_2$OH, —OH, —O—(CH$_2$)$_3$NH$_2$, —O—(CH$_2$)$_3$NH(C=NH)NH$_2$,

34

—O—(CH$_2$)$_2$NH(C=NH)NH$_2$, —O—CH$_2$(CO)NH$_2$, —O—(CH$_2$)$_2$—N$^\oplus$—(CH$_3$)$_3$,

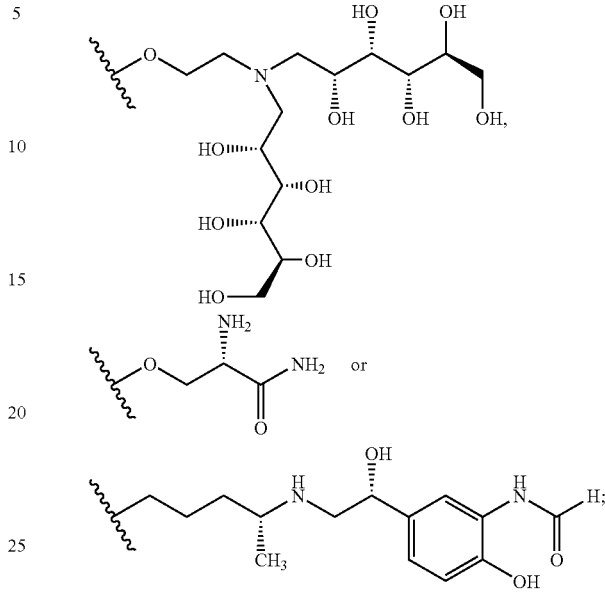

a single Q is nitrogen and five Q are C—H.

In a particularly preferred embodiment, the compounds of formula I, formula II, or formula III are:

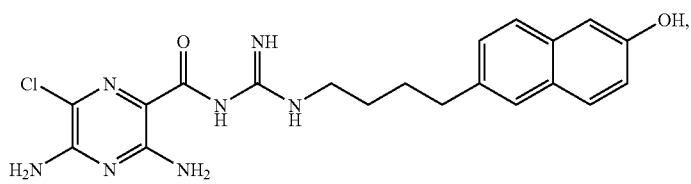

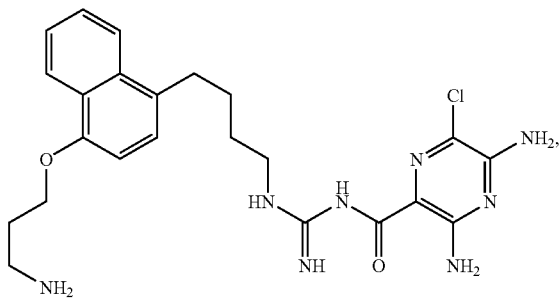

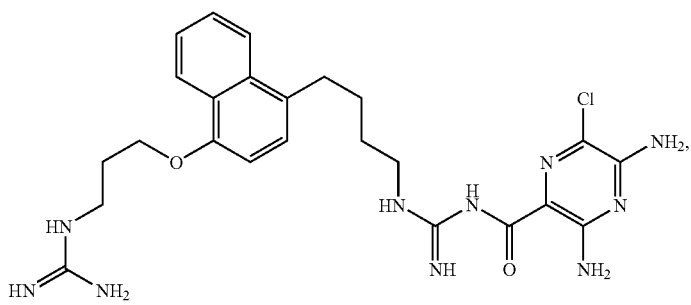

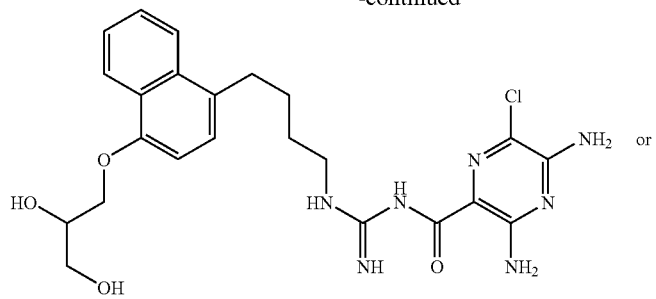
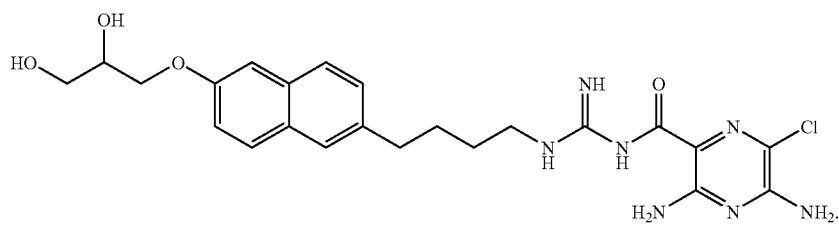
In another preferred embodiment, the compounds of the present invention are represented by the following formulas:
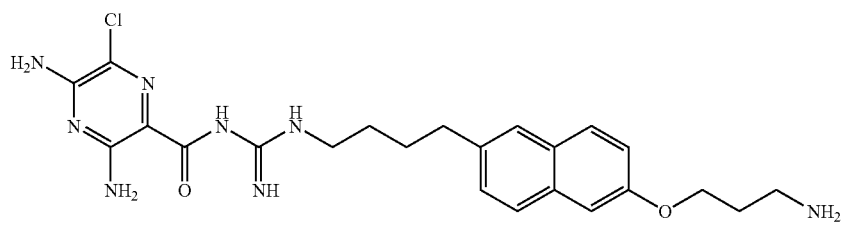
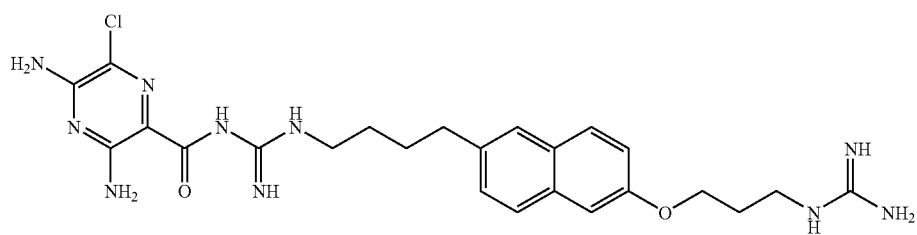
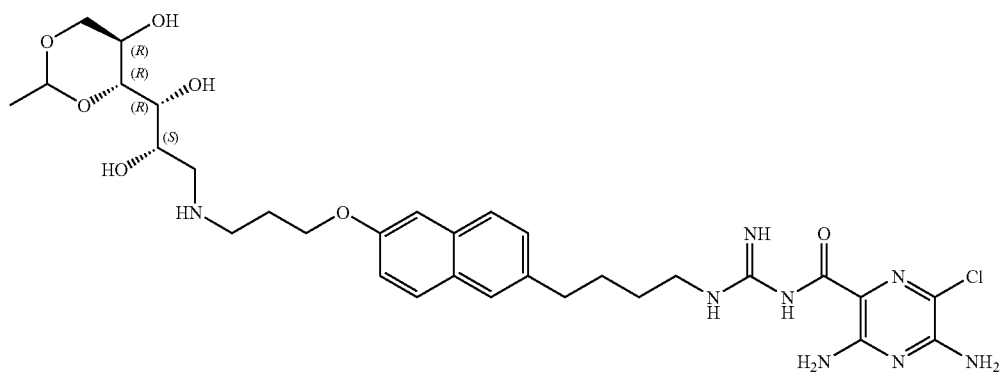

-continued

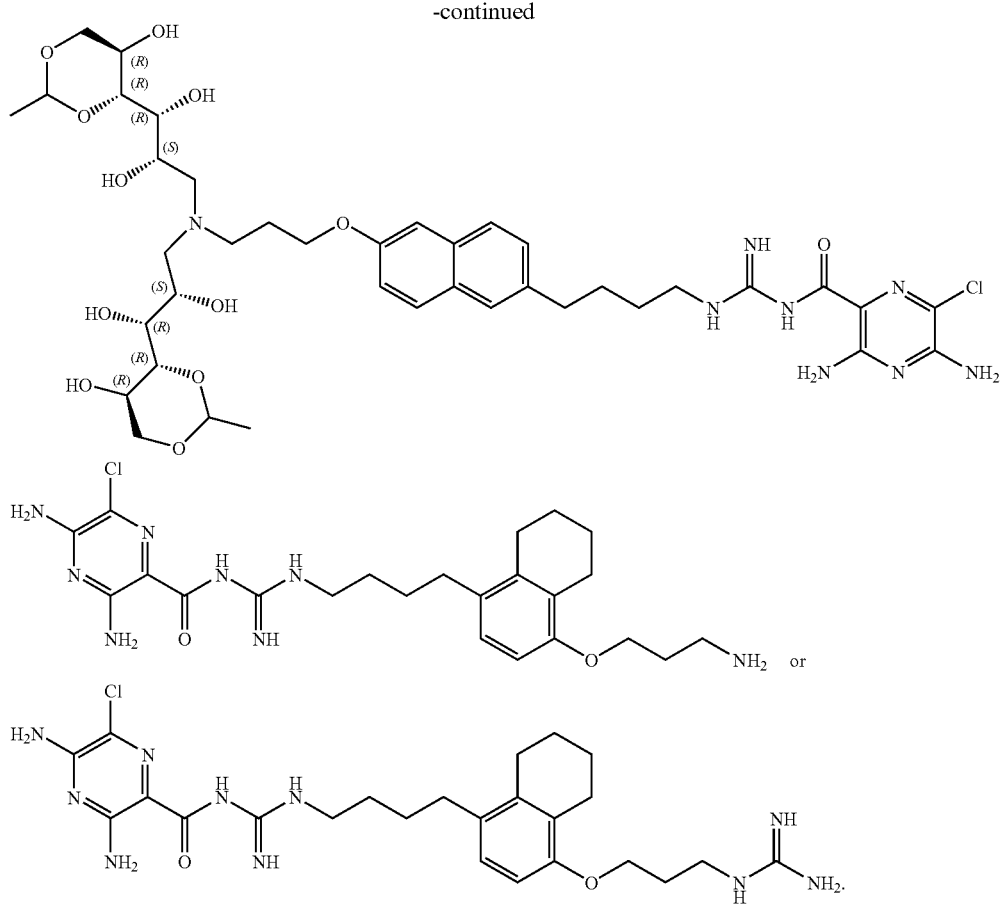

The compounds described herein may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures, tautomers, polymorphs, pseudopolymorphs and pharmaceutically acceptable salts of compounds within the scope of formula (I), formula II, or formula III are embraced by the present invention. All mixtures of such enantiomers and diastereomers are within the scope of the present invention.

A compound of formula I-III and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of formula I-III and their pharmaceutically acceptable salts.

A compound of formula I-III and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of formula I-III and their pharmaceutically acceptable salts.

The compounds of formula I-III may exist in different tautomeric forms. One skilled in the art will recognize that amidines, amides, guanidines, ureas, thioureas, heterocycles and the like can exist in tautomeric forms. By way of example and not by way of limitation, compounds of formula I-III can exist in various tautomeric forms as shown below:

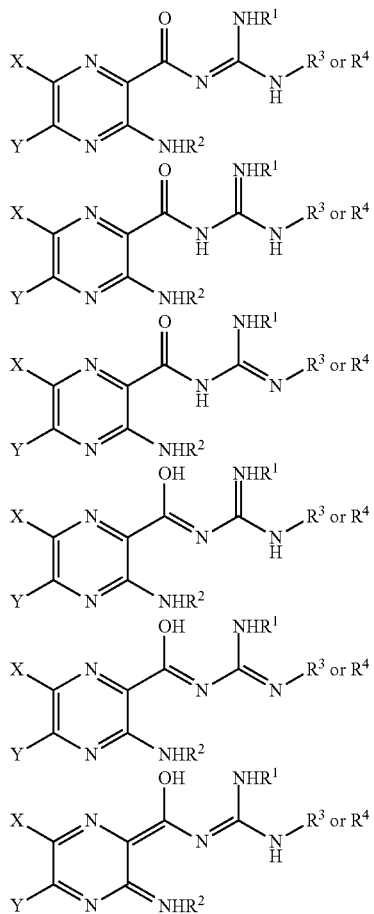

All possible tautomeric forms of the amidines, amides, guanidines, ureas, thioureas, heterocycles and the like of all of the embodiments of formula I-III are within the scope of the instant invention.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

Without being limited to any particular theory, it is believed that the compounds of formula (I), formula II, or formula III function in vivo as sodium channel blockers. By blocking epithelial sodium channels present in mucosal surfaces the compounds of formula (I), formula II, or formula III reduce the absorption of water by the mucosal surfaces. This effect increases the volume of protective liquids on mucosal surfaces, rebalances the system, and thus treats disease.

The present invention also provides methods of treatment that take advantage of the properties of the compounds described herein as discussed above. Thus, subjects that may be treated by the methods of the present invention include, but are not limited to, patients afflicted with cystic fibrosis, primary ciliary dyskinesia, chronic bronchitis, bronchiectasis chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., *staphylococcus* infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-sinal surfaces by topical delivery, including aerosols and drops.

The present invention may be used to hydrate mucosal surfaces other than airway surfaces. Such other mucosal surfaces include gastrointestinal surfaces, oral surfaces, genitourethral surfaces, ocular surfaces or surfaces of the eye, the inner ear and the middle ear. For example, the active compounds of the present invention may be administered by any suitable means, including locally/topically, orally, or rectally, in an effective amount.

The compounds of the present invention are also useful for treating a variety of functions relating to the cardiovascular system. Thus, the compounds of the present invention are useful for use as antihypertensive agents. The compounds may also be used to reduce blood pressure and to treat edema. In addition, the compounds of the present invention are also useful for promoting diuresis, natriuresis, and saluresis. The compounds may be used alone or in combination with beta blockers, ACE inhibitors, HMGCoA reductase inhibitors, calcium channel blockers and other cardiovascular agents to treat hypertension, congestive heart failure and reduce cardiovascular mortality.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I), formula II, or formula III in a pharmaceutically acceptable carrier (e.g., an aqueous carrier solution). In general, the compound of formula (I), formula II, or formula III is included in the composition in an amount effective to inhibit the reabsorption of water by mucosal surfaces.

Without being limited to any particular theory, it is believed that sodium channel blockers of the present invention block epithelial sodium channels present in mucosal surfaces the sodium channel blocker, described herein reduce the absorption of salt and water by the mucosal surfaces. This effect increases the volume of protective liquids on mucosal surfaces, rebalances the system, and thus treats disease. This effect is enhanced when used in combination with osmolytes.

The compounds of formula (I), formula II, or formula III may also be used in conjunction with osmolytes thus lowering the dose of the compound needed to hydrate mucosal surfaces. This important property means that the compound will have a lower tendency to cause undesired side-effects by blocking sodium channels located at untargeted locations in the body of the recipient, e.g., in the kidneys when used in combination with an osmolyte.

Active osmolytes of the present invention are molecules or compounds that are osmotically active (i.e., are "osmolytes"). "Osmotically active" compounds of the present invention are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Active compounds of the present invention may be ionic osmolytes (i.e., salts), or may be non-ionic osmolytes (i.e., sugars, sugar alcohols, and organic osmolytes). It is specifically intended that both racemic forms of the active compounds that are racemic in nature are included in the group of active compounds that are useful in the present invention. It is to be noted that all racemates, enantiomers, diastereomers, tautomers, polymorphs and pseudopolymorphs and racemic mixtures of the osmotically active compounds are embraced by the present invention.

Active osmolytes useful in the present invention that are ionic osmolytes include any salt of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., *Remington: The Science and Practice of Pharmacy, Vol. II*, pg. 1457 (19$^{th}$ Ed. 1995), incorporated herein by reference, and can be used in any combination including their conventional combinations.

Pharmaceutically acceptable osmotically active anions that can be used to carry out the present invention include, but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrate, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include chloride, sulfate, nitrate, gluconate, iodide, bicarbonate, bromide, and phosphate.

Pharmaceutically acceptable cations that can be used to carry out the present invention include, but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the present invention include but are not limited to aluminum, calcium, lithium, magnesium, potassium, sodium, zinc, iron, ammonium, and the like. Particularly preferred cations include sodium, potassium, choline, lithium, meglumine, D-lysine, ammonium, magnesium, and calcium.

Specific examples of osmotically active salts that may be used with the sodium channel blockers described herein to carry out the present invention include, but are not limited to, sodium chloride, potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, etc. Either a single salt or a combination of different osmotically active salts may be used to carry out the present invention. Combinations of different salts are preferred. When different salts are used, one of the anion or cation may be the same among the differing salts.

Osmotically active compounds of the present invention also include non-ionic osmolytes such as sugars, sugar-alcohols, and organic osmolytes. Sugars and sugar-alcohols useful in the practice of the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol useful in the present invention are also active compounds within the scope of the invention. For example, glucose, when reduced, becomes sorbitol; within the scope of the invention, sorbitol and other reduced forms of sugar/sugar alcohols (e.g., mannitol, dulcitol, arabitol) are accordingly active compounds of the present invention.

Osmotically active compounds of the present invention additionally include the family of non-ionic osmolytes termed "organic osmolytes." The term "organic osmolytes" is generally used to refer to molecules used to control intracellular osmolality in the kidney. See e.g., J. S. Handler et al., *Comp. Biochem. Physiol*, 117, 301-306 (1997); M. Burg, *Am. J. Physiol*. 268, F983-F996 (1995), each incorporated herein by reference. Although the inventor does not wish to be bound to any particular theory of the invention, it appears that these organic osmolytes are useful in controlling extracellular volume on the airway/pulmonary surface. Organic osmolytes useful as active compounds in the present invention include but are not limited to three major classes of compounds: polyols (polyhydric alcohols), methylamines, and amino acids. The polyol organic osmolytes considered useful in the practice of this invention include, but are not limited to, inositol, myo-inositol, and sorbitol. The methylamine organic osmolytes useful in the practice of the invention include, but are not limited to, choline, betaine, carnitine (L-, D- and DL forms), phosphorylcholine, lyso-phosphorylcholine, glycerophosphorylcholine, creatine, and creatine phosphate. The amino acid organic osmolytes of the invention include, but are not limited to, the D- and L-forms of glycine, alanine, glutamine, glutamate, aspartate, proline and taurine. Additional osmolytes useful in the practice of the invention include tihulose and sarcosine. Mammalian organic osmolytes are preferred, with human organic osmolytes being most preferred. However, certain organic osmolytes are of bacterial, yeast, and marine animal origin, and these compounds are also useful active compounds within the scope of the present invention.

Under certain circumstances, an osmolyte precursor may be administered to the subject; accordingly, these compounds are also useful in the practice of the invention. The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., *J. Med. Chem*. 19:113-117 (1976); Bodor, N. et al., *J. Pharm. Sci*. 67:1045-1050 (1978); Bodor, N. et al., *J. Med. Chem*. 26:313-318 (1983); Bodor, N. et al., *J. Pharm. Sci*. 75:29-35 (1986), each incorporated herein by reference.

In general, osmotically active compounds of the present invention (both ionic and non-ionic) that do not promote, or in fact deter or retard bacterial growth are preferred.

The compounds of formula (I), formula II, or formula III described herein and osmotically active compounds disclosed herein may be administered in any order and/or concurrently to mucosal surfaces such as the eye, the nose, and airway surfaces including the nasal passages, sinuses and lungs of a subject by any suitable means known in the art, such as by nose drops, mists, aerosols, continuous overnight nasal cannulation, etc. In one embodiment of the invention, the compounds of formula (I), formula II, or formula III and osmotically active compounds of the present invention are administered concurrently by transbronchoscopic lavage. In a preferred embodiment of the invention, the compounds of formula (I), formula II, or formula III and osmotically active compounds of the present invention are deposited on lung airway surfaces by administering by inhalation an respirable aerosol respirable particles comprised of the compounds of formula (I), formula II, or formula III and the osmotically active compounds, in which the compounds of formula (I), formula II, or formula III can precede or follow the independent delivery of an osmotically active compound within a sufficiently short time for their effects to be additive. The respirable particles may be liquid or solid. Numerous inhalers for administering aerosol particles to the lungs of a subject are known. In another preferred embodiment of the invention, the compounds of formula (I), formula II, or formula III and osmotically active compounds can be given concurrently as defined herein.

The compounds of formula (I), formula II, or formula III and osmotically active compounds of the present invention are administered sequentially (in any order) or concurrently to the subject in need thereof. As used herein, the term "concurrently" means sufficiently close in time to produce a combined effect (that is, concurrently may be simultaneously, or it may be two or more events occurring within a short time period before or after each other). Concurrently also embraces the delivery of the compounds of formula (I), formula II, or formula III and osmolytes as a mixture or solution of the two components as well as when delivered from two different nebulizers. An example of that would be the delivery of compound I in one nebulizer and hypertonic saline in a second nebulizer connected by a T-piece. When administered with other active agents, the active compounds of the present invention may function as a vehicle or carrier for the other active agent, or may simply be administered concurrently with the other active agent. The active compound of the present invention may be used as a dry or liquid vehicle for administering other active ingredients to airway surfaces.

Such other active agents may be administered for treating the disease or disorder for which they are intended, in their conventional manner and dosages, in combination with the active compounds of the present invention, which may be thought of as serving as a vehicle or carrier for the other active agent. Any such other active ingredient may be employed, particularly where hydration of the airway surfaces (i.e., the activity of the osmotically active compounds of the present invention) facilitates the activity of the other active ingredient (e.g., by facilitating or enhancing uptake of the active ingredient, by contributing to the mechanism of action of the other active ingredient, or by any other mechanisms). In a preferred embodiment of the invention, when the active compound of the present invention is administered concurrently with another active agent, the active compound of the present invention has an additive effect in relation to the other active agent; that is, the desired effect of the other active agent is enhanced by the concurrent administration of the active compounds of the present invention.

The compounds of formula (I), formula II, or formula III of the present invention are also useful for treating airborne infections. Examples of airborne infections include, for example, RSV. The compounds of formula (I), formula II, or formula III of the present invention are also useful for treating an anthrax infection. The present invention relates to the use of the compounds of formula (I), formula II, or formula III of the present invention for prophylactic, post-exposure prophylactic, preventive or therapeutic treatment against diseases or conditions caused by pathogens. In a preferred embodiment, the present invention relates to the use of the compounds of formula (I), formula II, or formula III for prophylactic, post-exposure prophylactic, preventive or therapeutic treatment against diseases or conditions caused by pathogens which may be used in bioterrorism.

In recent years, a variety of research programs and biodefense measures have been put into place to deal with concerns about the use of biological agents in acts of terrorism. These measures are intended to address concerns regarding bioterrorism or the use of microorganisms or biological toxins to kill people, spread fear, and disrupt society. For example, the National Institute of Allergy and Infectious Diseases (NIAID) has developed a Strategic Plan for Biodefense Research which outlines plans for addressing research needs in the broad area of bioterrorism and emerging and reemerging infectious diseases. According to the plan, the deliberate exposure of the civilian population of the United States to *Bacillus anthracis* spores revealed a gap in the nation's overall preparedness against bioterrorism. Moreover, the report details that these attacks uncovered an unmet need for tests to rapidly diagnose, vaccines and immunotherapies to prevent, and drugs and biologics to cure disease caused by agents of bioterrorism.

Much of the focus of the various research efforts has been directed to studying the biology of the pathogens identified as potentially dangerous as bioterrorism agents, studying the host response against such agents, developing vaccines against infectious diseases, evaluating the therapeutics currently available and under investigation against such agents, and developing diagnostics to identify signs and symptoms of threatening agents. Such efforts are laudable but, given the large number of pathogens which have been identified as potentially available for bioterrorism, these efforts have not yet been able to provide satisfactory responses for all possible bioterrorism threats. Additionally, many of the pathogens identified as potentially dangerous as agents of bioterrorism do not provide adequate economic incentives for the development of therapeutic or preventive measures by industry.

Moreover, even if preventive measures such as vaccines were available for each pathogen which may be used in bioterrorism, the cost of administering all such vaccines to the general population is prohibitive.

Until convenient and effective treatments are available against every bioterrorism threat, there exists a strong need for preventative, prophylactic or therapeutic treatments which can prevent or reduce the risk of infection from pathogenic agents.

The present invention provides such methods of prophylactic treatment. In one aspect, a prophylactic treatment method is provided comprising administering a prophylactically effective amount of the compounds of formula (I), formula II, or formula III to an individual in need of prophylactic treatment against infection from one or more airborne pathogens. A particular example of an airborne pathogen is anthrax.

In another aspect, a prophylactic treatment method is provided for reducing the risk of infection from an airborne pathogen which can cause a disease in a human, said method comprising administering an effective amount of the compounds of formula (I), formula II, or formula III to the lungs of the human who may be at risk of infection from the airborne pathogen but is asymptomatic for the disease, wherein the effective amount of a sodium channel blocker and osmolyte are sufficient to reduce the risk of infection in the human. A particular example of an airborne pathogen is anthrax.

In another aspect, a post-exposure prophylactic treatment or therapeutic treatment method is provided for treating infection from an airborne pathogen comprising administering an effective amount of the compounds of formula (I), formula II, or formula III to the lungs of an individual in need of such treatment against infection from an airborne pathogen. The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism. The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality. Particular examples of these pathogens are anthrax and plague. Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656,256, and U.S. Pat. No. 5,292,498, each of which is incorporated herein by reference.

Bronchodilators can also be used in combination with compounds of the present invention. These bronchodilators include, but are not limited to, β-adrenergic agonists including but not limited to epinephrine, isoproterenol, fenoterol, albuterol, terbutalin, pirbuterol, bitolterol, metaproterenol, iosetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 μm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by a suitable means know in the art, such as by nose drops, mists, etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, each of which is incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, each of which is incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, each of which is incorporated herein by reference. These apparatuses are particularly suitable as dry particle inhalers.

Aerosols of liquid particles comprising the active compound may be produced by any suitable means, such as with a pressure-driven aerosol nebulizer (L C Star) or an ultrasonic nebulizer (Pari eFlow). See, e.g., U.S. Pat. No. 4,501,729, which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insulator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insulator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^4$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, $10^{-7}$ to about $10^{-3}$, $10^{-2}$, or $10^{-1}$ moles/liter, and more preferably from about $10^{-7}$ to about $10^{-4}$ moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 ($19^{th}$ ed. 1995), incorporated herein by reference. Pharmaceutical formulations suitable for nasal administration may be prepared as described in U.S. Pat. Nos. 4,389,393 to Schor; 5,707,644 to Illum; 4,294,829 to Suzuki; and 4,835,142 to Suzuki, the disclosures of which are incorporated by reference herein in their entirety.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, both of which are incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol.

A suitable dispersant is lactose, which may be blended with the active agent in any suitable ratio (e.g., a 1 to 1 ratio by weight).

The compounds of formula I-III may be synthesized according to procedures known in the art. A representative synthetic procedure is shown in the scheme below:

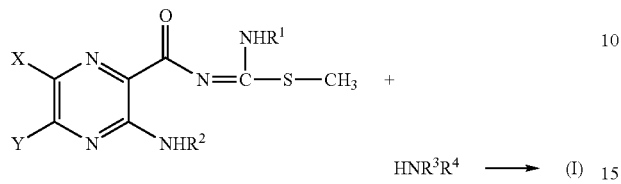

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Additional methods of preparing intermediates used in the preparation of compounds of the instant invention are disclosed in U.S. Pat. No. 7,064,129, U.S. Pat. No. 6,858,615, U.S. Pat. No. 6,903,105, WO 2004/073629, WO 2007/146869, and WO 2007/018640, each of which is expressly incorporated by reference.

Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1\times10^{-11}$ M to $3\times10^{-5}$ M), and the cumulative change in $I_{SC}$ (inhibition) recorded. All drugs are prepared in dimethyl sulfoxide as stock solutions at a concentration of $1\times10^{-2}$ M and stored at $-20°$ C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls. The potency of the sodium channel blocking activity of representative compounds relative to amiloride in freshly excised cell from human airways is shown in Table 1.

TABLE 1

Potency of sodium channel blocking activity of compounds compared to amiloride.

| Compound Number | Potency of Sodium Channel Blockade Relative to Amiloride |
|---|---|
| 26 | 30 |
| 34 | 63 |
| 72 | 164 |
| 76 | 347 |

The potency of the sodium channel blocking activity of representative compounds in freshly excised cell from dog airways is shown in Table 2.

TABLE 2

| Compound Number | $IC_{50}$ nM |
|---|---|
| Amiloride | 781 |
| 79 | 23.5 |
| 34 | 18.8 |
| 26 | 25.4 |
| 72 | 6.3 |
| 75 | 4.3 |
| 91 | 6.1 |
| 94 | 9.6 |
| 107 | 8.1 |
| 105 | 23.5 |
| 116 | 2.7 |
| 118 | 3.2 |

Pharmacological Assays of Absorption (1) Apical Disappearance Assay

Bronchial cells (dog, human, sheep, or rodent cells) are seeded at a density of $0.25\times10^6/cm^2$ on a porous Transwell-Col collagen-coated membrane with a growth area of 1.13 $cm^2$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_1$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 μl) and is initiated by adding experimental sodium channel blockers or positive controls (amiloride, benzamil, phenamil) to the apical surface at an initial concentration of 10 μM. A series of samples (5 μl volume per sample) is collected at various time points, including 0, 5, 20, 40, 90 and 240 minutes. Concentrations are determined by measuring intrinsic fluorescence of each sodium channel blocker using a Fluorocount Microplate Fluorometer or HPLC. Quantitative analysis employs a standard curve generated from authentic reference standard materials of known concentration and purity. Data analysis of the rate of disappearance is performed using nonlinear regression, one phase exponential decay (Prism V 3.0).

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

3. In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 µl KBR, containing 10 µM test compound) is placed on the epithelial lumenal surface. Sequential 5 to 10 µl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolities, and HPLC mobilities of novel metabolites are then performed.

4. Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

Methods

Animal Preparation: Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-aerosol: Aerosols of $^{99m}$Tc-Human serum albumin (3.1 mg/ml; containing approximately 20 mCi) were generated using a Raindrop Nebulizer which produces a droplet with a median aerodynamic diameter of 3.6/tm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radiolabeled mucus.

Treatment Protocol (Assessment of activity at t-zero): A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 hours): The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics: Data were analyzed using SYSTAT for Windows, version 5. Data were analyzed using a two-way repeated ANOVA (to assess overall effects), followed by a paried t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. All reagents and solvents were purchased from Aldrich Chemical Corp. and used without further purification. Proton and carbon NMR spectra were obtained on a Bruker AC 300 spectrometer at 300 MHz and 75 MHz, respectively. Proton spectra were referenced to tetramethylsilane as an internal standard and the carbon spectra were referenced to $CDCl_3$, $CD_3OD$, acetone-$d_6$ or DMSO-$d_6$ (purchased from Aldrich or Cambridge Isotope Laboratories, unless otherwise specified). Melting points were obtained on a Mel-Temp II apparatus and are uncorrected. ESI Mass spectra were obtained on a Shimadzu LCMS-2010 EV Mass Spectrometer. HLPC analyses were obtained using a Waters XTerra RP C18 Analytical Column detected at 220 nm (unless otherwise specified) on a Shimadzu Prominence HPLC system. With a flow rate of 1.0 mL per minute, the following time program was utilized:

| Time | Percent A (H$_2$O with 0.05% TFA) | Percent B (CH$_3$CN with 0.05% TFA) |
| --- | --- | --- |
| 0:00 | 90 | 10 |
| 20:00 | 10 | 90 |
| 30:00 | 10 | 90 |
| 35:00 | 90 | 10 |

The following definitions for abbreviations will apply unless otherwise indicated.

| Abbreviation | Definition |
| --- | --- |
| THF | tetrahydrofuran |
| Cbz | Benzyloxycarbonyl i.e. - (CO)O-benzyl |
| AUC | Area under the curve or peak |
| EtOAc | Ethyl acetate |
| R$_f$ | Retardation factor |
| HPLC | High performance liquid chromatography |
| MTBE | Methyl tertiary butyl ether |
| t$_R$ | Retention time |
| GC-MS | Gas chromatography-mass spectrometry |
| wt % | Percent by weight |
| h | hours |
| min | minutes |
| MHz | megahertz |
| MeOH | methanol |
| TFA | Trifluoroacetic acid |
| UV | Ultraviolet |

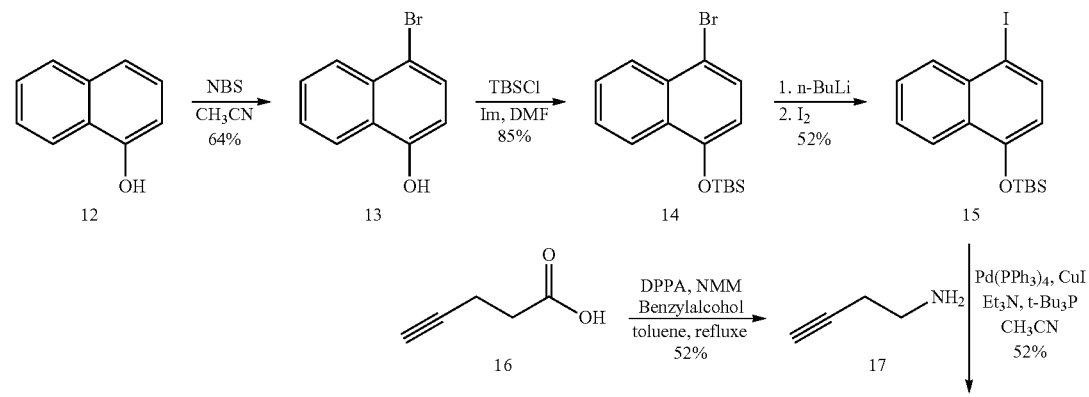

Scheme 4

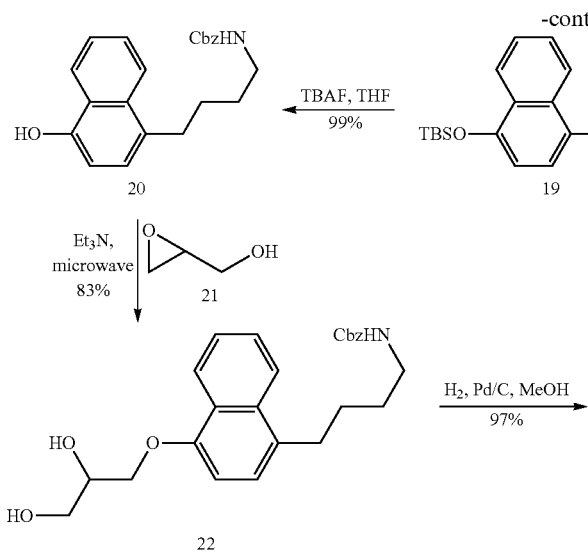
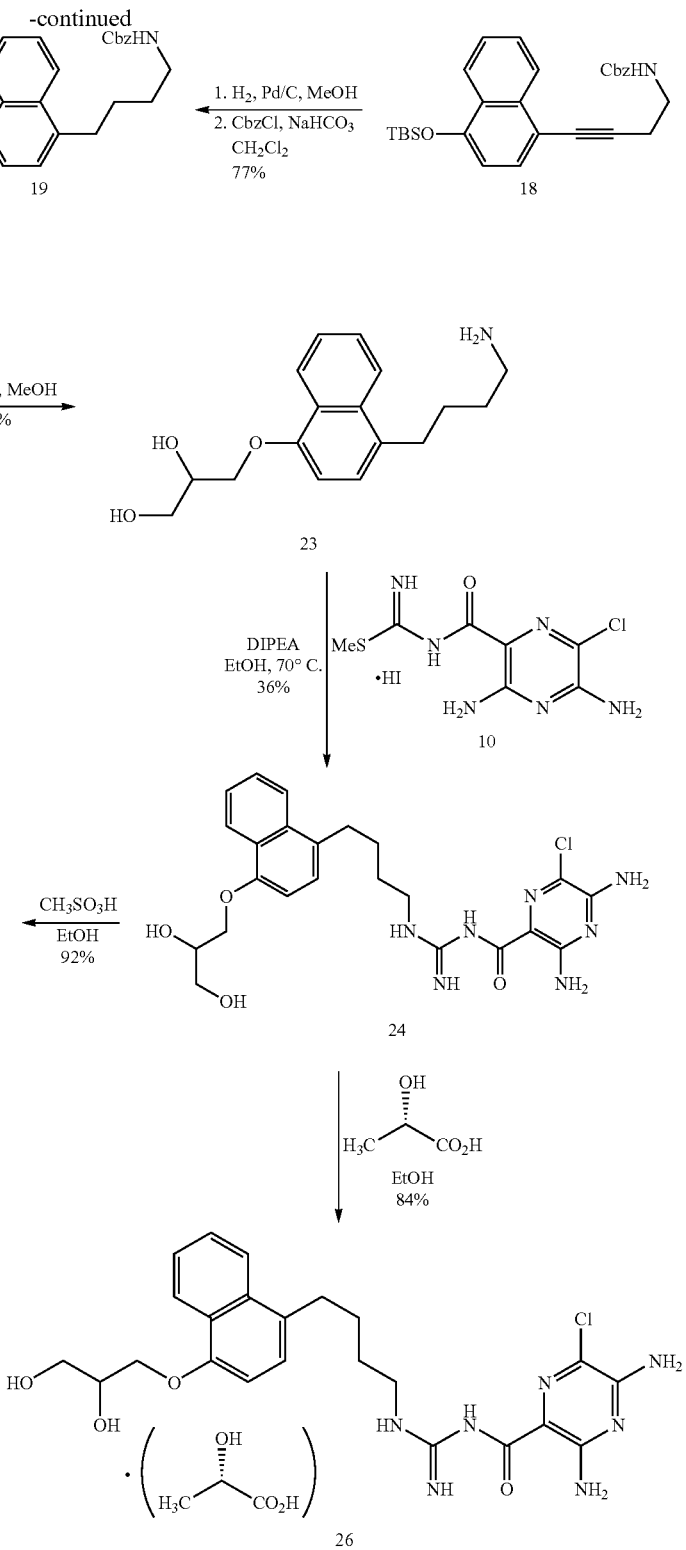

Preparation of 4-Bromonaphthol (13)

To a solution of naphthol (12, 5.0 g, 35 mmol) in CH$_3$CN (125 mL) at 0° C. was added N-bromosuccinimide (7.9 g, 45 mmole) in several portions. The reaction mixture was warmed to room temperature, stirred for 1 h, and concentrated. The residue was dissolved in EtOAc (500 mL) and the solution was washed with water (300 mL) and brine (300 mL). The organic layer was dried over MgSO$_4$, filtered, and concentrated. The residue was purified by column chromatography (silica gel, 4:1 hexanes/EtOAc) to afford 4-bromonaphthol (13, 5.0 g, 64%) as a white solid: $^1$H NMR (300

MHz, CDCl$_3$) δ 8.22-8.16 (m, 2H), 7.62-7.26 (m, 3H), 6.71 (d, J=8.0 Hz, 1H), 5.46 (s, 1H).

Preparation of (4-Bromonaphthalen-1-yloxy)(tert-butyl)dimethylsilane (14)

To a solution of imidazole (2.3 g, 34 mmole) and 4-bromonaphthol (13, 5.0 g, 22 mmole) in DMF (10 mL) at 0° C. was added t-butyldimethylsilyl chloride (3.7 g, 24.6 mmole) in several portions. The mixture was warmed to room temperature and stirred for 2 h. The reaction mixture was partitioned between Et$_2$O (500 mL) and water (300 mL) and the aqueous layer was back-extracted with Et$_2$O (300 mL). The combined organic layers were washed with water (300 mL) and brine (300 mL), dried over MgSO$_4$, filtered, and concentrated. The residue was purified by column chromatography (silica gel, hexanes) to afford (4-bromonaphthalen-1-yloxy)(tert-butyl)dimethylsilane (14, 6.4 g, 85%) as a white solid: $^1$H NMR (300 MHz, CDCl$_3$) δ 8.21 8.14 (m, 2H), 7.61-7.49 (m, 3H), 6.74 (d, J=8.2 Hz, 1H), 1.10 (s, 9H), 0.28 (s, 6H).

Preparation of tert-Butyl (4-Bromonaphthalen-1-yloxy)dimethylsilane (15)

n-Butyllithium (1.6 M in hexanes, 6.8 mL) was added dropwise to a solution of (4-bromonaphthalen-1-yloxy)(tert-butyl)dimethylsilane (14, 3.0 g, 9.0 mmole) in anhydrous THF (30 mL) at −78° C. and the mixture was stirred for 1 h. Iodine (3.4 g, 14 mmole) in THF (20 mL) was added dropwise at the same temperature and the reaction mixture was stirred for 2 h. The reaction mixture was diluted with Et$_2$O (500 mL), washed with 1:1 saturated Na$_2$S$_2$O$_3$/NaHCO$_3$ (2×300 mL) and 1:1 H$_2$O/brine (300 mL), dried over MgSO$_4$, filtered, and concentrated. The residue was purified by column chromatography (silica gel, hexanes) to afford tert-butyl (4-bromonaphthalen-1-yloxy)dimethylsilane (15, 1.8 g, 52%) as a white solid: $^1$H NMR (300 MHz, CDCl$_3$) δ 8.15 (d, J=8.4 Hz, 1H), 8.02 (d, J=8.6 Hz, 1H), 7.89 (d, J=8.1 Hz, 1H), 7.59-7.47 (m, 2H), 6.64 (d, J=8.1 Hz, 1H), 1.09 (s, 9H), 0.28 (s, 6H).

Preparation of 3-Butyn-1-amine (17)

To a solution of 4-pentynoic acid (16, 15 g, 150 mmole), benzyl alcohol (17 mL, 170 mmole), and 4-methyl morpholine (17 mL, 150 mmole) in anhydrous toluene (80 mL) was added dropwise diphenyl phosphoryl azide (33 mL, 150 mmole) at room temperature. The reaction mixture was stirred for 15 min. The reaction temperature was carefully raised to 60-70° C., during which vigorous efflorescence was observed. The reaction mixture was stirred at the same temperature for 2 h and then at 110° C. for 18 h. The reaction mixture was cooled to room temperature and concentrated to a thick brown slurry. The residue was dissolved in CH$_2$Cl$_2$ (300 mL) and the solution was stirred for an additional 30 min. The mixture was washed with water (2×300 mL) and the combined aqueous layers were back-extracted with CH$_2$Cl$_2$ (2×300 mL). The combined organic layers were dried over MgSO$_4$, filtered, and concentrated. The residue was purified by column chromatography (silica gel, 4:1 hexanes/EtOAc) to afford amine 17 (16 g, 52%) as a light yellow oil: $^1$H NMR (300 MHz, CDCl$_3$) δ 7.37-7.33 (m, 5H), 5.11 (br s, 3H), 3.36 (q, J=6.4 Hz, 2H), 2.41 (td, J=6.4, 2.4 Hz, 2H), 1.99 (t, J=2.6 Hz, 1H).

Preparation of Benzyl 4-[4-(tert-Butyldimethylsilyloxy)naphthalen-1-yl]-3-butynylcarbamate (18)

A solution of tert-butyl (4-bromonaphthalen-1-yloxy)dimethylsilane (15, 3.1 g, 8.2 mmole), amine 17 (3.3 g, 16 mmole), and triethyl amine (4.5 mL, 33 mmole) in CH$_3$CN (70 mL) pre-cooled to −78° C. was degassed with argon. Tri-tert-butyl phosphine (10% in hexanes, 3.3 g, 1.6 mmole), Pd(PPh$_3$)$_4$ (940 mg, 0.82 mmole), and CuI (78 mg, 0.41 mmole) were added rapidly in one portion at the same temperature. The mixture was warmed to −30° C. and shaken until a homogeneous solution was formed, then cooled to −78° C., and degassed with argon. The mixture was warmed to room temperature and stirred for 18 h. Water (10 mL) was added to the reaction mixture and the mixture was concentrated. The residue was diluted with EtOAc (500 mL) and the organic layer was washed with water (300 mL) and brine (300 mL), dried over Na$_2$SO$_4$, filtered, and concentrated. The residue was purified by column chromatography (silica gel, 4:1 hexanes/EtOAc) to afford carbamate 18 (2.0 g, 52%) as a light yellow oil: $^1$H NMR (300 MHz, CDCl$_3$) δ 8.24-8.16 (m, 2H), 7.53-7.45 (m, 3H), 7.38 7.30 (m, 5H), 6.77 (d, J=7.9 Hz, 1H), 5.14 (br s, 3H), 3.56 3.49 (m, 2H), 2.76 (t, J=6.5 Hz, 2H), 1.09 (s, 9H), 0.29 (s, 6H).

Preparation of Benzyl 4-[4-(tert-Butyldimethylsilyloxy)naphthalen-1-yl]butylcarbamate (19)

A solution of carbamate 18 (2.0 g, 4.3 mmole) and 10% Pd/C (300 mg) in MeOH (60 mL) was subjected to hydrogenation conditions (50 psi) for 8 h at room temperature. The reaction mixture was filtered through a plug of diatomaceous earth and the plug was washed with MeOH (2×20 mL). The filtrate was then concentrated in vacuo to afford crude amine (1.4 g) which was dissolved in 1:1 CH$_2$Cl$_2$/NaHCO$_3$ (saturated solution) (30 mL). Benzyl chloroformate (0.62 mL) was added dropwise at room temperature and the reaction mixture was stirred for 1 h. The mixture was concentrated, the residue was dissolved in EtOAc (500 mL), and the solution was washed with water (300 mL) and brine (300 mL). The organic layer was dried over Na$_2$SO$_4$, filtered, and concentrated. The residue was purified by column chromatography (silica gel, 4:1 hexanes/EtOAc) to afford butylcarbamate 19 (1.5 g, 77%) as a light yellow oil: $^1$H NMR (300 MHz, DMSO-d$_6$) δ 8.24 (m, 1H), 7.91 (d, J=7.4 Hz, 1H), 7.51-7.42 (m, 2H), 7.34-7.28 (m, 5H), 7.12 (d, J=7.6 Hz, 1H), 6.77 (d, J=7.6 Hz, 1H), 5.08 (br s, 2H), 4.75 (br s, 1H), 3.22 (q, J=6.4 Hz, 2H), 2.99 (q, J=7.4 Hz, 2H), 1.76-1.71 (m, 2H), 1.67-1.56 (m, 2H), 1.09 (s, 9H), 0.27 (s, 6H).

Preparation of Benzyl 4-(4-Hydroxynaphthalen-1-yl)butylcarbamate (20)

Tetrabutylammonium fluoride (1 M in THF, 1.0 mL) was added to a solution of benzyl 4-[4-(tert-butyldimethylsilyloxy)naphthalen-1-yl]butylcarbamate (19, 380 mg, 0.80 mmol) in anhydrous THF (15 ml) at room temperature. The reaction mixture was stirred for 2 h and concentrated to dryness. The residue was purified by column chromatography (silica gel, 3:1 hexanes/EtOAc) to afford butylcarbamate 20 (287 mg, 99%) as white solid: $^1$H NMR (300 MHz, CDCl$_3$) δ 8.23-8.21 (m, 1H), 7.84-7.81 (m, 1H), 7.42-7.34 (m, 2H), 7.25-7.15 (m, 5H), 6.96 (d, J=7.5 Hz, 1H), 6.62 (d, J=7.5 Hz, 1H), 5.00 (br s, 2H), 4.65 (br s, 1H), 3.13 (q, J=6.6 Hz, 2H), 2.87 (t, J=7.5 Hz, 2H), 1.64-1.47 (m, 4H).

Preparation of Benzyl 4-[4-(2,3-Dihydroxypropoxy)naphthalen-1-yl]butylcarbamate (22)

A solution of benzyl 4-(4-hydroxynaphthalen-1-yl)butylcarbamate (20, 287 mg, 0.82 mmole), oxiran-2-ylmethanol (21, 0.07 mL, 1.00 mmole) and triethylamine (0.01 mL, 0.05 mmole) in absolute EtOH (9.28 mL) was subjected to microwave irradiation at 130° C. for 30 min. The reaction mixture was concentrated in vacuo and the residue was purified by column chromatography (silical gel, 95:5 $CH_2Cl_2$/MeOH) to afford butylcarbamate 22 (293 mg, 83%) as a light yellow thick oil: $^1H$ NMR (300 MHz, $CDCl_3$) δ 8.24 (d, J=7.7 Hz, 1H), 7.94 (d, J=8.1 Hz, 1H), 7.52-7.45 (m, 2H), 7.37 7.28 (m, 5H), 7.18 (d, J=7.7 Hz, 1H), 6.75 (d, J=8.0 Hz, 1H), 5.09 (br s, 2H), 4.71 (br s, 1H), 4.29-4.20 (m, 3H), 3.98-3.81 (m, 2H), 3.23 (q, J=6.5 Hz, 2H), 3.00 (t, J=7.5 Hz, 2H), 2.65 (d, J=4.5 Hz, 1H), 2.06 (t, J=5.8 Hz, 1H), 1.83-1.53 (m, 4H).

Preparation of 3-[4-(4-Aminobutyl)naphthalen-1-yloxy]propane-1,2-diol (23)

A solution of benzyl 4-[4-(2,3-dihydroxypropoxy)naphthalen-1-yl]butylcarbamate (22, 340 mg, 0.80 mmole) and 10% Pd/C (50 mg) in MeOH (50 mL) was subjected to hydrogenation conditions (1 atm) for 2 h at room temperature. The reaction mixture was filtered through a plug of diatomaceous earth and the plug was washed with MeOH. The filtrate was then concentrated in vacuo to afford diol 23 (226 mg, 97%) as a yellow solid: MS m/z 290 $[C_{17}H_{23}NO_3+H]^+$. Diol 23 was used in the next step without further purification.

Preparation of 2,4-Diamino-5-chloro-N-{N-[4-(4-(2,3-dihydroxypropoxy)naphthalen-1-yl)butyl]carbamimidoyl}benzamide (24)

To a solution of 3-[4-(4-aminobutyl)naphthalen-1-yloxy]propane-1,2-diol (23, 226 mg, 0.78 mmole) and methyl 3,5-diamino-6-chloropyrazine-2-carbonylcarbamimidothioate (10, 455 mg, 1.17 mmole) in EtOH (10 mL) was added diisopropylethylamine (0.82 mL, 4.69 mmole) at room temperature. The reaction mixture was heated at 70° C. in a sealed tube for 7 h, then cooled to room temperature, and concentrated in vacuo. The residue was purified by column chromatography (silica gel, 80:18:2 $CHCl_3$/$CH_3OH$/$NH_4OH$) to afford benzamide 24 (140 mg, 36%) as a yellow solid: $^1H$ NMR (300 MHz, $CD_3OD$) δ 8.31 (d, J=8.2 Hz, 1H), 7.98 (d, J=8.2 Hz, 1H), 7.53 7.40 (m, 2H), 7.23 (d, J=7.9 Hz, 1H), 6.83 (d, J=7.8 Hz, 1H), 4.22 4.10 (m, 3H), 3.84 3.72 (m, 2H), 3.31-3.25 (m, 2H), 3.08-3.03 (m, 2H), 1.89-1.70 (m, 4H).

Preparation of 3,5-Diamino-6-chloro-N-(N-{4-[6-(2,3-dihydropropoxy)naphthalen-2-yl]butyl}carbamimidoyl)pyrazine-2-carboxamide Methanesulfonic Acid Salt (25)

To a solution of 3,5-diamino-6-chloro-N-(N-{4-[6-(2,3-dihydropropoxy)naphthalen-2-yl]butyl}carbamimidoyl)pyrazine-2-carboxamide (24, 119 mg, 0.24 mmole) in EtOH (5 mL) was added methanesulfonic acid (22.7 mg, 0.24 mmole) at room temperature. The reaction mixture was stirred for 15 min. The solution was concentrated and the residue was azeotroped with MeOH. The residue was dissolved in $H_2O$ (4 mL) and lyophilized to afford methanesulfonic acid salt 25 (130 mg, 92%) as a yellow solid: mp 129-132° C.; $^1H$ NMR (300 MHz, DMSO-$d_6$) δ 10.45 (br s, 1H), 9.12 (br s, 1H), 8.86 (br s, 1H), 8.70 (br s, 1H), 8.27 (dd, J=8.0, 1.3 Hz, 1H), 8.02 (d, J=8.2 Hz, 1H), 7.59-7.49 (m, 2H), 7.47 (br s, 2H), 7.26 (d, J=7.8, 1H), 6.87 (d, J=7.9 Hz, 1H), 5.06 (d, J=4.7 Hz, 1H), 4.71 (t, J=5.4, 1H), 4.16-3.93 (m, 3H), 3.55 (td, J=5.6, 1.5 Hz, 2H), 3.16 (d, J=5.3 Hz, 2H), 3.00 (t, J=7.0 Hz, 2H), 2.29 (s, 3H), 1.76-1.57 (m, 4H); ESI-MS m/z 524 $[C_{23}H_{28}ClN_7O_4^+H]^+$.

Preparation of 2,4-Diamino-5-chloro-N-(N-{4-[4-(2,3-dihydroxypropoxy)naphthalen-1-yl]butyl}carbamimidoyl)benzamide L-(+)-Lactic Acid Salt (26)

To a solution of 2,4-diamino-5-chloro-N-(N-{4-[4-(2,3-dihydroxypropoxy)naphthalen-1-yl]butyl}carbamimidoyl)benzamide (24, 28 mg, 0.06 mmole) in EtOH (10 mL) was added L-(+)-lactic acid (5.20 mg, 0.06 mmole) at room temperature and the reaction mixture was stirred for 15 min. The solution was concentrated and the residue was azeotroped with MeOH. The residue was dissolved in $H_2O$ (3 mL) and lyophilized to afford lactic acid salt 26 (28 mg, 84%) as a yellow solid: mp 115-118° C.; $^1H$ NMR (300 MHz, $CD_3OD$) δ 8.32 (d, J=8.4 Hz, 1H), 8.01 (d, J=8.4 Hz, 1H), 7.53 7.40 (m, 2H), 7.24 (d, J=7.8 Hz, 1H), 6.83 (d, J=7.8 Hz, 1H), 4.21 4.10 (m, 3H), 4.01-3.94 (m, 1H), 3.82-3.73 (m, 2H), 3.35-3.33 (m, 2H), 3.08 (t, J=7.0, 1H), 1.89-1.77 (m, 4H), 1.31 (d, J=7.0 Hz, 3H); ESI-MS m/z 524 $[C_{23}H_{28}ClN_7O_4^+H]^+$.

Scheme 5

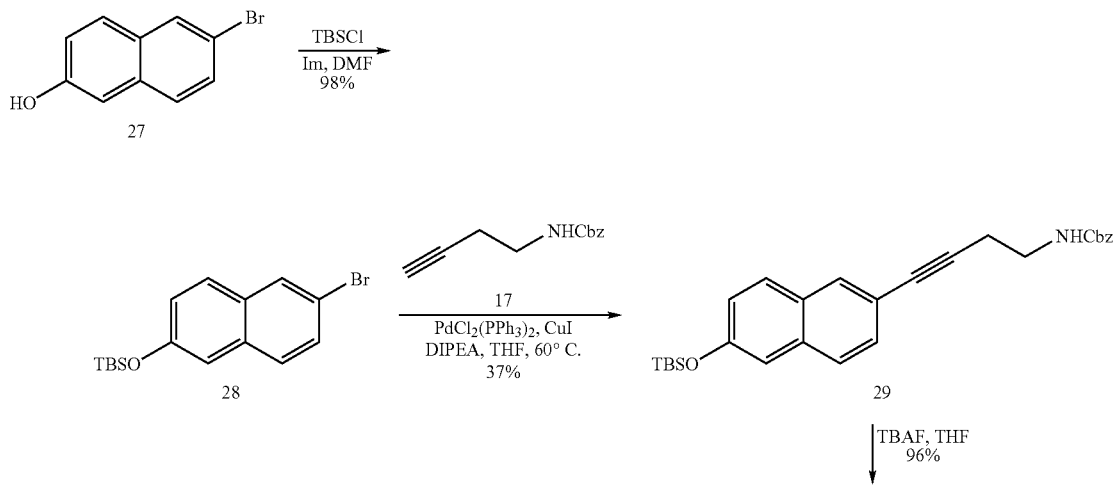

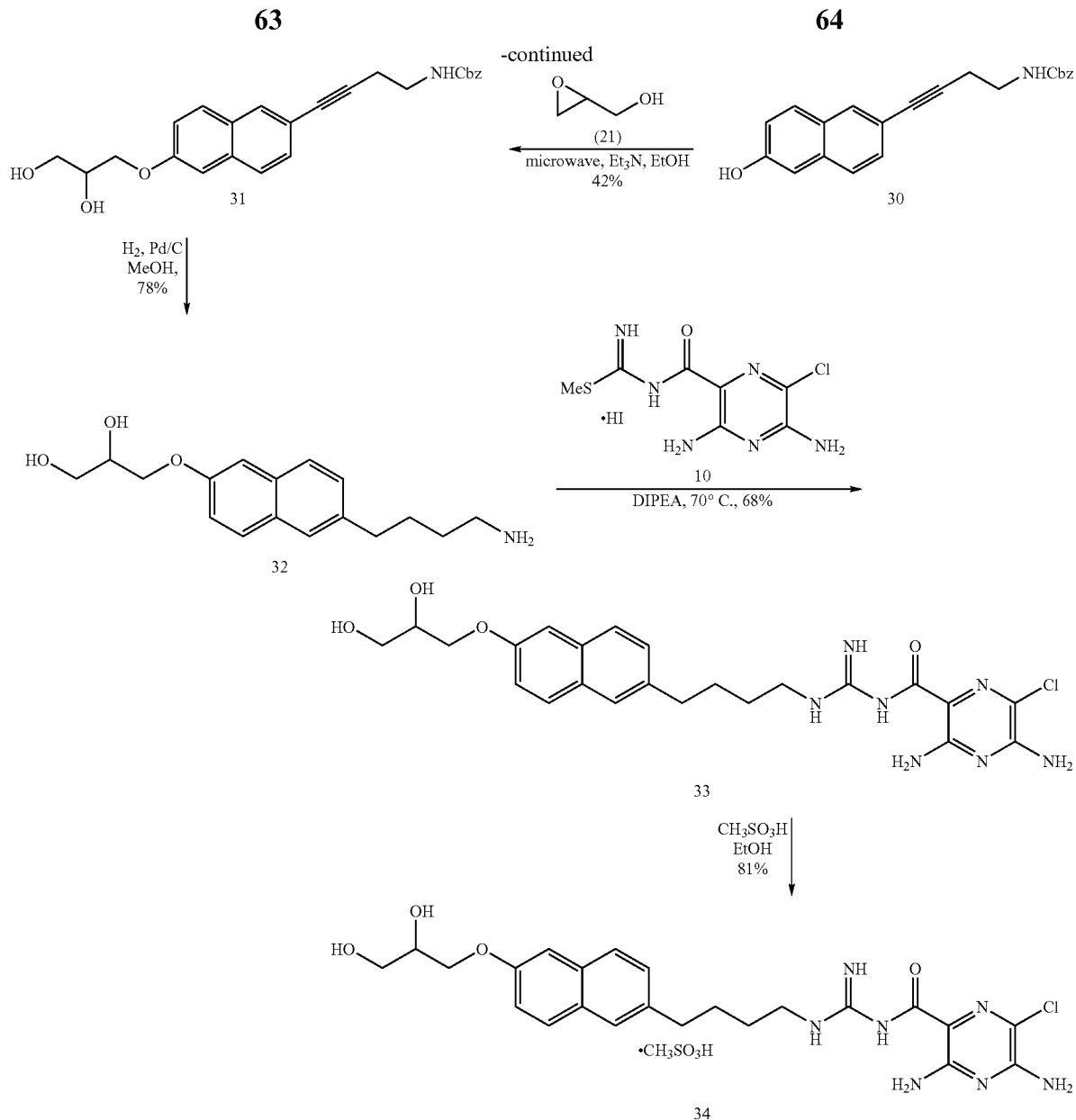

Preparation of (6-Bromonaphthalen-2-yloxy)(tert-butyl)dimethylsilane (28)

A solution of 6-bromonaphthalen-2-ol (5.0 g, 22.4 mmol) and imidazole (2.3 g, 33.6 mmole) in N,N-dimethylformamide (DMF) (5.0 mL) was added t-butyldimethylsilyl chloride (TBDMSCl) (3.7 g, 24.6 mmole) in one portion at 0° C. The mixture was allowed to warm to room temperature and stirred for 3 h. The reaction mixture was partitioned between EtOAc (500 mL) and water (300 mL). The aqueous layer was separated and extracted with EtOAc (2×100 mL) and the combined organic extracts were washed with brine (300 mL), dried over $Na_2SO_4$, filtered, and concentrated. The residue was purified by column chromatography (silica gel, hexanes) to afford (6-bromonaphthalen-2-yloxy)(tert-butyl)dimethylsilane (28, 7.4 g, 98%) as a white solid: $^1$H NMR (300 MHz, $CDCl_3$) δ 7.91 (d, J=1.8 Hz, 1H), 7.64 (d, J=8.7 Hz, 1H), 7.56 (d, J=8.7 Hz, 1H), 7.48 (dd, J=8.7, 1.8 Hz, 1H), 7.15 (d, J=2.4 Hz, 1H), 7.09 (dd, J=9.0, 2.4 Hz, 1H), 1.01 (s, 9H), 0.24 (s, 6H).

Preparation of Benzyl 4-[6-(tert-Butyldimethylsilyloxy)naphthalen-2-yl]but-3-ynylcarbamate (29)

A solution of (6-bromonaphthalen-2-yloxy)(tert-butyl)dimethylsilane (28, 3.4 g, 10.0 mmol), benzyl but-3-ynylcarbamate (17, 2.0 g, 10 mmole), and triethylamine (20 mL) in anhydrous THF (60 mL) pre-cooled to −78° C. was degassed with argon. The mixture was warmed to room temperature and dichlorobis(triphenylphosphine)palladium(11) ($PdCl_2(PPh_3)_2$) (702 mg, 1 mmole) and CuI (381 mg, 2 mmole) were added rapidly in one portion under argon. The mixture was heated at 60° C. for 4 h, then at room temperature for 48 h. The reaction mixture was filtered through a plug of diatomaceous earth and the filtrate was partitioned between EtOAc (500 mL) and 1 N HCl (200 mL). The aqueous layer was separated and back-extracted with EtOAc (300 mL). The combined organic extracts were washed with water (300 mL) and brine (300 mL), dried over Na$_2$SO$_4$, filtered, and concentrated. The residue was purified by column chromatography (silical gel, 10:1 hexanes/EtOAc) to afford carbamate 29 (1.24 g, 37%) as a brown thick oil: $^1$H NMR (300 MHz, CDCl$_3$) δ 7.83 (s, 1H), 7.65 (d, J=9.0 Hz, 1H), 7.60 (d, J=8.7 Hz, 1H), 7.39-7.29 (m, 6H), 7.13 (d, J=2.1 Hz, 1H), 7.07 (dd, J=8.7, 2.4 Hz, 1H), 5.17 (br s, 1H), 5.13 (s, 2H), 3.46 (q, J=6.3 Hz, 2H), 2.67 (t, J=6.3 Hz, 2H), 1.01 (s, 9H), 0.25 (s, 6H).

Preparation of Benzyl 4-(6-Hydroxynaphthalen-2-yl)but-3-ynylcarbamate (30)

To a solution of benzyl 4-[6-(tert-butyldimethylsilyloxy) naphthalen-2-yl]but-3-ynylcarbamate (29, 578 mg, 1.26 mmol) in anhydrous THF (60 mL) was added dropwise tetrabutylammonium fluoride (1 M in THF, 1.38 mL) and the mixture was stirred for 2 h at room temperature. The resulting solution was concentrated in vacuo and the residue was purified by column chromatography (silical gel, 95:5 CH$_2$Cl$_2$/MeOH) to afford carbamate 30 (418 mg, 96%) as a pale yellow solid: $^1$H NMR (300 MHz, CDCl$_3$) δ 7.82 (s, 1H), 7.67 (d, J=9.6 Hz, 1H), 7.58 (d, J=8.4 Hz, 1H), 7.37-7.29 (m, 6H), 7.11-7.08 (m, 2H), 5.30 (br s, 2H), 5.14 (s, 2H), 3.48 (q, J=6.3 Hz, 2H), 2.68 (t, J=6.6 Hz, 2H).

Preparation of Benzyl 4-[6-(2,3-Dihydroxypropoxy) naphthalen-2-yl]but-3-ynylcarbamate (31)

A solution of 4-(6-hydroxynaphthalen-2-yl)but-3-ynylcarbamate (30, 390 mg, 1.1 mmole), oxiran-2-ylmethanol (21, 0.1 mL, 1.4 mmole), and triethylamine (0.01 mL, 0.06 mmole) in absolute EtOH (8.8 mL) was subjected to microwave irradiation at 130° C. for 30 min. The reaction mixture was concentrated in vacuo and the residue was purified by column chromatography (silical gel, 95:5 CH$_2$Cl$_2$/MeOH) to afford carbamate 31 (236 mg, 42%) as a white solid: $^1$H NMR (300 MHz, CD$_3$OD) δ 7.80 (s, 1H), 7.68 (dd, J=8.7, 3.9 Hz, 2H), 7.38-7.16 (m, 8H), 5.10 (s, 2H), 4.18 (dd, J=9.6, 4.2 Hz, 1H), 4.11-4.01 (m, 2H), 3.76-3.67 (m, 2H), 3.39-3.31 (m, 4H), 2.63 (t, J=6.9 Hz, 2H).

Preparation of 3-[6-(4-Aminobutyl)naphthalen-2-yloxy]propane-1,2-diol (32)

A suspension of benzyl 4-[6-(2,3-dihydroxypropoxy) naphthalen-2-yl]but-3-ynylcarbamate (31, 236 mg, 0.5 mmole) and 10% Pd/C (96 mg) in MeOH (70 mL) was subjected to hydrogenation conditions (1 atm) for 1 h at room temperature. The reaction mixture was filtered through a plug of diatomaceous earth and the plug was washed with MeOH. The filtrate was then concentrated in vacuo to afford diol 32 (123 mg, 78%) as a white solid: $^1$H NMR (300 MHz, CD$_3$OD) δ 7.67 (d, J=8.4 Hz, 2H), 7.56 (s, 1H), 7.30 (dd, J=8.4, 1.5 Hz, 1H), 7.20 (d, J=2.4 Hz, 1H), 7.14 (dd, J=8.7, 2.4 Hz, 1H), 4.18-3.99 (m, 3H), 3.76-3.65 (m, 2H), 2.75 (dt, J=10.8, 7.2 Hz, 4H), 1.80-1.70 (m, 2H), 1.62-1.52 (m, 2H).

Preparation of 3,5-Diamino-6-chloro-N-(N-{4-[6-(2, 3-dihydropropoxy)naphthalen-2-yl] butyl}carbamimidoyl)pyrazine-2-carboxamide (33)

To a solution of 3-[6-(4-aminobutyl)naphthalen-2-yloxy] propane-1,2-diol (32, 51 mg, 0.2 mmole) and methyl 3,5-diamino-6-chloropyrazine-2-carbonylcarbamimidothioate (10, 103 mg, 0.3 mmole) in EtOH (2 mL) was added diisopropylethylamine (0.2 mL, 1.1 mmole) at room temperature. The reaction mixture was heated at 70° C. in a sealed tube for 7 h, then cooled to room temperature, and concentrated in vacuo. The residue was purified by column chromatography (silica gel, 80:18:2 CHCl$_3$/CH$_3$OH/NH$_4$OH) to afford carboxamide 33 (34 mg, 68%) as a yellow solid: $^1$H NMR (300 MHz, CD$_3$OD) δ 7.67 (d, J=8.7 Hz, 2H), 7.56 (s, 1H), 7.30 (dd, J=8.4, 1.5 Hz, 1H), 7.19 (d, J=2.4 Hz, 1H), 7.13 (dd, J=9.0, 2.4 Hz, 1H), 4.22-3.99 (m, 3H), 3.76 3.65 (m, 2H), 3.25-3.23 (m, 2H), 2.79 (t, J=7.2 Hz, 2H), 1.84-1.65 (m, 4H).

Preparation of 3,5-Diamino-6-chloro-N-(N-{4-[6-(2, 3-dihydropropoxy)naphthalen-2-yl] butyl}carbamimidoyl)pyrazine-2-carboxamide Methanesulfonic Acid Salt (34)

To a solution of 3,5-diamino-6-chloro-N-(N-4-[6-(2,3-dihydropropoxy)naphthalen-2-yl]butylcarbamimidoyl)pyrazine-2-carboxamide (33, 190 mg, 0.4 mmole) in EtOH (10 mL) was added methanesulfonic acid (72.7 mg, 0.8 mmole) at room temperature and the reaction mixture was stirred for 15 min. The solution was concentrated and the residue was azeotroped with MeOH. The residue was dissolved in 8:2 MeOH/H$_2$O (10 mL) and lyophilized to afford methanesulfonic acid salt 34 (185 mg, 81%) as a yellow solid: mp 146-149° C.; $^1$H NMR (300 MHz, DMSO-d$_6$) δ 10.4 (s, 1H), 9.14 (br s, 1H), 8.87 (br s, 1H), 8.71 (br s, 1H), 7.74 (d, J=8.7 Hz, 2H), 7.62 (s, 1H), 7.44 (br s, 2H), 7.34 (dd, J=8.4, 0.9 Hz, 1H), 7.26 (d, J=2.1 Hz, 1H), 7.14 (dd, J=9.0, 2.4 Hz, 1H), 5.76 (s, 1H), 4.09 (dd, J=9.9, 4.2 Hz, 1H), 3.98 3.81 (m, 2H), 3.48 (d, J=5.4 Hz, 2H), 3.32 (q, J=5.7 Hz, 2H), 2.75 (t, J=7.2 Hz, 2H), 2.34 (s, 6H), 1.72-1.59 (m, 4H); ESI-MS m/z 502 [C$_{23}$H$_{29}$ClN$_7$O$_4$$^+$ H]$^+$.

Scheme 11

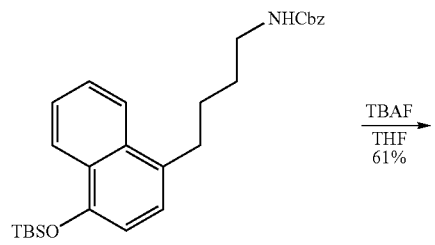

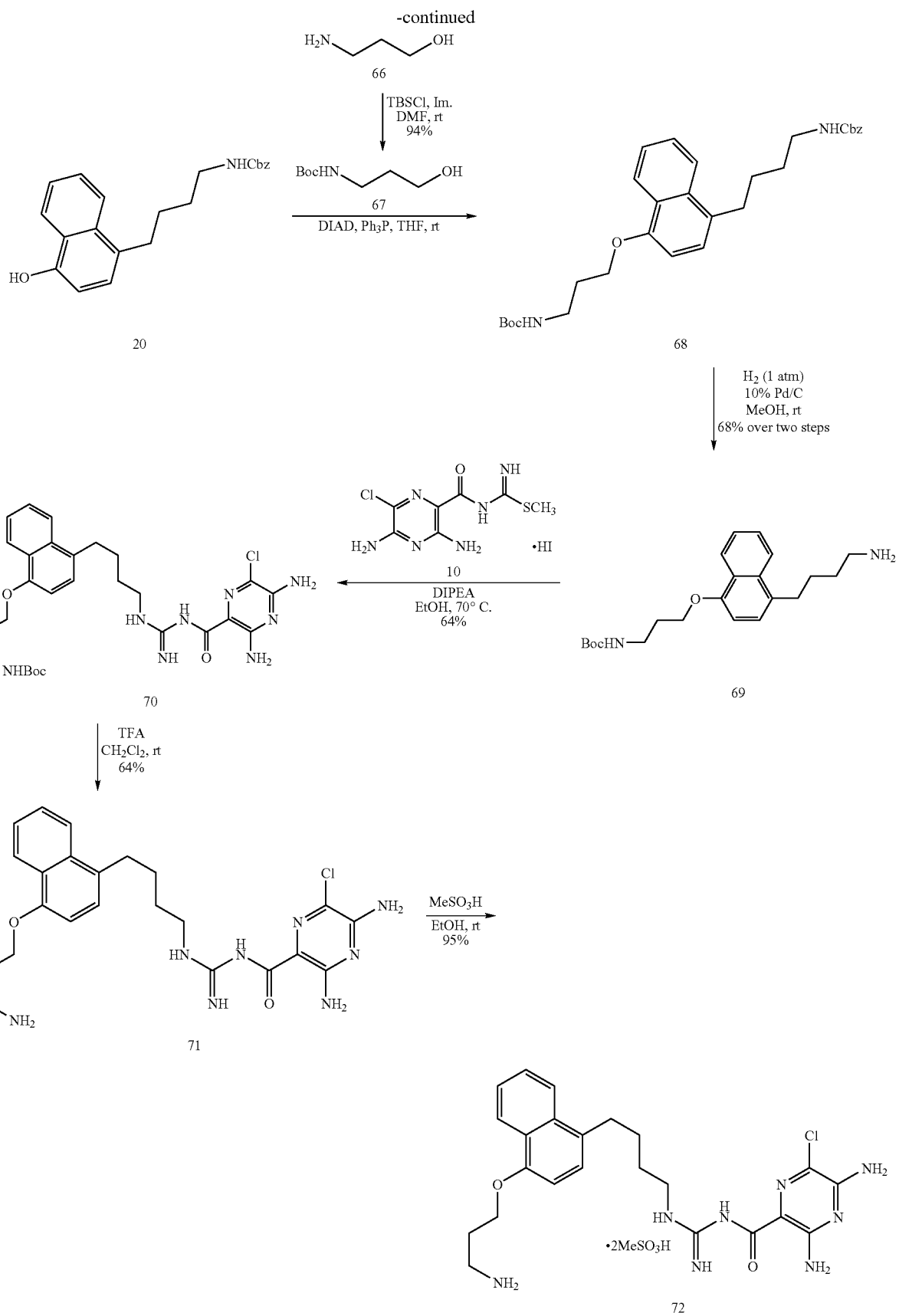

Preparation of Benzyl 4-(4-Hydroxynaphthalen-1-yl)butylcarbamate (20)

Tetrabutylammonium fluoride (1.0 M in THF, 1.1 mL) was added to a solution of benzyl 4-[4-(tert-butyldimethylsilyloxy)naphthalen-1-yl]butylcarbamate (19, 500 mg, 1.1 mmole) in THF (5 ml) at room temperature. The reaction mixture was stirred for 2 h. The reaction mixture was concentrated to dryness. The residue was purified by column chromatography (silica gel, 3:1 hexanes/EtOAc) to afford carbamate 20 (230 mg, 61%) as a white solid: $^1$H NMR (300 MHz, CDCl$_3$) δ 8.25 8.21 (m, 1H), 7.91 (dd, J=6.6, 1.8 Hz, 1H), 7.52-7.43 (m, 2H), 7.35-7.27 (m, 5H), 7.05 (d, J=7.5 Hz, 1H), 6.72 (d, J=7.5 Hz, 1H), 5.10 (s, 2H), 4.75 (br s, 1H), 3.23 (q, J=6.6 Hz, 2H), 2.95 (t, J=7.2 Hz, 2H), 1.76-1.56 (m, 4H).

Preparation of tert-Butyl 3-Hydroxypropylcarbamate (67)

To a solution of 3-aminopropanol (66, 5.0 g, 67 mmole) in 1:1 dioxane/2 N NaOH (100 mL) was added di-tert-butyl dicarbonate (17.0 g, 80 mmole) in dioxane (10 mL) at 0° C. The reaction mixture was warmed to room temperature and stirred for 1 h. The mixture was first acidified to pH 1 with concentrated HCl and then neutralized to pH 7 with 2 N NaOH. The mixture was then extracted with EtOAc (3×200 mL). The combined organic layers were dried over MgSO$_4$ and concentrated. The residue was purified by column chromatography (silica gel, 3:1 hexanes/EtOAc) to afford tert-butyl 3-hydroxypropylcarbamate (67, 11.0 g, 94%) as a light yellow oil: $^1$H NMR (300 MHz, CDCl$_3$) δ 4.80 (br s, 1H), 3.66 (q, J=5.7 Hz, 2H), 3.33 (q, J=6.3 Hz, 2H), 2.97 (br s, 1H), 1.71-1.63 (m, 2H), 1.45 (s, 9H).

Preparation of Compound (68)

Diisopropylazodicarboxylate (120 mg, 0.59 mmole) was added dropwise to a solution of benzyl 4-(4-hydroxynaphthalen-1-yl)butylcarbamate (20, 206 mg, 0.59 mmole), tert-butyl 3-hydroxypropylcarbamate (67, 104 mg, 0.59 mmole), and triphenylphosphine (187 mg, 0.71 mmole) in anhydrous THF (5 mL) at 0° C. The reaction mixture was warmed to room temperature and stirred for 5 h. The reaction mixture was concentrated and the residue was purified by column chromatography (silica gel, 2:1 hexanes/EtOAc) to afford a mixture of ether 68 and hydrazine byproduct (630 mg) which was used in the next step without further purification.

Preparation of tert-Butyl 3-[4-(4-Aminobutyl)naphthalene-1-yloxy]propylcarbamate (69)

A suspension of mixture 68 (630 mg) and 10% Pd/C (300 mg) in MeOH (25 mL) was subject to hydrogenation conditions (1 atm) for 1 h at room temperature. The reaction mixture was filtered through a plug of diatomaceous earth and the plug was washed with MeOH. The filtrate was concentrated in vacuo and the residue was purified by column chromatography (silica gel, 80:18:2 CHCl$_3$/CH$_3$OH/NH$_4$OH) to afford carbamate 69 (260 mg, 68% over two steps) as a white solid: $^1$H NMR (300 MHz, CD$_3$OD) δ 8.28 (dd, J=8.4, 1.2 Hz, 1H), 7.98 (d, J=8.1 Hz, 1H), 7.55-7.42 (m, 2H), 7.22 (d, J=7.8 Hz, 1H), 6.79 (d, J=8.1 Hz, 1H), 4.15 (t, J=6.0 Hz, 2H), 3.32-3.30 (m, 2H), 3.05 (t, J=6.9 Hz, 2H), 2.90 (t, J=7.5 Hz, 2H), 2.11-2.03 (m, 2H), 1.79-1.68 (m, 4H), 1.42 (s, 9H).

Preparation of tert-Butyl 3-{4-[4-(3-(3,5-Diamino-6-chloropyrazine-2-carbonyl)guanidine)butyl]naphthalen-1-yloxy}propylcarbamate (70)

To a solution of tert-butyl 3-[4-(4-aminobutyl)naphthalene-1-yloxy]propylcarbamate (69, 350 mg, 0.94 mmole) and methyl 3,5-diamino-6-chloropyrazine-2-carbonylcarbamimidothioate (10, 600 mg, 1.41 mmole) in EtOH (20 mL) was added diisopropylethylamine (1.6 mL, 5.2 mmole) at room temperature. The reaction mixture was heated at 70° C. in a sealed tube for 7 h, cooled to room temperature and concentrated to dryness. The residue was dissolved in CHCl$_3$ (300 mL) and washed with saturated NaHCO$_3$ (2×200 mL). The organic layer was dried over MgSO$_4$, filtered, and concentrated. The residue was purified by column chromatography (silica gel, 90:9:1 CHCl$_3$/CH$_3$OH/NH$_4$OH) to afford carbamate 70 (350 mg, 64%) as a light yellow solid: $^1$H NMR (300 MHz, CD$_3$OD) δ 8.27 (dd, J=8.1, 0.9 Hz, 1H), 7.99 (d, J=8.1 Hz, 1H), 7.50 (td, J=6.6, 1.2 Hz, 1H), 7.42 (td, J=6.6, 1.2 Hz, 1H), 7.23 (d, J=7.8 Hz, 1H), 6.80 (d, J=7.8 Hz, 1H), 4.17 (t, J=6.0 Hz, 2H), 3.66-3.54 (m, 2H), 3.16 3.05 (m, 4H), 2.12-2.03 (m, 2H), 1.84-1.76 (m, 4H), 1.41 (s, 9H).

Preparation of 3,5-Diamino-N-(N-{4-[4-(3-aminopropoxy)naphthalen-1-yl]butyl}carbamimidoyl)-6-chloropyrazine-2-carboxamide (71)

To a solution of carbamate 70 (350 mg, 0.6 mmole) in CH$_2$Cl$_2$ (35 mL) was added dropwise trifluoroacetic acid (2.0 mL) at room temperature. The reaction mixture was stirred for 3 h. The reaction mixture was concentrated in vacuo and azeotroped with MeOH (2×100 mL). The residue was dissolved in water and the solution was neutralized with saturated NaHCO$_3$ which resulted in the precipitation of carboxamide 71. Compound 71 was collected by filtration and purified by column chromatography (silica gel, 80:18:2 CHCl$_3$/CH$_3$OH/NH$_4$OH) to afford amine 71 (185 mg, 64%) as an off-white solid: $^1$H NMR (300 MHz, CD$_3$OD) δ 8.23 (dd, J=8.1, 0.6 Hz, 1H), 7.99 (d, J=8.1 Hz, 1H), 7.50 (td, J=6.9, 1.5 Hz, 1H), 7.41 (td, J=6.9, 1.2 Hz, 1H), 7.22 (d, J=7.8 Hz, 1H), 6.81 (d, J=7.8 Hz, 1H), 4.20 (t, J=6.3 Hz, 2H), 3.25 (t, J=6.3 Hz, 2H), 3.05 (t, J=6.9 Hz, 2H), 2.97 (t, J=6.9 Hz, 2H), 2.14 2.05 (m, 2H), 1.89-1.69 (m, 4H).

Preparation of 3,5-Diamino-N-(N-{4-[4-(3-aminopropoxy)naphthalen-1-yl]butyl}carbamimidoyl)-6-chloropyrazine-2-carboxamide Methanesulfonic Acid Salt (72)

To a solution of carboxamide 71 (120 mg, 0.247 mmole) in EtOH (10 mL) was added methanesulfonic acid (48 mg, 0.495 mmole) at room temperature and the reaction mixture was stirred for 15 min. The solvent was removed in vacuo. The residue was dissolved in water (10 mL) and lyophilized to afford methanesulfonic acid salt 72 (160 mg, 95%) as a yellow solid: $^1$H NMR (300 MHz, DMSO-d$_6$) δ 10.44 (s, 1H), 9.15 (br s, 1H), 8.86 (br s, 1H), 8.72 (br s, 1H), 8.22 (dd, J=8.1, 0.9, Hz, 1H), 8.03 (d, J=8.1 Hz, 1H), 7.80 (br s, 4H), 7.61-7.49 (m, 3H), 7.42 (br s, 2H), 7.28 (d, J=7.8 Hz, 1H), 6.89 (d, J=7.8 Hz, 1H), 4.22 (t, J=5.7 Hz, 2H), 3.35 3.33 (m, 2H), 3.17 2.99 (m, 4H), 2.32 (s, 6H), 2.20-2.10 (m, 2H), 1.68 (br s, 4H); ESI-MS m/z 485 [C$_{23}$H$_{29}$ClN$_8$O$_2$+H]$^+$.

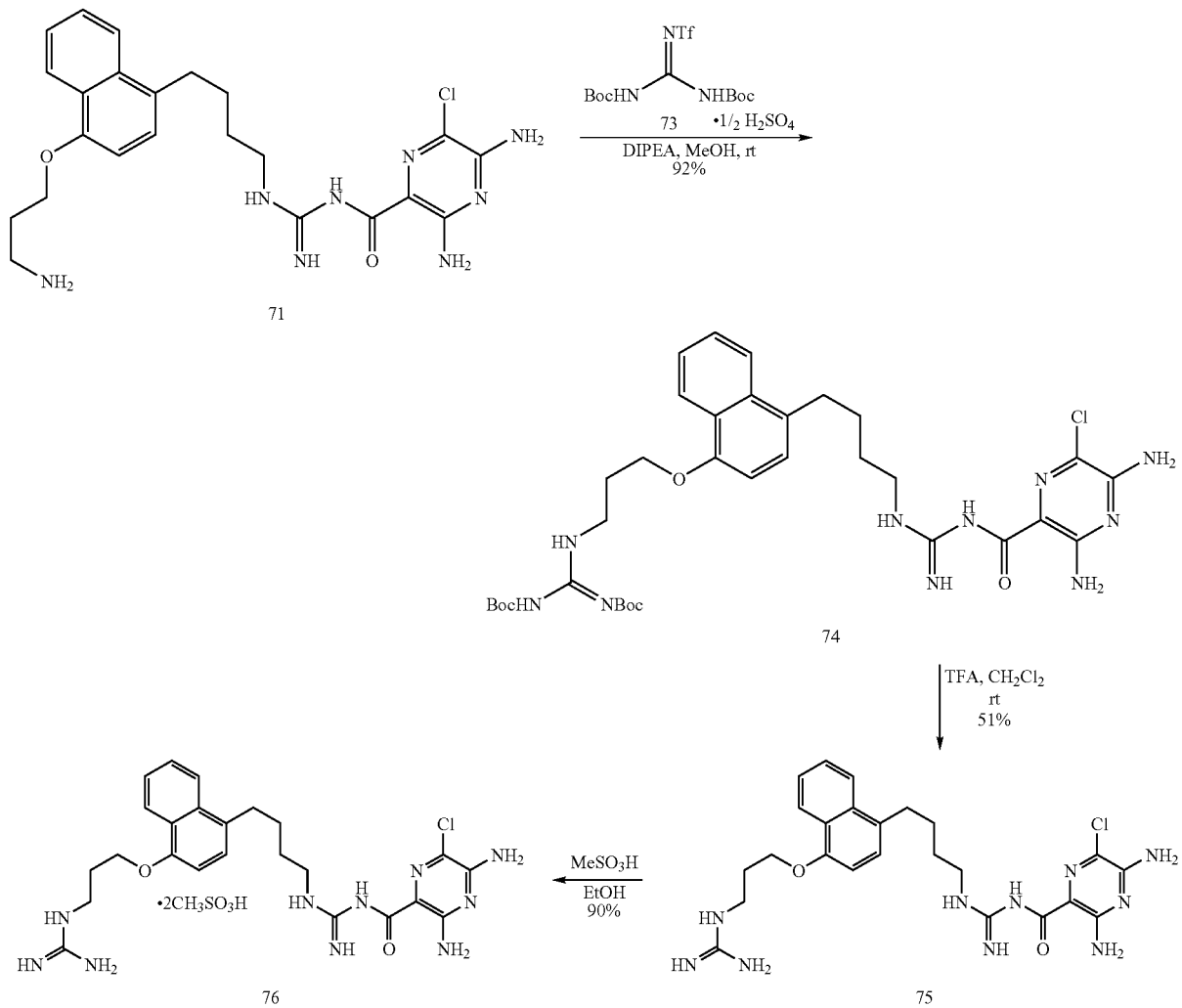

Preparation of Compound (74)

To a solution of amine 71 (60 mg, 0.12 mmole) and Goodman's reagent 73 (100 mg, 0.19 mmole) in MeOH (10 mL) was added diisopropylethylamine (0.2 mL, 1.0 mmole) at room temperature. The reaction mixture was stirred for 6 h and then concentrated. The residue was dissolved in $CHCl_3$ (100 mL) and washed with saturated $NaHCO_3$ (2×100 mL). The organic layer was dried over $MgSO_4$, filtered, and concentrated. The residue was purified by column chromatography (silica gel, 90:9:1 $CHCl_3/CH_3OH/NH_4OH$) to afford 74 (82 mg, 92%) as a light yellow solid: $^1$H NMR (300 MHz, $CD_3OD$) δ 8.26 (dd, J=8.1, 0.9 Hz, 1H), 7.96 (d, J=8.1 Hz, 1H), 7.48 (td, J=6.6, 1.2 Hz, 1H), 7.41 (td, J=6.9, 1.2 Hz, 1H), 7.19 (d, J=7.8 Hz, 1H), 6.77 (d, J=7.8 Hz, 1H), 4.19 (t, J=5.7 Hz, 2H), 3.65 (t, J=6.6 Hz, 2H), 3.25 (t, J=6.6 Hz, 2H), 3.01 (t, J=7.2 Hz, 2H), 2.22 2.14 (m, 2H), 1.82-1.65 (m, 4H), 1.41 (s, 9H), 1.42 (s, 9H).

Preparation of Compound (75)

To a solution of compound 74 (130 mg, 0.18 mmole) in $CH_2Cl_2$ (20 mL) was added dropwise trifluoroacetic acid (2.5 mL) at room temperature. The reaction mixture was stirred for 6 h and the solvent was removed in vacuo. The residue was dissolved in water (10 mL) and the solution was basified to pH 10 with 2 N NaOH which resulted in the precipitation of crude 75. Compound 75 was collected by filtration and purified by column chromatography (silica gel, 6:3:1 $CHCl_3/CH_3OH/NH_4OH$) to afford compound 75 (48 mg, 51%) as a light yellow solid: $^1$H NMR (300 MHz, $CD_3OD$) δ 8.27 (dd, J=8.1, 0.9 Hz, 1H), 8.01 (d, J=8.1 Hz, 1H), 7.53 (td, J=6.9, 1.5 Hz, 1H), 7.45 (td, J=6.9, 1.2 Hz, 1H), 7.26 (d, J=7.8 Hz, 1H), 6.85 (d, J=7.8 Hz, 1H), 4.24 (t, J=6.0 Hz, 2H), 3.51 (t, J=6.9 Hz, 2H), 3.35-3.33 (m, 2H), 3.08 (t, J=6.9 Hz, 2H), 2.24-2.19 (m, 2H), 1.84-1.80 (m, 4H).

Preparation of Methanesulfonic Acid Salt (76)

To a solution of compound 75 (48 mg, 0.09 mmole) in EtOH (5 mL) was added $CH_3SO_3H$ (17.5 mg, 0.18 mmole) at room temperature and the reaction mixture was stirred for 15 min. The solvent was removed in vacuo. The residue was dissolved in water (5 mL) and lyophilized to afford methanesulfonic salt 76 (60 mg, 90%) as a yellow solid: mp 85-87° C.; $^1$H NMR (300 MHz, DMSO-$d_6$) δ 10.44 (s, 1H), 9.15 (br s, 1H), 8.86 (br s, 1H), 8.70 (br s, 1H), 8.24 (dd, J=8.1, 1.5 Hz, 1H), 8.03 (d, J=8.4 Hz, 1H), 7.66-7.42 (m, 6H), 7.42 (br s 2H), 7.28 (d, J=6.9 Hz, 2H), 7.10 (s, 1H), 6.90 (t, J=6.0 Hz, 2H), 4.18 (t, J=6.0 Hz, 2H), 3.43-3.33 (m, 4H), 3.01 (t, J=6.9 Hz, 2H), 2.33 (s, 9H), 2.11-2.06 (In, 2H), 1.68 (br s, 4H); ESI-MS m/z 528 $[C_{24}H_{31}ClN_{10}O_2+H]^+$.

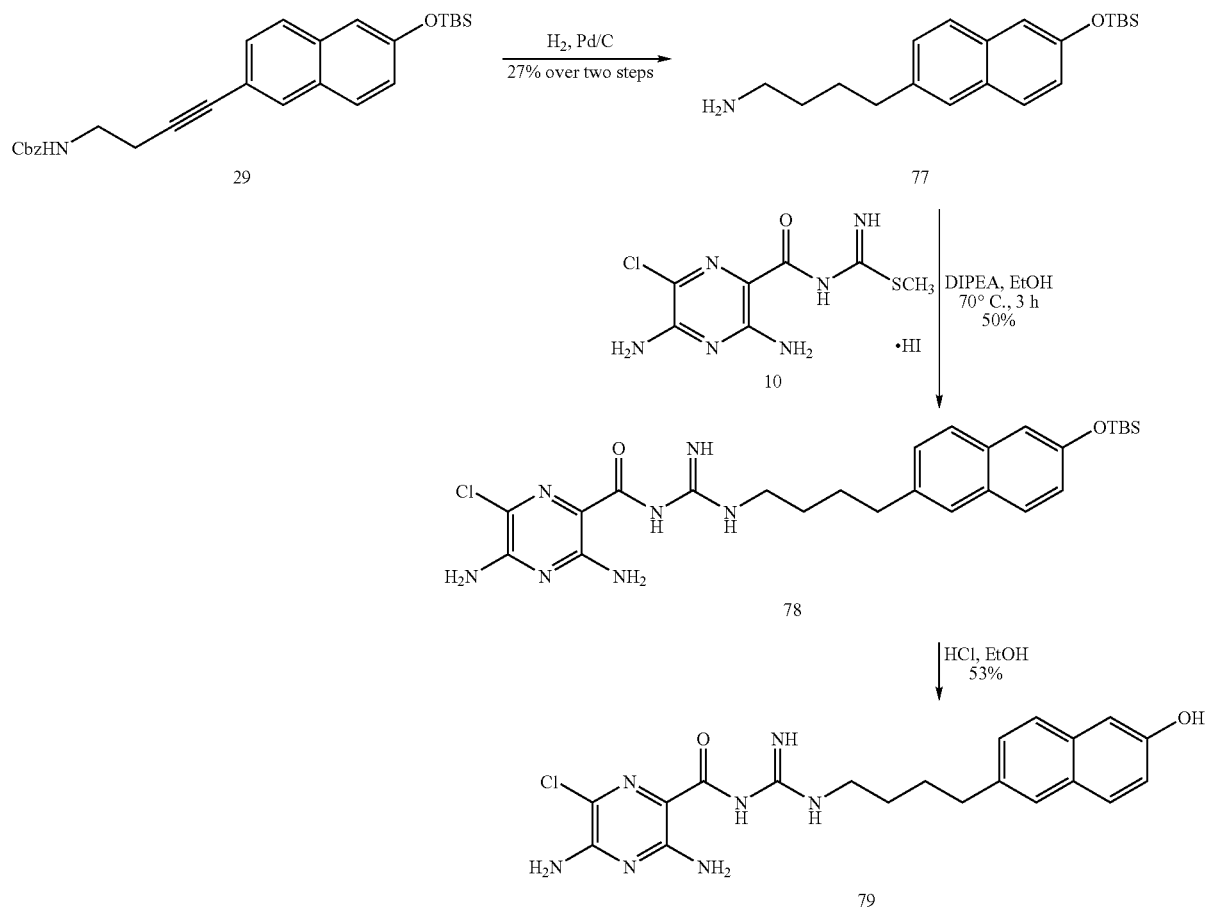

Scheme 13

Preparation of 4-[6-(tert-Butyldimethylsilyloxy) naphthalen-2-yl]butan-1-amine (77)

A suspension of crude 29 (900 mg) and 10% Pd/C (400 mg) in MeOH (50 mL) was subject to hydrogenation conditions (1 atm) for 6 h at room temperature. The reaction mixture was filtered through a plug of diatomaceous earth and the plug was washed with MeOH. The filtrate was concentrated in vacuo and the residue was purified by column chromatography (silica gel, 80:18:2 CHCl$_3$/CH$_3$OH/NH$_4$OH) to afford amine 77 (405 mg, 27% over two steps) as a white solid: $^1$H NMR (300 MHz, CDCl$_3$) δ 7.62 (t, J=8.9, 2H), 7.52 (br s, 1H), 7.26 (dd, J=8.4, 1.7 Hz, 1H), 7.15 (d, J=2.2 Hz, 1H), 7.04 (dd, J=8.8, 2.5 Hz, 1H), 3.03-2.37 (br s, 1H), 2.74 (t, J=7.5 Hz, 2H), 1.78-1.65 (m, 2H), 1.58-1.47 (m, 2H), 1.01 (s, 9H), 0.23 (s, 6H).

Preparation of 3,5-Diamino-N-(N-{4-[6-(tert-butyldimethylsilyloxy)naphthalen-2-yl]butyl}carbamimidoyl)-6-chloropyrazine-2-carboxamide (78)

To a solution of amine 77 (337 mg, 1.02 mmole) and methyl 3,5-diamino-6-chloropyrazine-2-carbonylcarbamimidothioate (10, 596 mg, 1.53 mmole) in EtOH (20 mL) was added diisopropylethylamine (1.06 mL, 6.13 mmole) at room temperature. The reaction mixture was heated at 70° C. in a sealed tube for 6 h, then cooled to room temperature, and concentrated to dryness. The residue was purified by column chromatography (silica gel, 80:18:2 CHCl$_3$/CH$_3$OH/NH$_4$OH) to afford carboxamide 78 (280 mg, 50%) as a light yellow solid: $^1$H NMR (300 MHz, CD$_3$OD) δ 7.67 (d, J=9.2 Hz, 1H), 7.63 (d, J=8.6 Hz, 1H), 7.57 (br s, 1H), 7.30 (d, J=8.1 Hz, 1H), 7.14 (br s, 1H), 7.03 (dd, J=9.2, 1.7 Hz, 1H), 3.30 (m, 2H), 2.81 (t, J=7.0 Hz, 2H), 1.95-1.62 (m, 4H), 1.03 (s, 9H), 0.24 (s, 6H).

Preparation of 3,5-Diamino-6-chloro-N-{N-[4-(6-hydroxynaphthalen-2-yl)butyl]carbamimidoyl}pyrazine-2-carboxamide (79)

To a solution of carboxamide 78 (24 mg, 0.05 mmol) in absolute ethanol (5 mL) was added dropwise 1 N HCl (2 mL) at room temperature and the mixture was stirred for 12 h. The reaction mixture was neutralized with saturated NaHCO$_3$ and compound 79 precipitated out. Compound 79 was collected by filtration and washed with water (2×10 mL) and hexanes (2×10 mL) to afford 3,5-diamino-6-chloro-N-{N-[4-(6-hydroxynaphthalen-2-yl)butyl]carbamimidoyl}pyrazine-2-carboxamide (79, 10 mg, 53%), after air-drying, as a light yellow solid: $^1$H NMR (300 MHz, CD$_3$OD) δ 7.63-7.53 (m, 3H), 7.26 (dd, J=8.3, 1.5 Hz, 1H), 7.07-6.98 (m, 2H), 3.36-3.30 (m, 2H), 2.80

Scheme 14
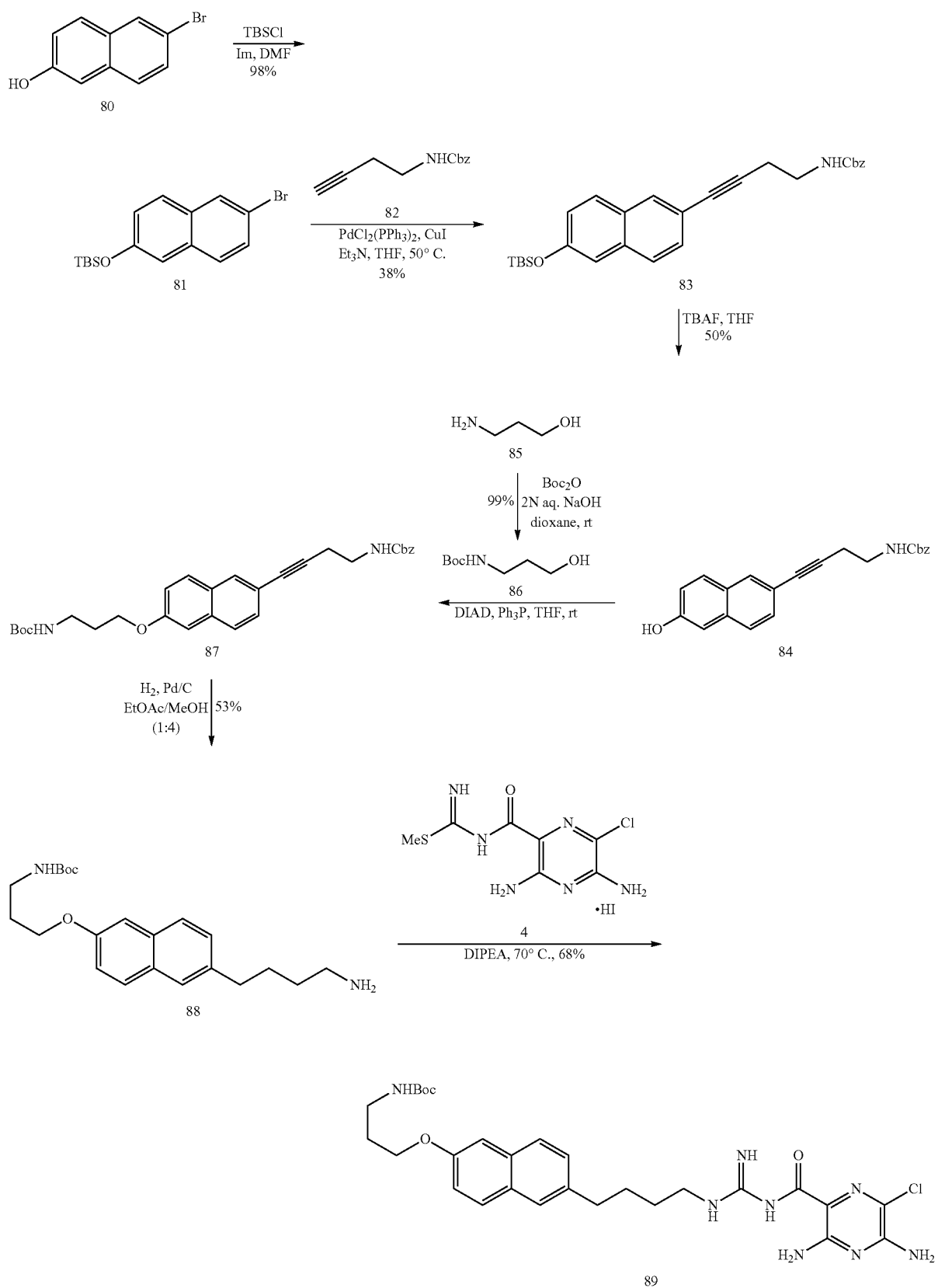

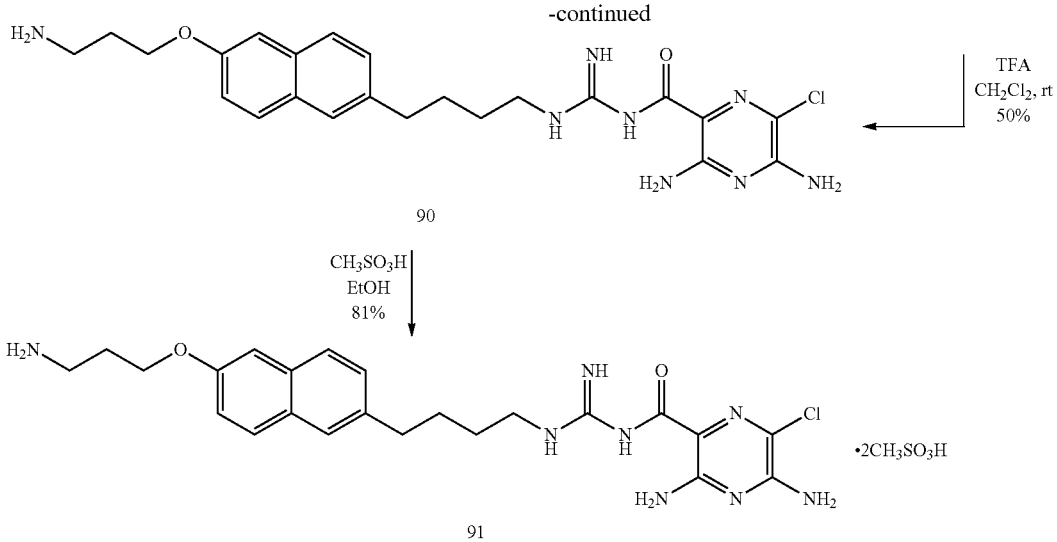

Preparation of (6-Bromonaphthalen-2-yloxy)(tert-Butyl)dimethylsilane (81)

A solution of 6-bromonaphthalen-2-ol (12.0 g, 53.7 mmol) and imidazole (6.0 g, 79.5 mmol) in DMF (12.0 mL) was added t-butyldimethylsilyl chloride (TBDMSCl) (9.0 g, 59.0 mmol) in one portion at 0° C. The mixture was allowed to warm to room temperature and stirred for 3 h. The reaction mixture was partitioned between EtOAc (500 mL) and water (300 mL). The aqueous layer was separated and extracted with EtOAc (2×100 mL) and the combined organic extracts were washed with brine (300 mL), dried over $Na_2SO_4$, filtered, and concentrated. The residue was purified by column chromatography (silica gel, hexanes) to afford (6-bromonaphthalen-2-yloxy)(tert-butyl)dimethylsilane (81, 18.0 g, 98%) as a white solid: $^1$H NMR (300 MHz, $CDCl_3$) δ 7.91 (d, J=1.8 Hz, 1H), 7.64 (d, J=8.7 Hz, 1H), 7.56 (d, J=8.7 Hz, 1H), 7.48 (dd, J=8.7, 1.8 Hz, 1H), 7.15 (d, J=2.4 Hz, 1H), 7.09 (dd, J=9.0, 2.4 Hz, 1H), 1.01 (s, 9H), 0.24 (s, 6H).

Preparation of Benzyl 4-[6-(tert-butyldimethylsilyloxy)naphthalen-2-yl]but-3-ynylcarbamate (83)

A solution of (6-bromonaphthalen-2-yloxy)(tert-butyl)dimethylsilane (81, 16.1 g, 47.7 mmol), benzyl but-3-ynylcarbamate (82, 9.0 g, 47.7 mmol), and triethylamine (95 mL) in anhydrous THF (100 mL) was cooled to −78° C. and degassed with argon. The mixture was warmed to room temperature and dichlorobis(triphenylphosphine)palladium(II) (3.3 g, 4.8 mmol) and CuI (1.8 g, 9.6 mmol) were added rapidly in one portion under argon. The mixture was heated at 50° C. for 12 h. The reaction mixture was filtered through a plug of diatomaceous earth and the filtrate was concentrated. The residue was purified by column chromatography (silical gel, 10:1 hexanes/EtOAc) to afford carbamate 83 (8.5 g, 38%) as a thick brown oil: $^1$H NMR (300 MHz, $CDCl_3$) δ 7.83 (s, 1H), 7.65 (d, J=9.0 Hz, 1H), 7.60 (d, J=8.7 Hz, 1H), 7.39-7.29 (m, 6H), 7.13 (d, J=2.1 Hz, 1H), 7.07 (dd, J=8.7, 2.4 Hz, 1H), 5.17 (br s, 1H), 5.13 (s, 2H), 3.46 (q, J=6.3 Hz, 2H), 2.67 (t, J=6.3 Hz, 2H), 1.01 (s, 9H), 0.25 (s, 6H).

Preparation of Benzyl 4-(6-hydroxynaphthalen-2-yl)but-3-ynylcarbamate (84)

To a solution of benzyl 4-[6-(tert-butyldimethylsilyloxy) naphthalen-2-yl]but-3-ynylcarbamate (83, 2.5 g, 5.44 mmol) in anhydrous THF (25 mL) at 0° C. was added dropwise tetrabutylammonium fluoride (1 M in THF, 6.0 mL) and the mixture was stirred for 2 h at room temperature. The resulting solution was concentrated in vacuo and the residue was purified by column chromatography (silica gel, 95:5 $CH_2Cl_2$/MeOH) to afford carbamate 84 (2.0 g, 50%) as a pale yellow solid: $^1$H NMR (300 MHz, $CDCl_3$) δ 7.82 (s, 1H), 7.67 (d, J=9.6 Hz, 1H), 7.58 (d, J=8.4 Hz, 1H), 7.37-7.29 (m, 6H), 7.11-7.08 (m, 2H), 5.30 (br s, 2H), 5.14 (s, 2H), 3.48 (q, J=6.3 Hz, 2H), 2.68 (t, J=6.6 Hz, 2H).

Preparation of tert-Butyl 3-hydroxypropylcarbamate (66)

To a solution of 3-aminopropanol (55, 5.0 g, 67 mmol) in dioxane/2 N NaOH (1: 1, 100 mL) was added a solution of di-tert-butyl dicarbonate (17.0 g, 80 mmol) in dioxane (10 mL) at 0° C. The reaction mixture was warmed to room temperature and stirred for 1 h. The mixture was first acidified to pH I with concentrated HCl and then neutralized to pH 7 with 2 N NaOH. The mixture was then extracted with EtOAc (3×200 mL). The combined organic layers were dried over $MgSO_4$ and concentrated. The residue was purified by column chromatography (silica gel, 3:1 hexanes/EtOAc) to afford tert-butyl 3-hydroxypropylcarbamate (86, 11.7 g, 99%) as a light yellow oil: $^1$H NMR (300 MHz, $CDCl_3$) δ 4.80 (br s, 1H), 3.66 (q, J=5.7 Hz, 2H), 3.33 (q, J=6.3 Hz, 2H), 2.97 (br s, 1H), 1.71-1.63 (m, 2H), 1.45 (s, 9H).

Preparation of Boc-Protected Carbamate (87)

Diisopropylazodicarboxylate (557 mg, 2.75 mmol) was added dropwise to a solution of 4-(6-hydroxynaphthalen-2-yl)but-3-ynylcarbamate (84, 638 mg, 1.83 mmol), tert-butyl 3-hydroxypropylcarbamate (86, 355 mg, 2.01 mmol), and triphenylphosphine (980 mg, 3.70 mmol) in anhydrous THF (20 mL) at 0° C. The reaction mixture was warmed to room temperature and stirred for 12 h. The reaction mixture was concentrated and the residue was purified by column chromatography (silica gel, 2:1 hexanes/EtOAc) to afford a mixture of ether 87 and the hydrazine by-product (4.0 g) which was used in the next step without further purification.

Preparation of tert-Butyl 3-[6-(4-aminobutyl)naphthalen-2-yloxy]propylcarbamate (88)

A suspension of 87 (4.0 g) and 10% Pd/C (500 mg) in MeOH/EtOAc (4:1, 350 mL) was subjected to hydrogenation conditions (1 atm) for 6 h at room temperature. The reaction mixture was filtered through a plug of diatomaceous earth and the plug was washed with MeOH. The filtrate was concentrated in vacuo and the residue was purified by column chromatography (silica gel, 90:9:1 $CHCl_3/CH_3OH/NH_4OH$) to afford carbamate 88 (437 mg, 64% over two steps) as a white solid: $^1$H NMR (300 MHz, $CD_3OD$) δ 7.70 (dd, J=9.0 Hz, 2H), 7.59 (s, 1H), 7.34 7.31 (m, 1H), 7.21 (d, J=2.4 Hz, 1H), 7.12 (d, J=9.0, 2.4 Hz, 1H), 4.13 (t, J=6.0 Hz, 2H), 3.30 (t, J=6.3 Hz, 2H), 2.91-2.80 (m, 4H), 2.03-1.99 (m, 2H), 1.90-1.60 (m, 4H), 1.46 (s, 9H).

Preparation of tert-Butyl 3-(6-{4-[3-(3,5-diamino-6-chloropyrazine-2-carbonyl)guanidino]butyl}naphthalen-2-yloxy)propylcarbamate (89)

To a solution of carbamate 88 (500 mg, 1.34 mmol) and methyl 3,5-diamino-6-chloropyrazine-2-carbonylcarbamimidothioate (10, 790 mg, 2.01 mmol) in EtOH (30 mL) was added DIPEA (1.75 mL, 9.39 mmol) at room temperature. The reaction mixture was heated at 70° C. in a sealed tube for 2 h, then cooled to room temperature, and concentrated in vacuo. The residue was purified by column chromatography (silica gel, 90:9:1 $CHCl_3/CH_3OH/NH_4OH$) to afford carbamate 89 (660 mg, 84%) as a yellow solid: $^1$H NMR (300 MHz, $CD_3OD$) δ 7.65 (d, J=7.5 Hz, 2H), 7.56 (s, 1H), 7.31 (dd, J=8.4, 1.5 Hz, 1H), 7.16 (d, J=2.4 Hz, 1H), 7.08 (dd, J=8.7, 2.4 Hz, 1H), 4.10 (t, J=6.3 Hz, 2H), 2.81 (t, J=6.6 Hz, 2H), 2.01-1.97 (m, 2H), 1.83-1.60 (m, 4H), 1.43 (s, 9H).

Preparation of 3,5-Diamino-N-(N-{4-[6-(3-aminopropoxy)naphthalen-2-yl]butyl}carbamimidoyl-6-chloropyrazine-2-carboxamide (90)

To a solution of compound 89 (725 mg, 1.24 mmol) in $CH_2Cl_2$ (45 mL) was added dropwise trifluoroacetic acid (6.0 mL) at room temperature. The reaction mixture was stirred for 4 h and the solvent was removed in vacuo. The residue was dissolved in water (10 mL) and the solution was basified to pH 7 with saturated $NaHCO_3$ which resulted in the precipitation of crude 20. This was filtered and purified by column chromatography (silica gel, 80:18:2 $CHCl_3/CH_3OH/NH_4OH$) to afford compound 90 (289 mg, 48%) as a light yellow solid: $^1$H NMR (300 MHz, $CD_3OD$) δ 7.65 (d, J=7.5 Hz, 2H), 7.56 (s, 1H), 7.31 (dd, J=8.4, 1.5 Hz, 1H), 7.16 (d, J=2.4 Hz, 1H), 7.08 (dd, J=8.7, 2.4 Hz, 1H), 4.10 (t, J=−6.3 Hz, 2H), 2.81 (t, J=6.6 Hz, 2H), 2.01-1.97 (m, 2H), 1.83-1.60 (m, 4H).

Preparation of 3,5-Diamino-N-(N-{4-[6-(3-aminopropoxy)naphthalen-2-yl]butyl}carbamimidoyl-6-chloropyrazine-2-carboxamide Methanesulphonate Salt (91)

To a solution of 3,5-diamino-N-(N-{4-[6-(3-aminopropoxy)naphthalen-2-yl]butyl}carbamimidoyl-6-chloropyrazine-2-carboxamide (20, 30 mg, 0.062 mmol) in EtOH (5 mL) was added methanesulphonic acid (12.5 mg, 0.13 mmol) at room temperature and the reaction mixture was stirred for 15 min. The solution was concentrated and the residue was azeotroped with MeOH. The residue was dissolved in $H_2O$/MeOH (8:2, 10 mL) and lyophilized to afford methanesulphonate salt 91 (33 mg, 79%) as a yellow solid: $^1$H NMR (300 MHz, DMSO-$d_6$) δ 10.4 (s, 1H), 9.13 (br s, 1H), 8.85 (br s, 1H), 8.74 (br s, 1H), 7.76-7.71 (m, 5H), 7.62 (s, 1H), 7.50 7.33 (m, 3H), 7.26 (s, 1H), 7.13 (dd, J=8.8, 2.2 Hz, 1H), 4.15 (t, J=6.0 Hz, 5H), 3.32-3.04 (m, 2H), 3.01-2.97 (m, 2H), 2.77-2.72 (m, 2H), 2.38 (s, 11H), 2.10-2.01 (m, 2H), 1.74-1.59 (m, 4H); ESI-MS m/z 485 $[C_{23}H_{29}ClN_8O_2+H]^+$.

Scheme 15
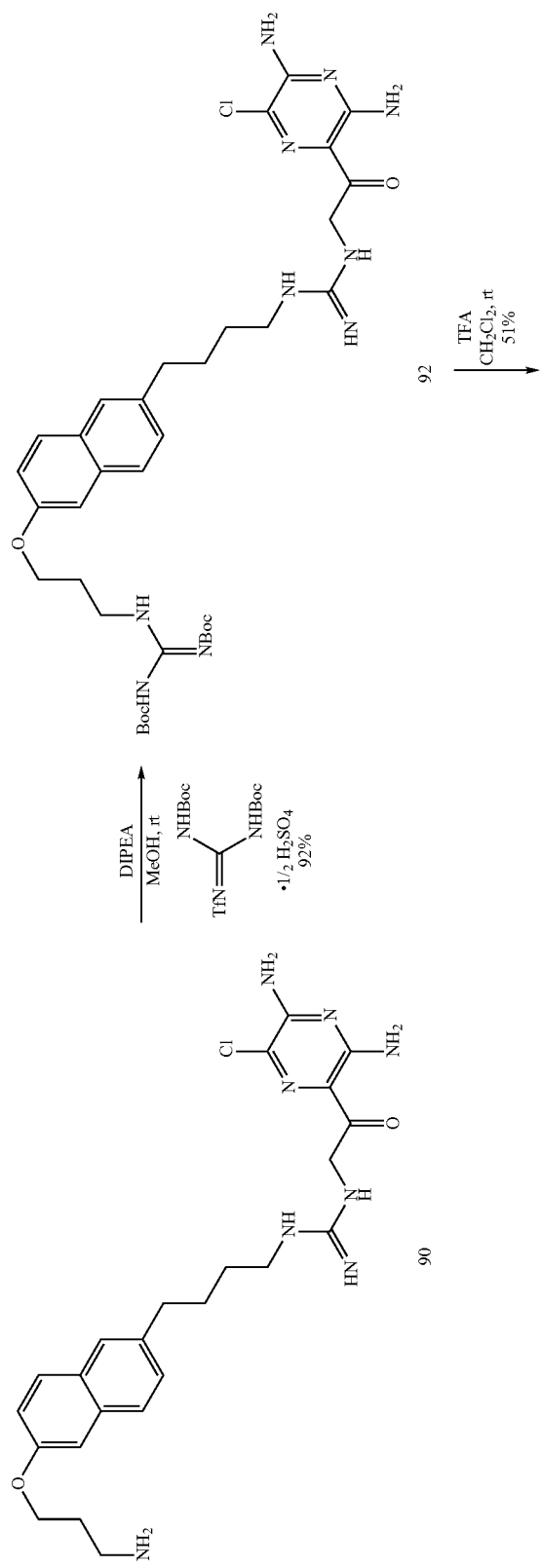

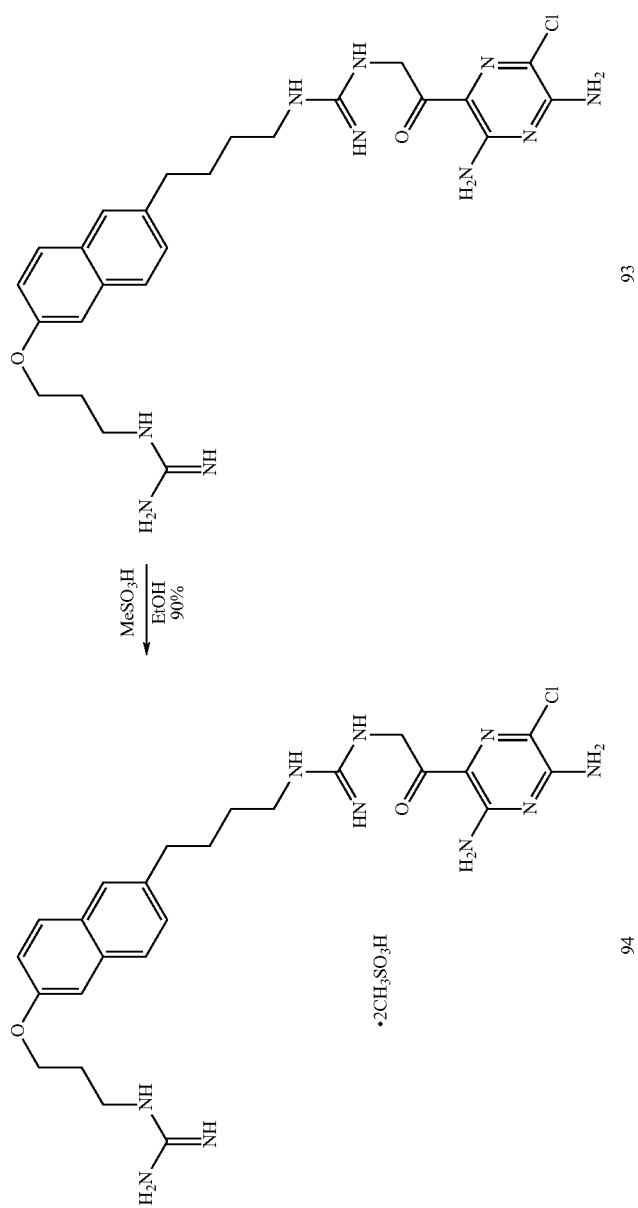

Preparation of Boc-Urea 92

To a solution of amine 90 (300 mg, 0.62 mmol) and Goodman's reagent (392 mg, 1.00 mmol) in MeOH (60 mL) was added DIPEA (0.45 mL, 2.5 mmol) at room temperature. The reaction mixture was stirred for 7 h and then concentrated. The residue was dissolved in CHCl$_3$ (200 mL) and washed with saturated NaHCO$_3$ (2×100 mL). The organic layer was dried over MgSO$_4$, filtered, and concentrated. The residue was purified by column chromatography (silica gel, 90:9:1 CHCl$_3$/CH$_3$OH/NH$_4$OH) to afford Boc-urea 92 (280 mg, 62%) as a light yellow solid: $^1$H NMR (300 MHz, CD$_3$OD) δ 7.67 (t, J=7.8 Hz, 2H), 7.57 (s, 1H), 7.31 (d, J=8.1 Hz, 1H), 7.19 (s, 2H), 4.18 (t, J=5.4 Hz, 2H), 3.62 (t, J=6.0 Hz, 2H), 2.82 (t, J=6.3 Hz, 2H), 2.12 (t, J=5.7 Hz, 2H), 1.85-1.70 (m, 4H), 1.54 (s, 9H), 1.45 (s, 9H).

Preparation of Urea 93

To a solution of Boc-urea 92 (280 mg, 0.39 mmol) in CH$_2$Cl$_2$ (30 mL) was added dropwise trifluoroacetic acid (6.0 mL) at room temperature. The reaction mixture was stirred for 4 h and the solvent was removed in vacuo. The residue was dissolved in water (10 mL) and the solution was basified to pH 10 with 2 N NaOH which resulted in the precipitation of crude 23. This was filtered and purified by column chromatography (silica gel, 6:3:1 CHCl$_3$/CH$_3$OH/NH$_4$OH) to afford urea 93 (99 mg, 49%) as a light yellow solid: 1 H NMR (300 MHz, CD$_3$OD) δ 7.66 (dd, J=4.5, 8.1 Hz, 2H), 7.57 (s, 1H), 7.32 (d, J=8.1 Hz, 1H), 7.20 (s, 1H), 7.10 (dd, J=2.4, 8.7 Hz, 1H), 4.17 (t, J=5.7 Hz, 2H), 3.43 (t, J=6.6 Hz, 2H), 2.82 (t, J=6.3 Hz, 2H), 2.16-2.08 (m, 2H), 1.84-1.70 (m, 4H).

Preparation of Methanesulphonate Salt 94

To a solution of compound 93 (99 mg, 0.19 mmol) in EtOH (6 mL) was added CH$_3$SO$_3$H (36 mg, 0.40 mmol) at room temperature and the reaction mixture was stirred for 15 min. The solvent was removed in vacuo. The residue was dissolved in water (5 mL) and lyophilized to afford methanesulphonate salt 94 (115 mg, 85%) as a yellow solid: $^1$H NMR (300 MHz, DMSO-d$_6$) δ 10.42 (s, 1H), 9.12 (br s, 1H), 8.85 (br s, 1H), 8.68 (br s, 1H), 7.76-6.90 (m, 16H), 4.10 (t, J=5.4 Hz, 2H), 3.31 (d, J=5.4 Hz, 4H), 2.74-2.71 (m, 2H), 2.30 (s, 6H), 2.07-1.96 (m, 2H), 1.71-1.59 (m, 4H); ESI-MS m/z 527 $[C_{24}H_{31}ClN_{10}O_2+H]^+$.

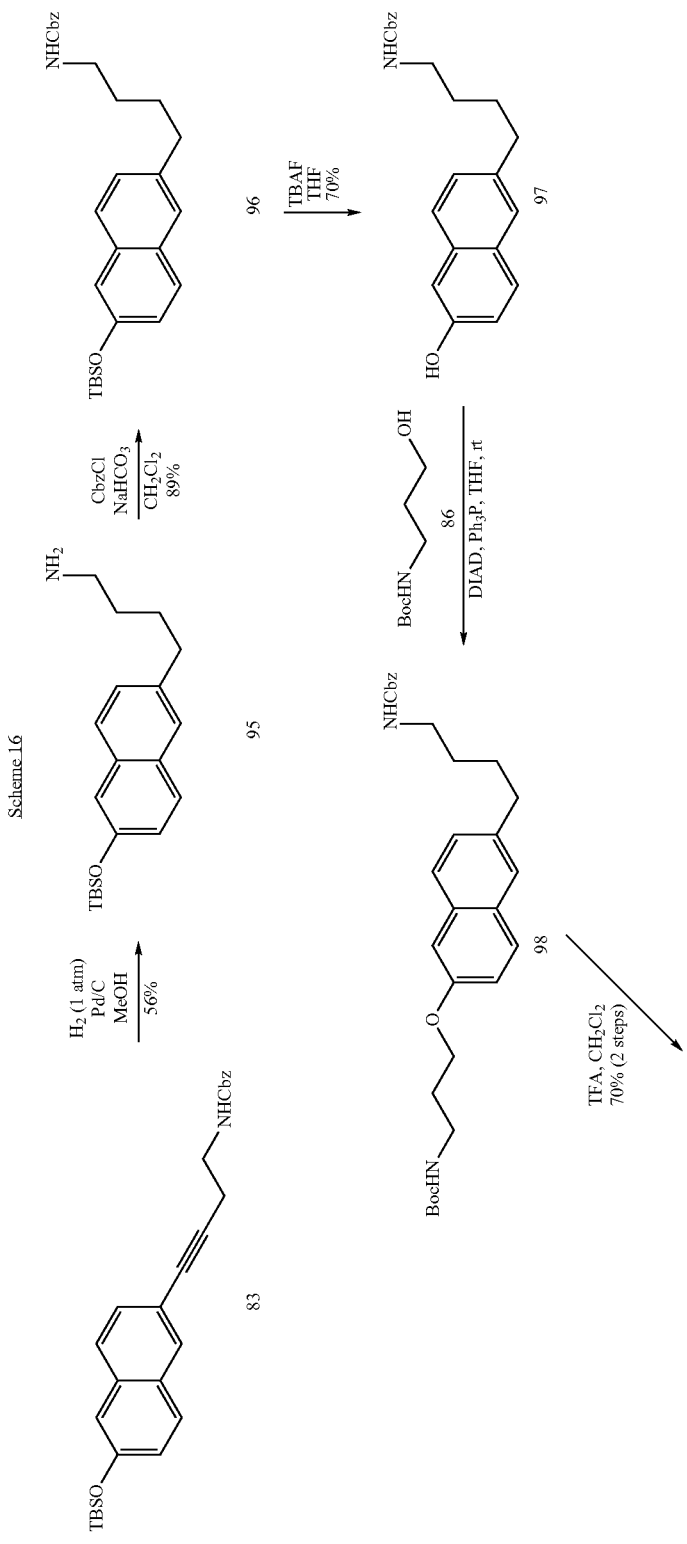

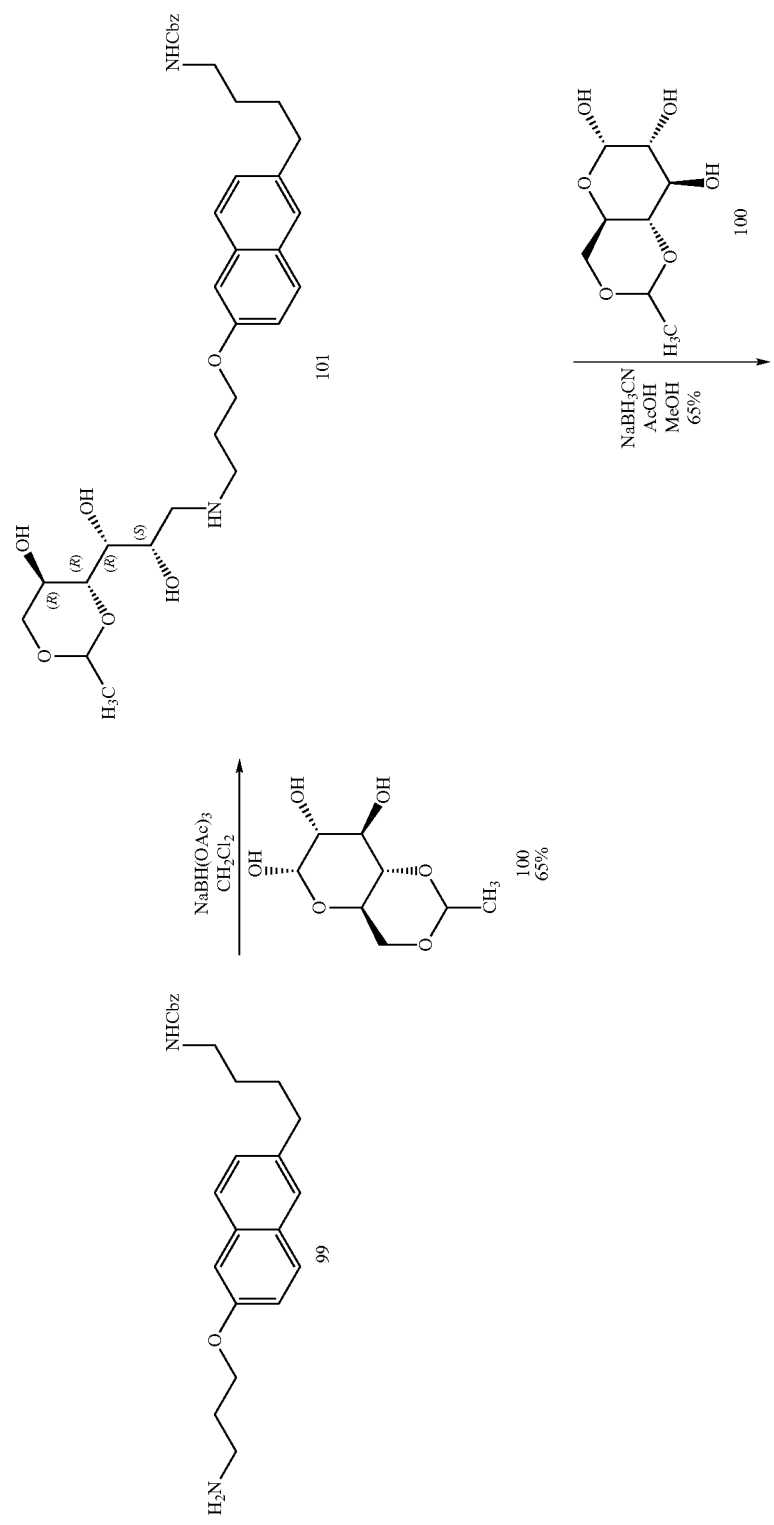

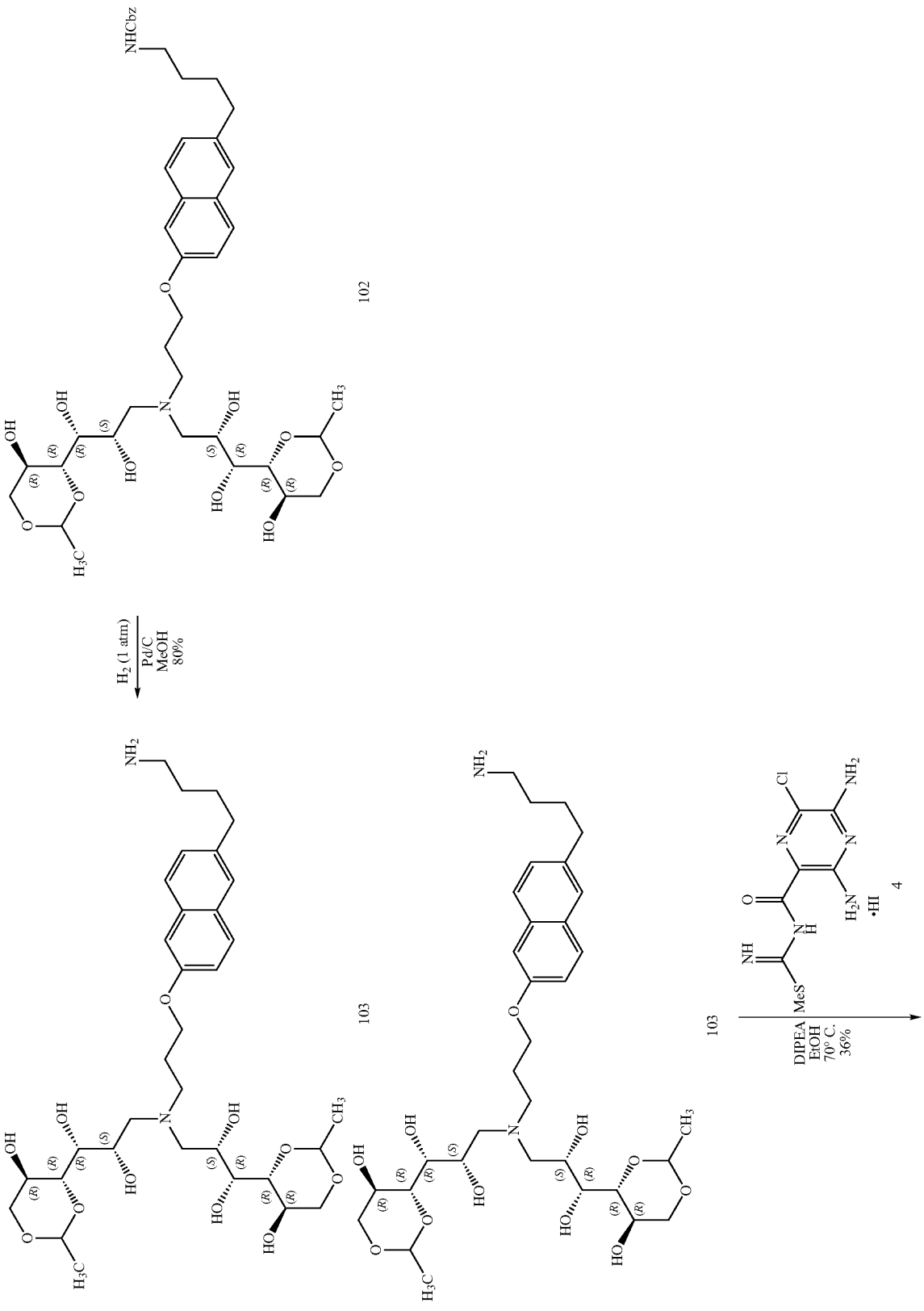

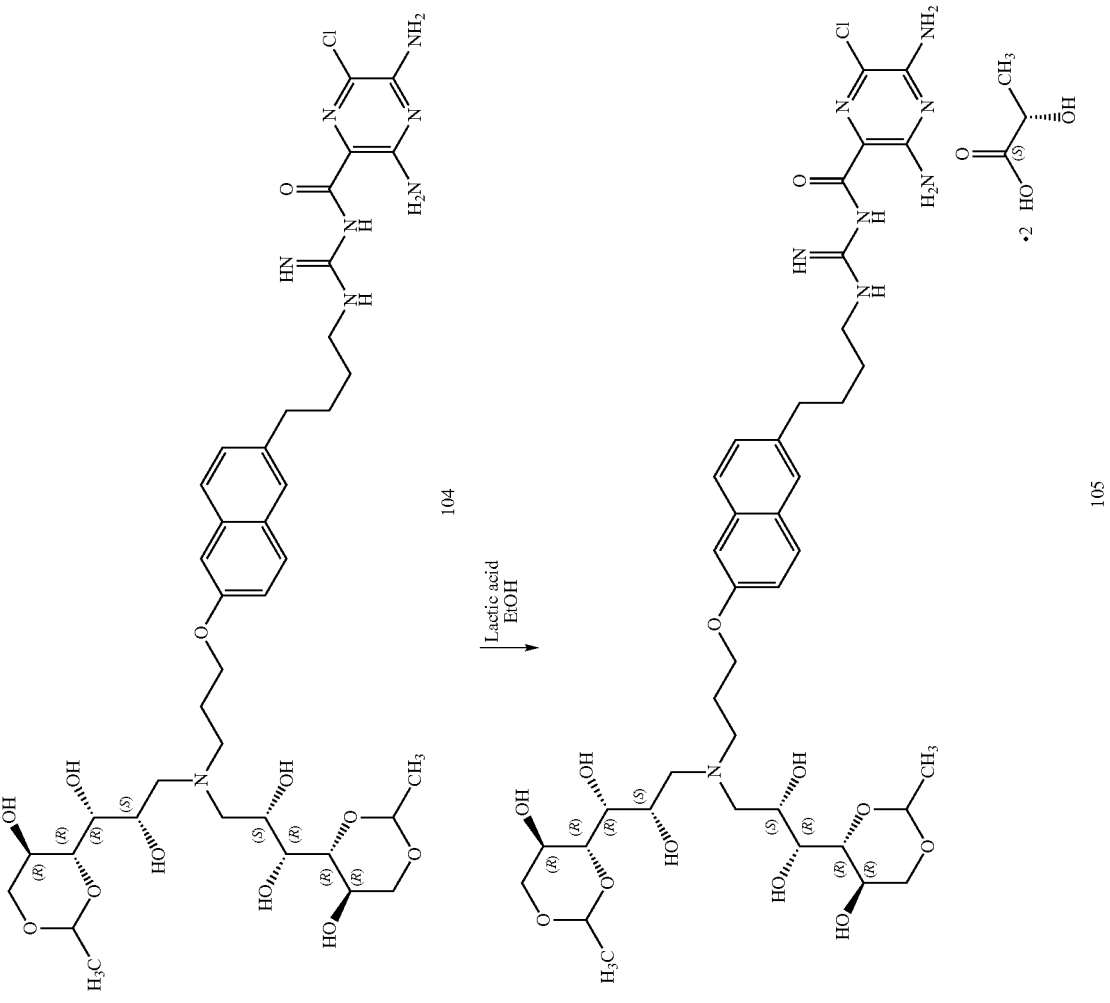

Preparation of Benzyl 4-[6-(tert-butyldimethylsilyloxy)naphthalen-2-yl]butan-1-amine (95)

A suspension of 83 (8.0 g, 17.41 mmol) and 10% Pd/C (3.6 g) in MeOH (240 mL) was subjected to hydrogenation conditions (1 atm) for 6 h at room temperature. The reaction mixture was filtered through a plug of diatomaceous earth and the plug was washed with MeOH. The filtrate was concentrated in vacuo and the residue was purified by column chromatography (silica gel, 90:9:1 $CHCl_3/CH_3OH/NH_4OH$) to afford amine 95 (3.2 g, 56%) as a yellow solid: $^1$H NMR (300 MHz, $CD_3OD$) δ 7.64 (d, J=6.3 Hz, 1H), 7.60 (s, 1H), 7.55 (s, 1H), 7.30 (d, J=1.5 Hz, 1H), 7.15 (s, 1H), 7.03 (dd, J=8.9 Hz, 2.3 Hz, 1H), 2.76 (t, J=7.4 Hz, 2H), 2.70 (t, J=7.2 Hz, 2H), 1.79-1.69 (m, 2H), 1.59-1.49 (m, 2H), 1.04 (s, 9H), 0.25 (s, 6H).

Preparation of Benzyl 4-[6-(tert-butyldimethylsilyloxy)naphthalen-2-yl]carbamate (96)

To a solution of amine 95 (3.2 g, 9.7 mmol) in $CH_2Cl_2$/saturated aqueous $NaHCO_3$ (1:1, 135 mL), benzyl chloroformate (2.1 mL) was added dropwise at room temperature and the reaction mixture was stirred for 2 h. The mixture was concentrated, the residue was dissolved in EtOAc (500 mL), and the solution was washed with water (300 mL) and brine (300 mL). The organic layer was dried over $Na_2SO_4$, filtered, and concentrated. The residue was purified by column chromatography (silica gel, 4:1 hexanes/EtOAc) to afford carbamate 96 (4.0 g, 89%) as a light yellow solid: $^1$H NMR (300 MHz, $CD_3OD$) δ 7.64 (d, J=6.3 Hz, 1H), 7.60 (s, 1H), 7.55 (s, 1H), 7.37 7.26 (m, 6H), 7.15 (s, 1H), 7.03 (dd, J=8.9 Hz, 2.3 Hz, 1H), 5.10 (s, 1H), 2.77 (t, J=7.4 Hz, 2H), 2.70 (t, J=7.2 Hz, 2H), 1.79-1.69 (m, 2H), 1.59-1.49 (m, 2H), 1.04 (s, 9H), 0.25 (s, 6H).

Preparation of Benzyl 4-[6-(hydroxynaphthalen-2-yl)]carbamate (97)

To a solution of carbamate 96 (4.0 g, 6.47 mmol) in THF (30 mL) was added dropwise tetrabutylammonium fluoride (1 M in THF, 7.2 mL, 7.2 mmol) at room temperature. The reaction mixture was stirred for 2 h and the solvent was removed in vacuo. The residue was purified by column chromatography (silica gel, 7:3 hexanes/EtOAc) to afford compound 97 (2.1 g, 70%) as a light yellow solid: $^1$H NMR (300 MHz, $CDCl_3$) δ 7.63 (d, J=8.7 Hz, 1H), 7.56 (d, J=8.4 Hz, 1H), 7.48 (s, 1H), 7.37-7.26 (m, 5H), 7.21 (dd, J=8.5 Hz, 1.3 Hz, 1H), 7.11 (d, J=2.1 Hz, 1H), 7.08 (d, J=2.4 Hz, 1H), 7.05 (d, J=2.4 Hz, 1H), 5.10 (s, 2H), 4.75 (br, 1H), 3.23 (q, J=6.5 Hz, 2H), 2.72 (t, J=7.5 Hz, 2H), 1.75-1.65 (m, 2H), 1.60-1.47 (m, 2H).

Preparation of Ether 98

Diisopropylazodicarboxylate (2.45 g, 12.0 mmol) was added dropwise to a solution of benzyl 4-(6-hydroxynaphthalen-2-yl)carbamate (97, 2.1 g, 6.0 mmol), tert-butyl 3-hydroxypropylcarbamate (86, 2.1 g, 12.0 mmol), and triphenylphosphine (4.8 g, 18.0 mmol) in anhydrous THF (63 mL) at 0° C. The reaction mixture was warmed to room temperature and stirred for 12 h. The reaction mixture was concentrated and the residue was purified by column chromatography (silica gel, 7:3 hexanes/EtOAc) to afford a mixture of ether 98 and the hydrazine by-product (3.0 g) which was used in the next step without further purification.

Preparation of Amine 29

To a solution of compound 98 (5.5 g, 11.0 mmol) in $CH_2Cl_2$ (350 mL) was added dropwise trifluoroacetic acid (84 mL) at room temperature. The reaction mixture was stirred for 2 h and the solvent was removed in vacuo. The residue was dissolved in $CHCl_3$ (300 mL) and washed with saturated aqueous $NaHCO_3$, the organic layer was dried over $MgSO_4$, filtered, concentrated in vacuo, and purified by column chromatography (silica gel, 90:9:1 $CHCl_3/CH_3OH/NH_4OH$) to afford compound 99 (1.74 g, 71% over two steps) as a light yellow solid: $^1$H NMR (300 MHz, $CD_3OD$) δ 7.65 (d, J=8.4 Hz, 2H), 7.53 (s, 1H), 7.31-7.26 (m, 6H), 7.19 (s, 1H), 7.08 (dd, J=8.7 Hz, 2.4 Hz, 1H), 5.05 (s, 2H), 4.17 (t, J=6.0 Hz, 2H), 3.15 (t, J=6.9 Hz, 2H), 2.96 (t, J=6.9 Hz, 2H), 2.73 (t, J=7.5 Hz, 2H), 2.09-2.00 (m, 2H), 1.80-1.65 (m, 2H), 1.59-1.49 (m, 2H).

Preparation of Benzyl 4-[6-(3-{(2S,3R)-2,3-dihydroxy-3-[(4R,5R)-5-hydroxy-2-methyl-1,3-dioxan-4-yl]propylamino}propoxy)naphthalene-2-yl]carbamate (101)

A solution of carbamate 99 (1.74 g, 4.28 mmol), triol 100 (922 mg, 4.28 mmol), and sodium triacetoxyborohydride (1.43 g, 6.42 mmol) in $CH_2Cl_2$ (18 mL) was stirred at room temperature for 8 h. The reaction mixture was concentrated to dryness and the residue was purified by column chromatography (silica gel, 86:12.5:1.5 $CH_2Cl_2/CH_3OH/NH_4OH$) to afford carbamate 101 (508 mg, 20%) as an white gummy solid: $^1$H NMR (300 MHz, $CD_3OD$) δ 7.65 (d, J=8.4 Hz, 2H), 7.53 (s, 1H), 7.31-7.26 (m, 6H), 7.19 (s, 1H), 7.11 (dd, J=9.0 Hz, 2.4 Hz, 1H), 5.05 (s, 2H), 4.67 (q, J=4.9 Hz, 1H), 4.18 (t, J=6.0 Hz, 2H), 4.07 3.94 (m, 2H), 3.82-3.74 (m, 2H), 3.46 (dd, J=9.3 Hz, 2.1 Hz, 1H), 3.37 (d, J=10.5 Hz, 1H), 3.15 (t, J=6.9 Hz, 2H), 3.08-2.72 (m, 6H), 2.13 2.04 (m, 2H), 1.75-1.66 (m, 2H), 1.59-1.52 (m, 2H), 1.25 (d, J=5.1 Hz, 3H).

Preparation of Benzyl 4-{6-[3-(bis{(2S,3R)-2,3-dihydroxy-3-[(4R,5R)-5-hydroxy-2-methyl-1,3-dioxan-4-yl]propyl}amino)propoxy]naphthalene-2-yl}carbamate (102)

A solution of carbamate 101 (368 mg, 0.62 mmol), triol 100 (675 mg, 3.10 mmol), sodium cyanoborohydride (338 mg, 4.96 mmol), and HOAc (290 mg, 4.96 mmol) in MeOH (15 mL) was stirred at room temperature for 7 d. The reaction mixture was concentrated to dryness; the residue was washed with saturated $NaHCO_3$, and extracted with EtOAc (3×200 mL). The organic layers was dried over $MgSO_4$, filtered, concentrated, and purified by column chromatography (silica gel, 80:18:2 $CH_2Cl_2/CH_3OH/NH_4OH$) to afford carbamate 102 (318 mg, 65%) as an white gummy solid: $^1$H NMR (300 MHz, $CD_3OD$) δ 7.67 (d, J=8.4 Hz, 2H), 7.54 (s, 1H), 7.31-7.27 (m, 6H), 7.21 (s, 1H), 7.11 (dd, J=9.0 Hz, 2.4 Hz, 1H), 5.06 (s, 2H), 4.48 (q, J=5.0 Hz, 2H), 4.17 (t, J=5.7 Hz, 2H), 3.98 (dd, J=10.5 Hz, 5.4 Hz, 2H), 3.92-3.87 (m, 2H), 3.79-3.72 (m, 4H), 3.35 (d, J=2.1 Hz, 2H), 3.23 (t, J=10.5 Hz, 2H), 3.15 (t, J=6.9 Hz, 2H), 2.82-2.84 (m, 2H), 2.77-2.72 (m, 4H), 2.67-2.60 (m, 2H), 2.03-1.99 (m, 2H), 1.76-1.66 (m, 2H), 1.59-1.52 (m, 2H), 1.20 (d, J=5.1 Hz, 6H).

Preparation of (R,R,1R,1'R,2S,2'S)-3,3'-{3-[6-(4-Aminobutyl)naphthalene-2-yloxy]propylazanediyl}bis{1-[(4R,5R)-5-hydroxy-2-methyl-1,3-dioxan-4-yl]propane-1,2-diol} (103)

A suspension of carbamate 102 (318 mg) and 10% Pd/C (300 mg) in MeOH (15 mL) was subjected to hydrogenation conditions (1 atm) for 2 h at room temperature. The reaction mixture was filtered through a plug of diatomaceous earth and the plug was washed with MeOH. The filtrate was concentrated in vacuo and the residue was purified by column chromatography (silica gel, 80:18:2 $CHCl_3/CH_3OH/NH_4OH$) to afford amine 103 (212 mg, 80%) as a white solid: $^1H$ NMR (300 MHz, $CD_3OD$) δ 7.68 (d, J=7.2 Hz, 2H), 7.56 (s, 1H), 7.30 (d, J=8.1 Hz, 1H), 7.21 (s, 1H), 7.11 (d, J=8.7 Hz, 1H), 4.50-4.49 (m, 2H), 4.17-4.15 (m, 2H), 4.02-3.96 (m, 2H), 3.88 (br s, 2H), 3.79-3.78 (m, 4H), 3.36-3.35 (m, 2H), 7.22 (d, J=10.5 Hz, 2H), 2.80-2.58 (m, 10H), 2.10-1.90 (m, 2H), 1.75-1.73 (m, 2H), 1.65-1.45 (m, 2H), 1.22-1.20 (m, 6H).

Preparation of Carboxamide 104

To a solution of amine 103 (212 mg, 0.33 mmol) and methyl 3,5-diamino-6-chloropyrazine-2-carbonylcarbamimidothioate (10, 202 mg, 0.52 mmol) in EtOH (15 mL) was added DIPEA (0.40 mL, 2.28 mmol) at room temperature. The reaction mixture was heated at 70° C. in a sealed tube for 2 h, then cooled to room temperature, and concentrated in vacuo. The residue was purified by column chromatography (silica gel, 80:18:2 $CHCl_3/CH_3OH/NH_4OH$) to afford carboxamide 104 (120 mg, 43%) as a yellow solid: $^1H$ NMR (300 MHz, $CD_3OD$) δ 7.69-7.65 (m, 2H), 7.57 (s, 1H), 7.30 (d, J=8.1 Hz, 1H), 7.19 (s, 1H), 7.10 (dd, J=9.0 Hz, 2.4 Hz, 1H), 4.50 (q, J=4.8 Hz, 2H), 4.16-4.15 (m, 2H), 4.02-3.96 (m, 2H), 3.90 3.86 (m, 2H), 3.80-3.72 (m, 4H), 3.36-3.20 (m, 6H), 2.83-2.58 (m, 8H), 2.02-1.98 (m, 2H), 1.82-1.79 (m, 2H), 1.71-1.69 (m, 2H), 1.21-1.16 (m, 6H).

Preparation of Carboxamide Lactate Salt 105

To a solution of carboxamide 104 (120 mg, 0.14 mmol) in EtOH (5 mL) was added lactic acid (27 mg, 0.30 mmol) at room temperature and the reaction mixture was stirred for 15 min. The solution was concentrated and the residue was azeotroped with MeOH. The residue was dissolved in $H_2O$/MeOH (8:2, 10 mL) and lyophilized to afford lactate salt 105 (147 mg, >99%) as a yellow solid: $^1H$ NMR (300 MHz, DMSO-$d_6$) δ 7.74 (d, J=8.1 Hz, 2H), 7.63 (s, 1H), 7.34 (d, J=8.4 Hz, 1H), 7.27 (s, 1H), 7.19 (s, 1H), 7.12 (dd, J=9.0 Hz, 2.1 Hz, 1H), 5.14-5.06 (m, 1H), 4.90 (q, J=7.0 Hz, 1H), 4.60 (q, J=5.0 Hz, 2H), 4.23-4.13 (m, 3H), 4.03-3.91 (m, 4H), 3.78-3.77 (m, 2H), 3.70-3.62 (m, 5H), 3.38-3.19 (m, 13H), 2.78-2.58 (m, 8H), 1.97-1.93 (m, 2H), 1.73-1.71 (m, 2H), 1.56-1.62 (m, 2H), 1.47 (d, J=6.9 Hz, 1H), 1.40 (d, J=7.0 Hz, 2H), 1.30 (d, J=6.9 Hz, 2H), 1.23 (d, J=6.9 Hz, 6H), 1.17 (d, J=5.1 Hz, 6H); ESI-MS m/z 887 $[C_{39}H_{57}ClN_8O_{12}+Na]^+$.

Alternate Synthesis of N-(3,5-Diamino-6-chloro-pyrazine-2-carbonyl)-N'-{4-[4-(3-guanidino-propoxy)-naphthalen-1-yl]-butyl}-guanidine 75

1. {3-[4-(4-Azido-but-1-enyl)-naphthalen-1-yloxy]-propyl}-carbamic acid tert-butyl Ester

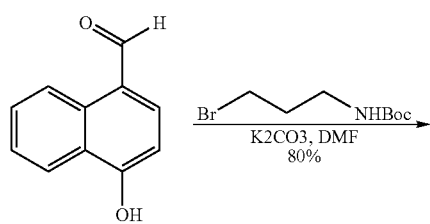

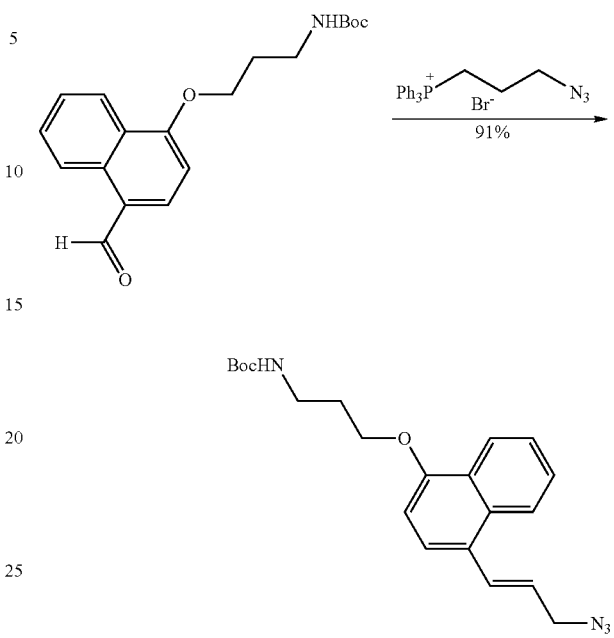

a.
[3-(4-formyl-naphthalen-1-yloxy)-propyl]-carbamic Acid Tert-Butyl Ester

To a solution of 4-hydroxy-naphthalene-1-carbaldehyde (15.2 g, 58.1 mmol) in DMF (50 mL) at r.t. was added N-Boc 3-bromo-propylamine (15.2 g, 63.9 mmol), followed by potassium carbonate (12 g, 87.2 mmol). The reaction mixture was stirred at room temperature overnight. Water was added to the reaction mixture and extracted by CH2Cl2. The combined organic layers were washed with water, brine, dried over $MgSO_4$, filtered, and concentrated. The residue was recrystallized from EtOAc/hexane to afford [3-(4-formyl-naphthalen-1-yloxy)-propyl]-carbamic acid tert-butyl ester (13.8 g, 72%) as a light yellow solid.

b. {3-[4-(4-Azido-but-1-enyl)-naphthalen-1-yloxy]-propyl}-carbamic Acid Tert-Butyl Ester To a mixture of Wittig reagent (3-azido-propyl)-triphenyl-phosphonium bromide (15.35 g, 36 mmol) in THF (150 mL) at −76° C., was added LIHMDS (0.5M in THF solution, 66 mL, 66 mmol). The mixture was stirred at this temperature for 1 h. [3-(4-formyl-naphthalen-1-yloxy)-propyl]-carbamic acid tert-butyl ester (10 g, 30 mmol) in 20 mL of THF solution was added. The reaction mixture was stirred for 1 hour. Then warm up to r.t. in 1 h. Water was added to quench the reaction, and extracted with EtOAc. The organic layer was washed with water, brine, dried over $MgSO_4$, filtered, and concentrated. The residue was purified by column chromatography to afford {3-[4-(4-azido-but-1-enyl)-naphthalen-1-yloxy]-propyl}-carbamic acid tert-butyl ester, 1 g, 88% as a solid c. Wittig Reagent
(3-azido-propyl)-triphenyl-phosphonium Bromide

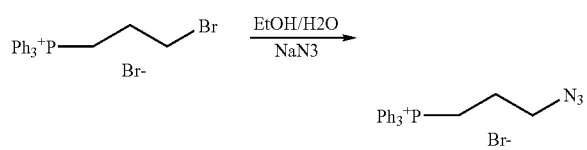

(3-Bromo-propyl)-triphenyl-phosphonium bromide was dissolved in ethanol/water (1/1). To it sodium azide was added. The reaction mixture was heated up to reflux overnight. Solvents were removed by evaporation. The residue was extracted by dry ethanol. Filtered and evaporated to give crude (3-azido-propyl)-triphenyl-phosphonium bromide and was used directly for the next step reaction without further purification.

2. N-{4-[4-(3-Amino-propoxy)-naphthalen-1-yl]-butyl}-N'-(3,5-diamino-6-chloro-pyrazine-2-carbonyl)-guanidine {3-[4-(4-Azido-but-1-enyl)-naphthalen-1-yloxy]-propyl}-carbamic acid tert-butyl ester 3.5 g was hydrogenated in ethanol with 5% Pd/C (50% wet) for 2 h. Catalyst was removed, and the filtrate was concentrated to give 2.94 g of {3-[4-(4-Amino-butyl)-naphthalen-1-yloxy]-propyl}-carbamic acid tert-butyl ester. One gram (2.66 mmol) of free amine was stirred with 1-(3,5-diamino-6-chloro-pyrazine-2-carbonyl)-2-methyl-isothiourea (1.55 g, 3.99 mmol) in dry ethanol (25 mL). Diisopropyl-ethylamine (1.39 mL, 7.98 mmol) of was added and the reaction mixture was warmed to 45° C. overnight. Ethanol was added and the reaction filtered. After concentration of the filtrate, the residue was purified by flash chromatography (0-10% MeOH/CH$_2$Cl$_2$) to give 0.92 g of [3-(4-{4-[N'-(3,5-Diamino-6-chloro-pyrazine-2-carbonyl)-guanidino]-butyl}-naphthalen-1-yloxy)-propyl]-carbamic acid tert-butyl ester. [3-(4-{4-[N'-(3,5-Diamino-6-chloro-pyrazine-2-carbonyl)-guanidino]-butyl}1-naphthalen-1-yloxy)-propyl]-carbamic acid tert-butyl ester (2.7 g was stirred with 4M HCl in p-dioxane for 1 hour at room temperature. Solvents were removed in vacuo. A small amount of the product was purified by flash chromatography to give 7 GS-426675 N-{4-[4-(3-Amino-propoxy)-naphthalen-1-yl]-butyl}-N'-(3,5-diamino-6-chloro-pyrazine-2-carbonyl)-guanidine as an HCl salt.

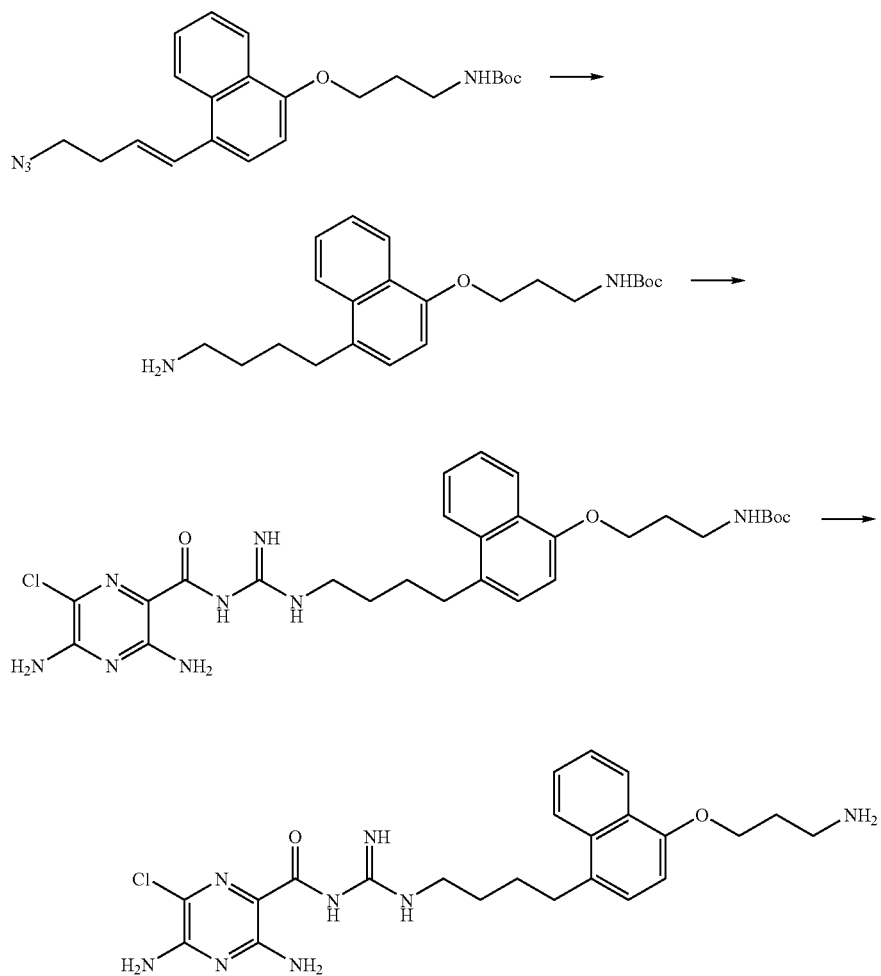

3. N-(3,5-Diamino-6-chloro-pyrazine-2-carbonyl)-N'-{4-[4-(3-guanidino-propoxy)-naphthalen-1-yl]-butyl}-guanidine 75

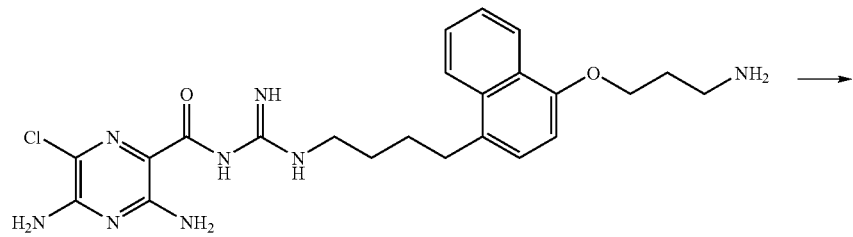

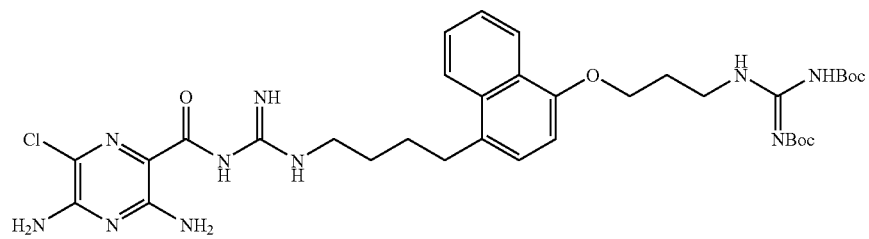

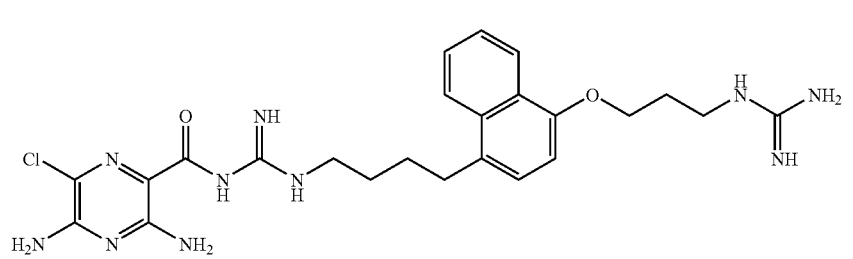

75

N-{4-[4-(3-Amino-propoxy)-naphthalen-1-yl]-butyl}-N'-(3,5-diamino-6-chloro-pyrazine-2-carbonyl)-guanidine HCl salt from reaction was stirred with Goodman's reagent [(tert-butoxycarbonylamino-tri fluoromethane sulfonylimino-methyl)-carbamic acid tert-butyl ester] in methanol. Diisopropylethylamine (1.18 mL) was added and the reaction mixture was stirred at room temperature overnight. Solvents were removed in vacuo and the residue was purified by silica gel chromatography (0-10% MeOH(MeOH/NH$_4$OH=9/1)/CH$_2$Cl$_2$) to give 2.7 g of 8, which was dissolve in 30 mL of methanol and treated with 300 mL of 4M HCl in p-dioxane at room temperature for 4 hour to give 9, N-(3,5-Diamino-6-chloro-pyrazine-2-carbonyl)-N'-{4-[4-(3-guanidino-propoxy)-naphthalen-1-yl]-butyl}-guanidine as a crude product. About 200 mL of the solvents were removed by reduced pressure, then cool to room temperature, and let the product precipitated out. Filtration to collect the product, and the product was further refluxed with dry EtOH, and cool down to room temperature. Filtration to give 2.08 g of 75 as an HCl salt (yellow solid).

Scheme 17
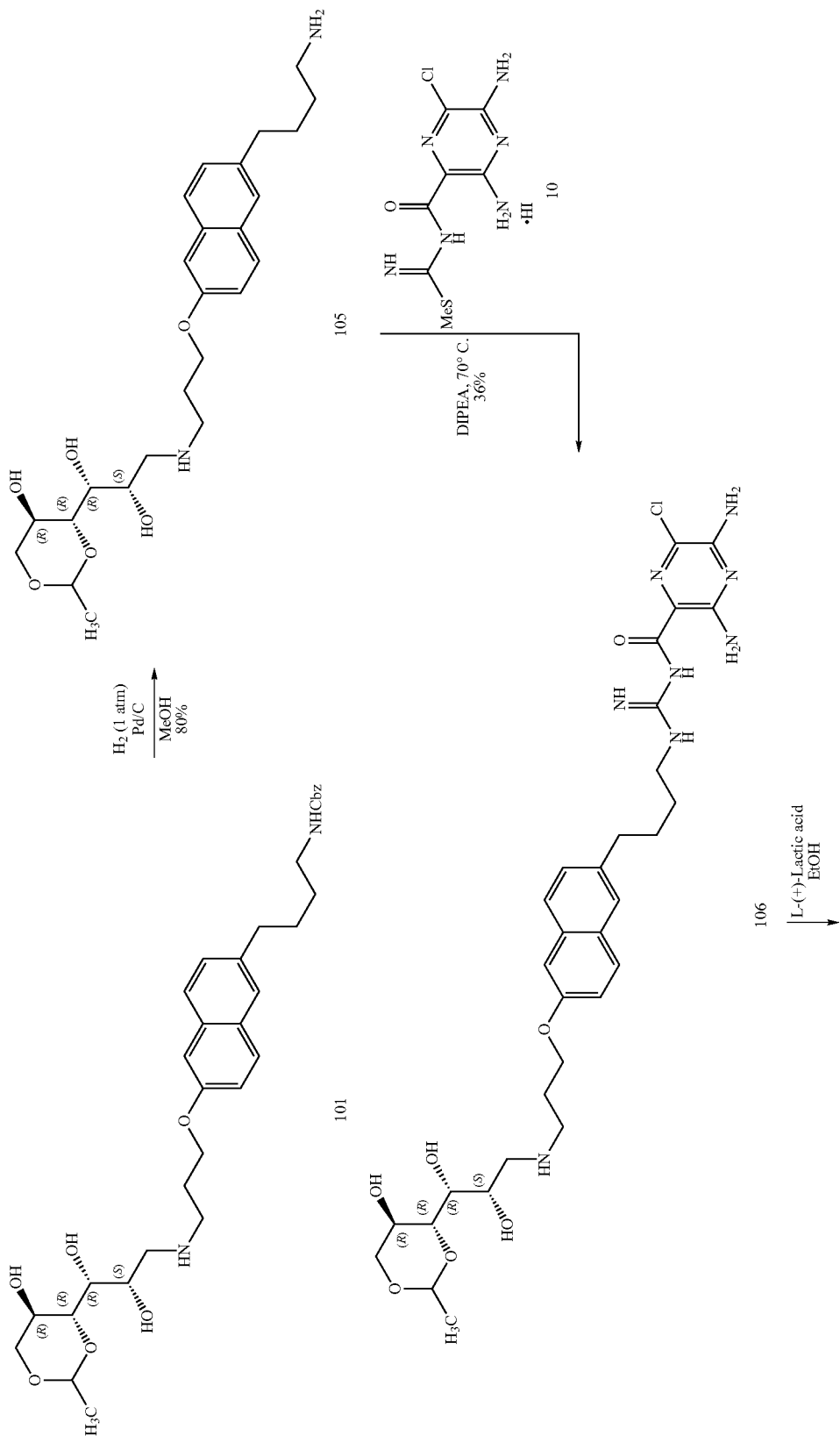

-continued
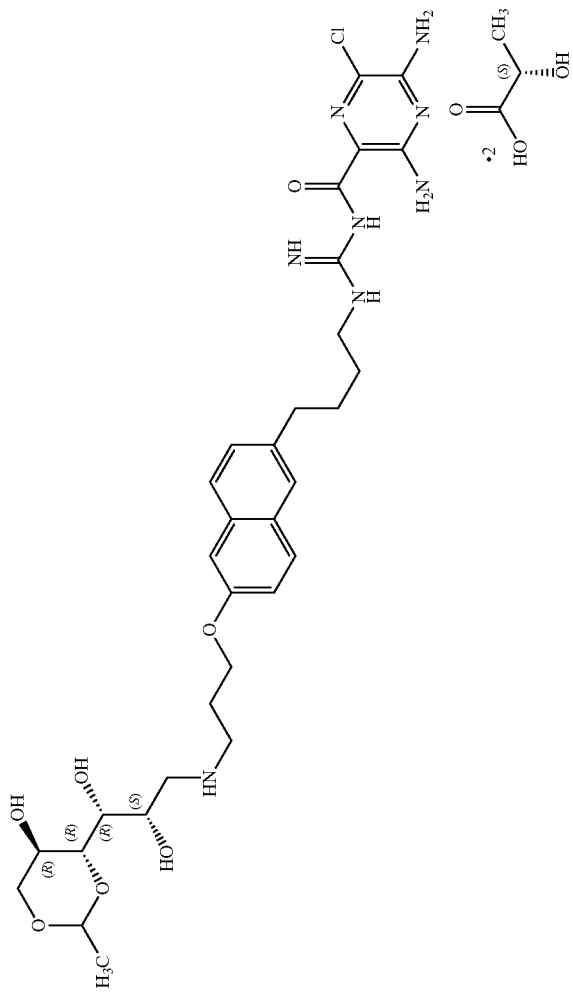

Preparation of (1R,2S)-3-{3-[6-(4-Aminobutyl)naph-thalene-2-yloxy]propylamino}-[1-[(4R,5R)-5-hydroxy-2-methyl-1,3-dioxan-4-yl]propane-1,2-diol} (105)

A suspension of 101 (76 mg) and 10% Pd/C (76 mg) in MeOH (5 mL) was subjected to hydrogenation conditions (1 atm) for 2 h at room temperature. The reaction mixture was filtered through a plug of diatomaceous earth and the plug was washed with MeOH. The filtrate was concentrated in vacuo and the residue was purified by column chromatography (silica gel, 80:18:2 CHCl$_3$/CH$_3$OH/NH$_4$OH) to afford amine 105 (46 mg, 80%) as a white solid: $^1$H NMR (300 MHz, CD$_3$OD) □ 7.65 (d, J=8.7 Hz, 2H), 7.53 (s, 1H), 7.28 (d, J=8.4 Hz, 1H), 7.18 (s, 1H), 7.10 (dd, J=8.7 Hz, 1.8 Hz, 1H), 4.66 (q, J=4.8 Hz, 1H), 4.14 (t, J=6.0 Hz, 2H), 4.06 (q, J=5.3 Hz, 1H), 3.98 3.92 (m, 1H), 3.83-3.74 (m, 2H), 3.45 (dd, J=9.0 Hz, 1.5 Hz, 1H), 3.37 (d, J=10.5 Hz, 1H), 2.93-2.66 (m, 8H), 2.08-2.00 (m, 2H), 1.77-1.67 (m, 2H), 1.58-1.49 (m, 2H), 1.25 (d, J=4.8 Hz, 3H).

Preparation of Guanidine 106

To a solution of amine 105 (46 mg, 0.10 mmol) and methyl 3,5-diamino-6-chloropyrazine-2-carbonylcarbamimidothioate (10, 70 mg, 0.16 mmol) in EtOH (6 mL) was added DIPEA (0.13 mL, 0.7 mmol) at room temperature. The reaction mixture was heated at 70° C. in a sealed tube for 2 h, then cooled to room temperature, and concentrated in vacuo. The residue was purified by column chromatography (silica gel, 80:18:2 CHCl$_3$/CH$_3$OH/NH$_4$OH) to afford guanidine 106 (16 mg, 24%) as a yellow solid: $^1$H NMR (300 MHz, CD$_3$OD) □ 7.66 (d, J=7.5 Hz, 2H), 7.55 (s, 1H), 7.30 (d, J=8.1 Hz, 1H), 7.17 (s, 1H), 7.10 (d, J=8.7 Hz, 1H), 4.67-4.66 (m, 1H), 4.16 (s, 2H), 4.08-3.97 (m, 2H), 3.82-3.77 (m, 2H), 3.64-3.58 (m, 2H), 3.46 (d, J=9.0 Hz, 1H), 3.40 (d, J=3.3 Hz, 1H), 2.05-2.09 (m, 2H), 1.82-1.70 (m, 4H), 1.25 (d, J=4.8 Hz, 3H).

Preparation of Guanidine Lactate Salt 107

To a solution of guanidine 106 (16 mg, 0.024 mmol) in EtOH (5 mL) was added lactic acid (4.5 mg, 0.048 mmol) at room temperature and the reaction mixture was stirred for 15 min. The solution was concentrated and the residue was azeotroped with MeOH. The residue was dissolved in H$_2$O/MeOH (8:2, 10 mL) and lyophilized to afford lactate salt 107 (20 mg, >95%) as a yellow solid: $^1$H NMR (300 MHz, CD$_3$OD) □ 7.78 (t, J=7.8 Hz, 2H), 7.62 (s, 1H), 7.35 (d, J=8.4 Hz, 1H), 7.27 (s, 1H), 7.13 (dd, J=8.8 Hz, 2.3 Hz, 1H), 7.00 (br s, 1H), 5.10-5.05 (m, 1H), 4.85 (q, J=7.0 Hz, 1H), 4.63 (q, J=5.0 Hz, 1H), 4.21 4.12 (m, 3H), 3.99-3.87 (m, 4H), 3.73 (d, J=5.1 Hz, 1H), 3.68 3.59 (m, 2H), 3.44-3.23 (m, 4H), 3.06-3.00 (m, 4H), 2.90-2.83 (m, 1H), 2.75 (t, J=6.7 Hz, 2H), 2.11-2.07 (m, 2H), 1.71-1.57 (m, 4H), 1.46 (d, J=6.9 Hz, 1H), 1.37 (d, J=7.2 Hz, 3H), 1.28 (d, J=6.6 Hz, 3H), 1.24-1.13 (m, 10H), 0.86-0.82 (m, 1H); ESI-MS m/z 675 [C$_{31}$H$_{43}$ClN$_8$O$_7$+H]$^+$.

Preparation of N-{4-[4-(3-Amino-propoxy)-5,6,7,8-tetrahydro-naphthalen-1-yl]-butyl}-N'-(3,5-diamino-6-chloro-pyrazine-2-carbonyl)-guanidine (116) and N-(3,5-Diamino-6-chloro-pyrazine-2-carbonyl)-N'-{4-[4-(3-guanidino-propoxy)-5,6,7,8-tetrahydro-naphthalen-1-yl]-butyl}-guanidine (118)

1. 4-hydroxy-5,6,7,8-tetrahydro-naphthalene-1-carbaldehyde (109)

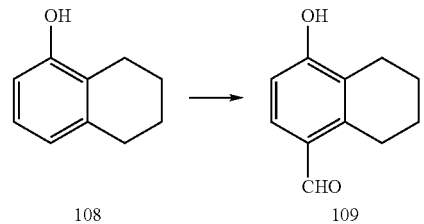

5,6,7,8-Tetrahydro-naphthalen-1-ol (108, 20 g, 135 mmol) was stirred in 100 mL of ethanol, and potassium hydroxide (7.57 g, 135 mmol) as an aqueous solution was added. The mixture was stirred for 15 minutes and went clear. Solvents were removed and dried. PEG (MW 380-420, 53 mL) was added, followed by chloroform (32.3 mL, 405 mmol) and toluene (34 mL). An aqueous potassium hydroxide solution (50% by weight, 54.4 mL) was introduced dropwise with stirring over 15 minutes. The stirring was continued for another 30 minutes. 1M HCl was added to acidify the reaction mixture and it was extracted with EtOAc three times. The combined organic layers were washed with water and brine The combined organic layers were dried over MgSO$_4$, filtered, concentrated, and purified by flash chromatography (0-40% EtOAc/hexane) to give 4-hydroxy-5,6,7,8-tetrahydro-naphthalene-1-carbaldehyde (109, 4.7 g).

2. [3-(4-Formyl-5,6,7,8-tetrahydro-naphthalen-1-yloxy)-propyl]-carbamic acid tert-butyl ester (111)

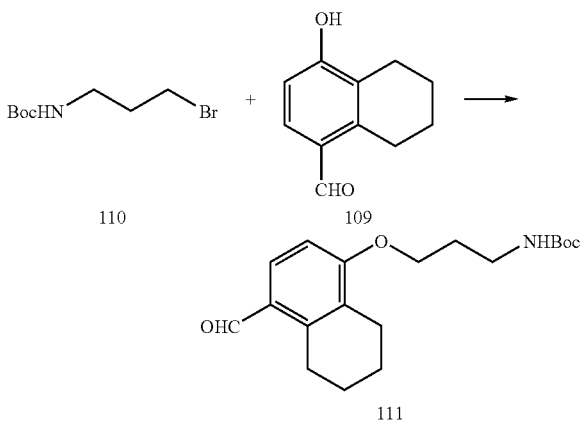

4-Hydroxy-5,6,7,8-tetrahydro-naphthalene-1-carbaldehyde (109, 4.6 g, 29.1 mmol) (3-Bromopropyl)-carbamic acid tert-butyl ester (110, 4.6 g, 32 mmol), and potassium carbonate (6.03 g, 43.7 mmol) were stirred in 140 mL of dry DMF over night. The reaction mixture was poured into water and extracted with dichloromethane. The organic layer was washed with water and brine., dried with magnesium sulfate, filtered, concentrated and purified by flash chromatography (0-30% EtOAc/hexane) to give crude product, which was recrystallized from EtOAc/Hexane to give 5.8 g of 111, [3-(4-formyl-5,6,7,8-tetrahydro-naphthalen-1-yloxy)-propyl]-carbamic acid tert-butyl ester.

3. {3-[4-(4-Azido-but-1-enyl)-5,6,7,8-tetrahydro-naphthalen-1-yloxy]-propyl}-carbamic acid tert-butyl ester (113)

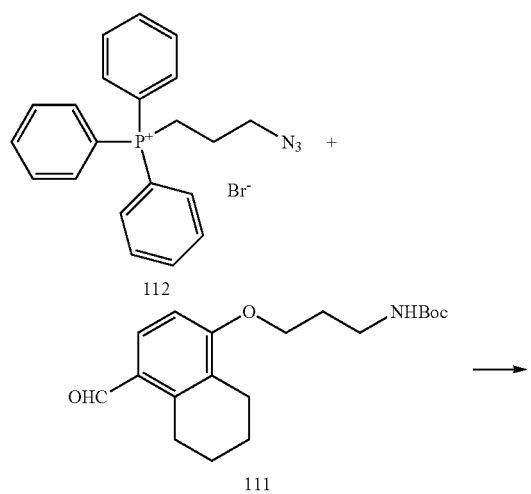

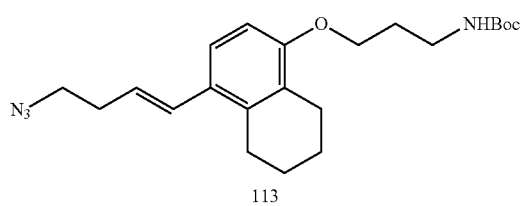

(3-Azido-propyl)-triphenylphosphonium bromide (112, 11.5 g, 27 mmol) was stirred with 100 mL of dry THF at −76° C. LiHMDS (0.5 M in toluene, 27 mL) was added and the mixture was stirred for 30 minutes. [3-(4-Formyl-5,6,7,8-tetrahydro-naphthalen-1-yloxy)-propyl]-carbamic acid tert-butyl ester (111, 6 g, 18 mmol) in 12 mL dry THF solution was introduced. The reaction mixture was stirred at this temperature for another 30 minutes, and slowly warmed to room temperature. The mixture was poured into water and extracted twice with ethyl acetate. The combined organic layers were washed with water and brine, dried over magnesium sulfate, filtered, concentrated, and purified by flash chromatography (0-25% EtOAc/Hexane) to give 3.5 g 113 {3-[4-(4-azido-but-1-enyl)-5,6,7,8-tetrahydro-naphthalen-1-yloxy]-propyl}-carbamic acid tert-butyl ester.

4. N-{4-[4-(3-Amino-propoxy)-5,6,7,8-tetrahydro-naphthalen-1-yl]-butyl}-N'-(3,5-diamino-6-chloro-pyrazine-2-carbonyl)-guanidine (116)

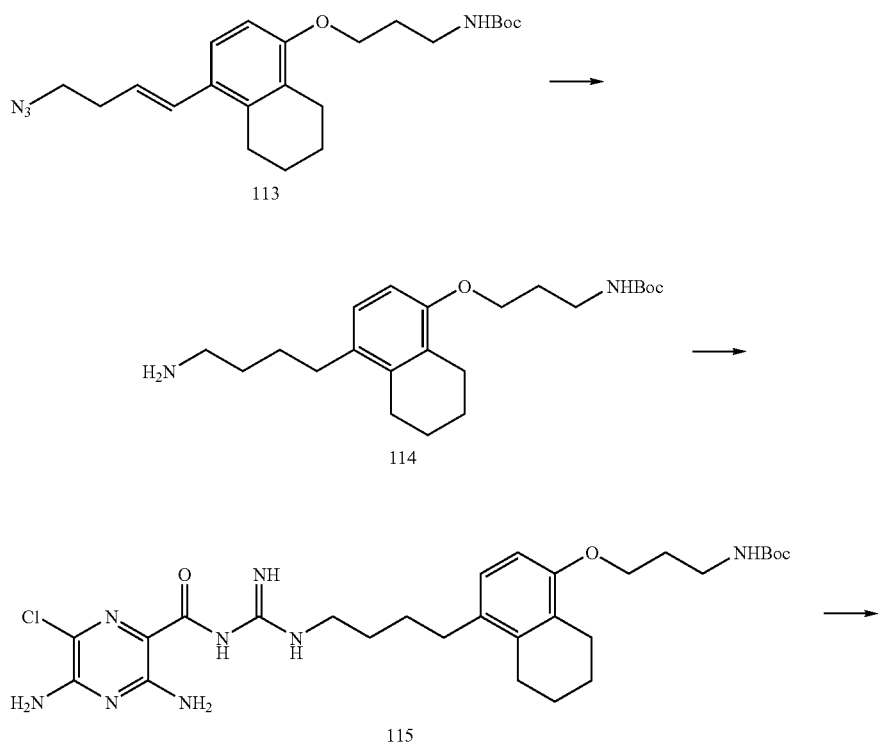

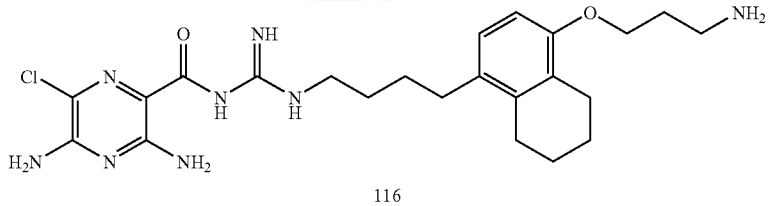

116

{3-[4-(4-Azido-but-1-enyl)-5,6,7,8-tetrahydro-naphthalen-1-yloxy]-propyl}-carbamic acid tert-butyl ester 113, 3.5 g was hydrogenated in ethanol with 5% Pd/C (50% wet) for 2 h. Catalyst was removed, and the filtrate was concentrated to give 2.94 g of 114, {3-[4-(4-amino-butyl)-5,6,7,8-tetrahydro-naphthalen-1-yloxy]-propyl}-carbamic acid tert-butyl ester.

One gram (2.66 mmol) of free amine 114 was stirred with 1-(3,5-diamino-6-chloro-pyrazine-2-carbonyl)-2-methyl-isothiourea (1.55 g, 3.99 mmol) in dry ethanol (25 mL). Di-isopropyl-ethylamine (1.39 mL, 7.98 mmol) of was added and the reaction mixture was warmed to 45° C. overnight. Ethanol was added and the reaction filtered. After concentration of the filtrate, the residue was purified by flash chromatography (0-10% MeOH/CH$_2$Cl$_2$) to give 0.92 g of 115 [3-(4-{4-[N'-(3,5-diamino-6-chloro-pyrazine-2-carbonyl)-guanidino]-butyl}-5,6,7,8-tetrahydro-naphthalen-1-yloxy)-propyl]-carbamic acid tert-butyl ester.

N-{4-[4-(3-Amino-propoxy)-5,6,7,8-tetrahydro-naphthalen-1-yl]-butyl}-N'-(3,5-diamino-6-chloro-pyrazine-2-carbonyl)-guanidine was stirred with 4M HCl in p-dioxane for 30 minutes at room temperature. Solvents were removed n vacuo, and the product was purified by amine column (0-40% MeOH/CH$_2$Cl$_2$) to give 116 N-{4-[4-(3-amino-propoxy)-5, 6,7,8-tetrahydro-naphthalen-1-yl]-butyl}-N'-(3,5-diamino-6-chloro-pyrazine-2-carbonyl)-guanidine as an HCl salt.

5. N-(3,5-Diamino-6-chloro-pyrazine-2-carbonyl)-N'-{4-[4-(3-guanidino-propoxy)-5,6,7,8-tetrahydro-naphthalen-1-yl]-butyl}-guanidine GS-429269 (11)

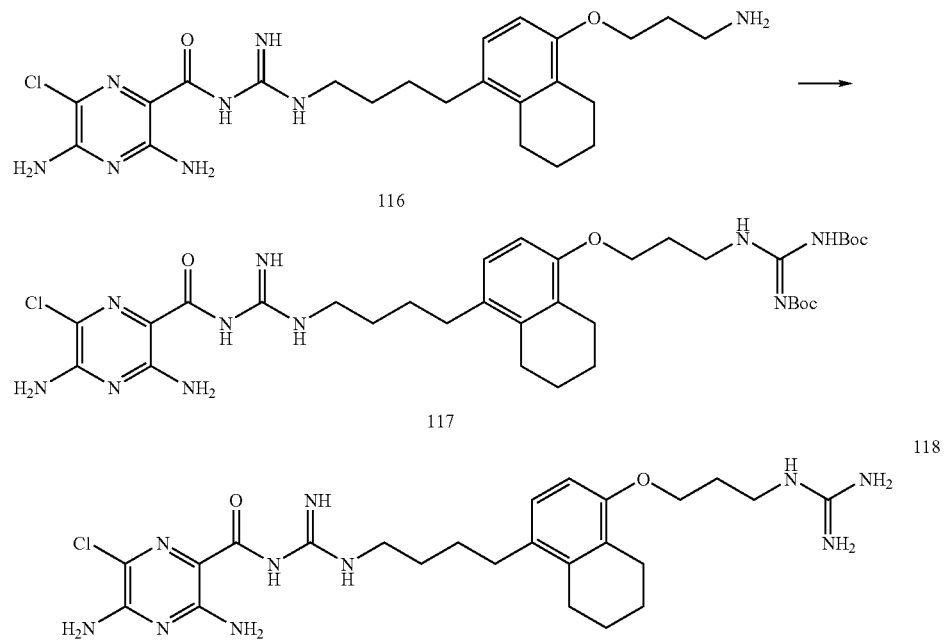

N-{4-[4-(3-Amino-propoxy)-5,6,7,8-tetrahydro-naphthalen-1-yl]-butyl}-N'-(3,5-diamino-6-chloro-pyrazine-2-carbonyl)-guanidine HCl salt 116 (0.81 g, 1.37 mmol) was stirred with Goodman's reagent [(tert-butoxycarbonylamino-trifluoromethane sulfonylimino-methyl)-carbamic acid tert-butyl ester] in methanol. Diisopropylethylamine (1.18 mL) was added and the reaction mixture was stirred at room temperature overnight. Solvents were removed in vacuo and the residue was purified by silica gel chromatography (0-10% MeOH/CH$_2$Cl$_2$) to give 820 mg of 117, which was treated with 4M HCl in p-dioxane at room temperature for 1 hour to give 118, N-(3,5-diamino-6-chloro-pyrazine-2-carbonyl)-N'-{4-[4-(3-guanidino-propoxy)-5,6,7,8-tetrahydro-naphthalen-1-yl]-butyl}-guanidine as a crude product. Purification by flash chromatography (0-40% (MeOH/NH4OH; 3/1)/CH$_2$Cl$_2$) followed by further purification on an amine column (0-30% MeOH/CH$_2$Cl$_2$) gave the free base, which was dissolved in ethanol and a few drops of 1 M HCl aq was added. The clear solution was filtered and lyophilized to give final product as a yellow solid.

All references cited herein are hereby incorporated in their entirety as if each reference was individually and specifically incorporated in its entirety.

What is claimed is:

1. A compound represented by the formula (I):

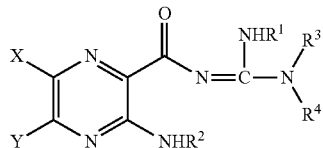
(I)

and racemates, enantiomers, diastereomers, tautomers, and pharmaceutically acceptable salts thereof, wherein:

X is hydrogen, halogen, or lower alkyl;

Y is hydrogen, or —N($R^2$)$_2$;

$R^1$ is hydrogen or lower alkyl;

each $R^2$ is, independently, —$R^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—(Z)$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

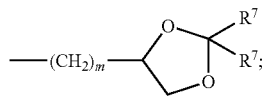

$R^3$ and $R^4$ are each, independently, hydrogen, lower alkyl, hydroxy-lower alkyl, phenyl, (phenyl)-lower alkyl, (halophenyl)-lower alkyl, ((lower-alkyl)phenyl)-lower-alkyl, ((lower-alkoxy)phenyl)-lower-alkyl, (naphthyl)-lower-alkyl, or (pyridyl)-lower-alkyl, or a group represented by formula A, with the proviso that at least one of $R^3$ and $R^4$ is a group represented by the formula A;

—(C($R^L$)$_2$)$_o$-x-(C($R^L$)$_2$)$_p$$A^1$ formula A $A^1$ is a $C_7$-$C_{15}$-membered aromatic carbocycle substituted with at least one $R^5$ and the remaining substituents are $R^6$;

each $R^1$ is, independently, —$R^7$, —(CH$_2$)$_n$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

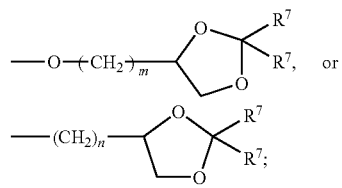

each o is, independently, an integer from 0 to 10;
each p is, independently, an integer from 0 to 10;
with the proviso that the sum of o and p in each contiguous chain is from 1 to 10;

each x is, independently, O, NR$^{10}$, C(=O), CHOH, C(=N—R$^{10}$), CHNR$^7$R$^{10}$, or a single bond;

each $R^5$ is, independently, Link-(CH$_2$)$_n$-CAP, Link-(CH$_2$)$_n$—(Z)$_g$-CAP, Link-(CH$_2$)$_n$(Z)$_g$—(CH$_2$)$_m$-CAP, —(CH$_2$)$_n$—NR$^{10}$—CH$_2$(CHOR$^8$)(CHOR$^8$)$_n$—CH$_2$OR$_8$, or —O—(CH$_2$)$_m$—NR$^{10}$—CH$_2$(CHOR$^8$)(CHOR$^8$)$_n$—CH$_2$OR$^8$;

each $R^6$ is, independently, $R^5$, —$R^7$, —OR$^{11}$, —N($R^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$C(=O)NR$^7$R$^{10}$, —O—(CH$_2$)$_m$—C(=O)NR$^7$R$^{10}$, —(CH$_2$)$_m$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

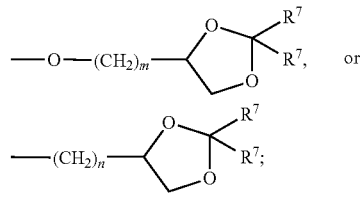

wherein when two $R^6$ are —OR$^{11}$ and are located adjacent to each other on the aromatic carbocycle or aromatic heterocycle, the two OR$^{11}$ may form a methylenedioxy group;

each $R^7$ is, independently, hydrogen, lower alkyl, phenyl, or substituted phenyl;

each $R^8$ is, independently, hydrogen, lower alkyl, —C(=O)—R$^{11}$, glucuronide, 2-tetrahydropyranyl, or

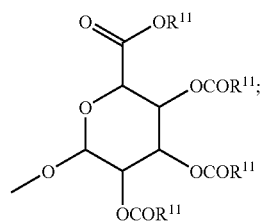

each $R^9$ is, independently, $-CO_2R^7$, $-CON(R^7)_2$, $-SO_2CH_3$, $-C(=O)R^7$, $-CO_2R^{13}$, $-CON(R^{13})_2$, $-SO_2CH_2R^{13}$, or $-C(=O)R^{13}$;

each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;

each Z is, independently, $-(CHOH)-$, $-C(=O)-$, $-(CHNR^7R^{10})-$, $-$, $-(C=NR^{10})-$, $-NR^{10}-$, $-(CH_2)_n-$, $-(CHNR^{13}R^{13})-$, $-(C=NR^{13})-$, or $-NR^{13}-$;

each $R^{11}$ is, independently, hydrogen, lower alkyl, phenyl lower alkyl or substituted phenyl lower alkyl;

each $R^{12}$ is, independently, $-SO_2CH_3$, $-CO_2R^7$, $-C(=O)NR^7R^9$, $-C(=O)R^7$, $-CH_2(CHOH)_n-CH_2OH$, $-CO_2R^{13}$, $-C(=O)NR^{13}R^{13}$, or $-C(=O)R^{13}$;

each $R^{13}$ is, independently, $R^7$, $R^{10}$, $-(CH_2)_m-NR^7R^{10}$, $-(CH_2)_m-NR^7R^7$, $-(CH_2)_m-NR^{11}R^{11}$, $-(CH_2)_m-(NR^{11}R^{11}R^{11})^+$, $-(CH_2)_m-(CHOR^8)_m-(CH_2)_mNR^{11}R^{11}$, $-(CH_2)_m-(CHOR^8)_m-(CH_2)_mNR^7R^{10}$, $-(CH_2)_m-NR^{10}R^{10}$, $-(CH_2)_m-(CHOR^8)_m(CH_2)_m(NR^{11}R^{11}R^{11})^+$, $-(CH_2)_m-(CHOR^8)_m-(CH_2)_mNR^7R^7$,

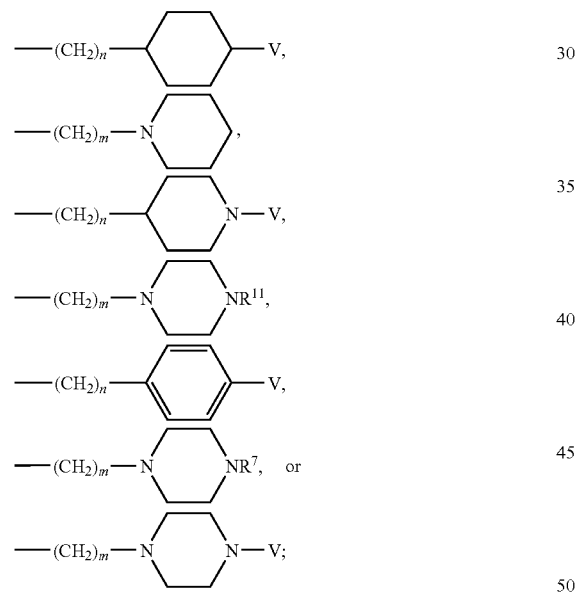

with the proviso that in the moiety $-NR^{13}R^{13}$, the two $R^{13}$ along with the nitrogen to which they are attached may, optionally, form a ring selected from:

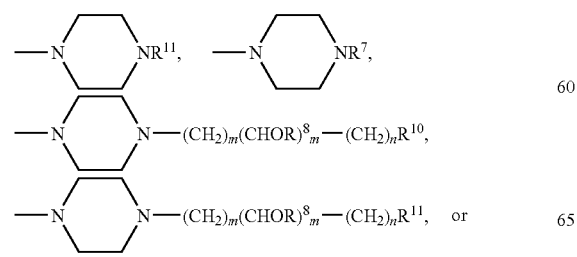

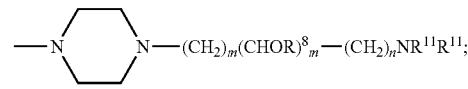

each V is, independently, $-(CH_2)_m-NR^7R^{10}$, $-(CH_2)_m-NR^7R^7$, $-(CH_2)_m-(NR^{11}R^{11}R^{11})^+$, $-(CH_2)_n-(CHOR^8)_m-(CH_2)_mNR^7R^{10}$, $-(CH_2)_n-NR^{10}R^{10}-(CH_2)_n-(CHOR^8)_m-(CH_2)_mNR^7R^7$, $-(CH_2)_n-(CHOR^8)_m-(CH_2)_m-(NR^{11}R^{11}R^{11})^+$ with the proviso that when V is attached directly to a nitrogen atom, then V can also be, independently, $R^7$, $R^{10}$, or $(R^{11})_2$;

each $R^{14}$ is, independently, H, $R^{12}$, $-(CH_2)_n-SO_2CH_3$, $-(CH_2)_n-CO_2R^{13}$, $-(CH_2)_n-C(=O)NR^{13}R^{13}$, $-(CH_2)_n-C(=O)R^{13}$, $-(CH_2)_n-(CHOH)_n-CH_2OH$, $-NH-(CH_2)_n-SO_2CH_3$, $NH-(CH_2)_n-C(=O)R^{11}$, $NH-C(=O)-NH-C(=O)R^{11}$, $-C(=O)NR^{13}R^{13}$, $-OR^{11}$, $-NH-(CH_2)_nR^{10}$, $-Br$, $-Cl$, $-F$, $-I$, $SO_2NHR^{11}$, $-NHR^{13}$, $-NH-C(=O)-NR^{13}R^{13}$, $-(CH_2)_n-NHR^{13}$, or $-NH(CH_2)_n-C(=O)R^{13}$;

each g is, independently, an integer from 1 to 6;

each m is, independently, an integer from 1 to 7;

each n is, independently, an integer from 0 to 7;

each Link is, independently, $-O-$, $-(CH_2)_n-$, $-O(CH_2)_m-$, $-NR^{13}-C(=O)-NR^{13}-$, $-NR^{13}-C(=O)-(CH_2)_m-$, $-C(=O)NR^{13}-(CH_2)_m-$, $-(CH_2)_n-(Z)_g-(CH_2)_n-$, $-S-$, $-SO-$, $-SO_2-$, $-SO_2NR^7-$, or $-SO_2NR^{10}$;

each CAP is, independently, thiazolidinedione, oxazolidinedione, -heteroaryl-$C(=O)N$ $R^{13}R^{13}$, heteroaryl-W, $-CN$, $-O-C(=S)NR^{13}R^{13}$, $-(Z)_gR^{13}$, $-CR^{10}((Z)_gR^{13})((Z)_gR^{13})$, $-C(=O)OAr$, $-C(=O)NR^{13}Ar$, imidazoline, tetrazole, tetrazole amide, $-SO_2NHR^{13}$, $-SO_2NH-C(R^{13}R^{13})-(Z)_g-R^{13}$, a cyclic sugar or oligosaccharide, a cyclic amino sugar, oligosaccharide, $-CR^{10}(-(CH_2)_m-R^9)(-(CH_2)_m-R^9)$, $-N(-(CH_2)_m-R^9)(-(CH_2)_m-R^9)$, $-NR^{13}(-(CH_2)_m-CO_2R^{13})$,

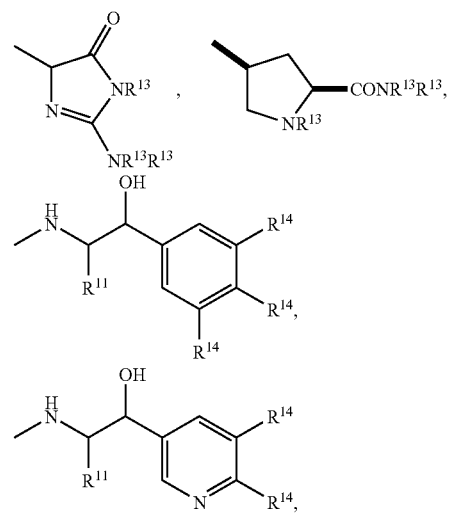

-continued

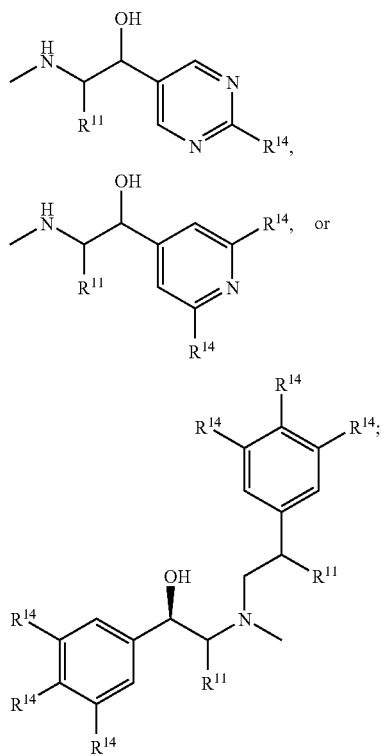

wherein CAP is not hydrogen or lower alkyl;

each Ar is, independently, phenyl, substituted phenyl, wherein the substituents of the substituted phenyl are 1-3 substituents independently selected from the group consisting of OH, OCH$_3$, NR$^{13}$R$^{13}$, Cl, F, and CH$_3$, or heteroaryl; and each W is, independently, thiazolidinedione, oxazolidinedione, heteroaryl-C(=O)N R$^{13}$R$^{13}$, —CN, —O—C(=S)NR$^{13}$R$^{13}$, —(Z)$_g$R$^{13}$, —CR$^{10}$((Z)$_g$R$^{13}$)((Z)$_g$R$^{13}$), —C(=O)OAr, —C(=O)NR$^{13}$Ar, imidazoline, tetrazole, tetrazole amide, —SO$_2$NHR$^{13}$, —SO$_2$NH—C(R$^{13}$R$^{13}$)—(Z)$_g$—R$^{13}$, a cyclic sugar or oligosaccharide, a cyclic amino sugar, oligosaccharide,

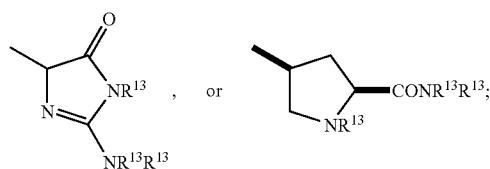

with the proviso that when any —CHOR$^8$— or —CH$_2$OR$^8$ groups are located 1,2- or 1,3-with respect to each other, the R$^8$ groups may, optionally, be taken together to form a cyclic mono- or di-substituted 1,3-dioxane or 1,3-dioxolane.

2. The compound according to claim 1, which is represented by the formula II:

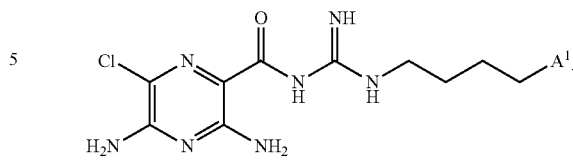

3. The compound of claim 1, wherein A$^1$ is selected from indenyl, napthalenyl, 1,2-dihydronapthalenyl, 1,2,3,4-tetrahydronapthalenyl, anthracenyl, fluorenyl, phenanthrenyl, azulenyl, cyclohepta-1,3,5-trienyl or 5H-dibenzo[a,d]cycloheptenyl, substituted with at least one R$^5$ and the remaining substituents are R$^6$.

4. The compound of claim 1, wherein R$^3$ is hydrogen and R$^4$ is a group represented by formula A.

5. The compound of claim 1, wherein R$^3$ is hydrogen, R$^4$ is a group represented by formula A, and A$^1$ is represented by the formula:

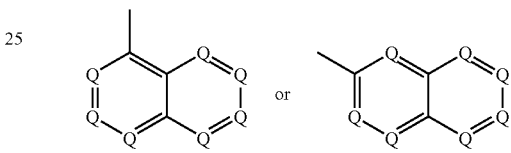

wherein each Q is, independently, C—H, C—R$^5$, or C—R$^6$, with the proviso that at least one Q is C—R$^5$.

6. The compound of claim 5, wherein one Q is C—R$^5$ and the remaining Q are C—H.

7. The compound of claim , wherein R$^3$ is hydrogen, R$^4$ is a group represented by formula A, and A$^1$ is represented by the formula:

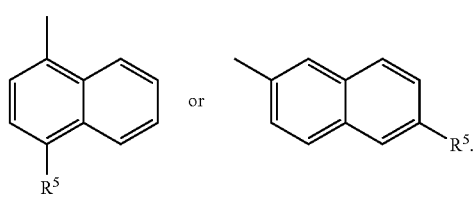

8. The compound of claim 1, wherein is Link-(CH$_2$)$_n$-CAP.
9. The compound of claim 1, wherein R$^5$ is Link-(CH$_2$)$_n$—(Z)$_g$-CAP.
10. The compound of claim 1, wherein R$^5$ is Link-(CH$_2$)$_n$(Z)$_g$—(CH$_2$)$_m$-CAP.
11. The compound of claim 1, wherein R$^5$ is —(CH$_2$)$_n$—NR$^{10}$—CH$_2$(CHOR$^8$)(CHOR$^8$)$_n$—CH$_2$OR$_8$.
12. The compound of claim 1, wherein R$^5$ is —O—(CH$_2$)$_m$—NR$^{10}$—CH$_2$(CHOR$^8$)(CHOR$^8$)$_n$—CH$_2$OR$^8$.
13. The compound of claim 1, wherein CAP is —(Z)$_g$R$^{13}$.
14. The compound of claim 1, wherein CAP is —CR$^{10}$((Z)$_g$R$^{13}$)((Z)$_g$R$^{13}$).
15. The compound of claim 1, which is an acid addition salt of an inorganic acid or an organic acid selected from the group consisting of hydrochloric acid, hydrobromic acid, sulfuric acid, phosphoric acid, nitric acid, acetic acid, oxalic acid, tartaric acid, succinic acid, maleic acid, furmaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, salicylic acid, stearic acid, phthalic acid, mandelic acid, and lactic acid.

16. The compound of claim 1, wherein
X, Y, $R^1$, $R^2$ and $R^3$ are each hydrogen;
$R^4$ is represented by formula A;
$A^1$ is a naphthalenyl or 1,2,3,4-tetrahydronaphthalenyl group, which is substituted by one $R^5$ group and the remaining substituents are hydrogen;
each $R^L$ group is hydrogen;
x is a single bond; and
the sum of o and p is from 2 to 6.

17. The compound of claim 16, wherein $A^1$ is a naphthalenyl group which is substituted by one $R^5$ group and the remaining substituents are hydrogen.

18. The compound of claim 17, wherein $R^5$ is Link-$(CH_2)_n$-CAP.

19. The compound of claim 17, wherein $R^5$ is Link-$(CH_2)_n$—$(Z)_g$-CAP.

20. The compound of claim 17, wherein $R^5$ is Link-$(CH_2)_n(Z)_g$—$(CH_2)_m$-CAP.

21. The compound of claim 17, wherein $R^5$ is —$(CH_2)_n$—$NR^{10}$—$CH_2(CHOR^8)(CHOR^8)_n$—$CH_2OR_8$.

22. The compound of claim 17, wherein $R^5$ is —O—$(CH_2)_m$—$NR^{10}$—$CH_2(CHOR^8)(CHOR^8)_n$—$CH_2OR^8$.

23. The compound of claim 17, wherein CAP is —$(Z)_gR^{13}$.

24. The compound of claim 17, wherein CAP is —$CR^{10}((Z)_gR^{13})((Z)_gR^{13})$.

25. The compound of claim 1, wherein
X, Y, $R^1$, $R^2$ and $R^3$ are each hydrogen;
each $R^L$ group is hydrogen;
x is a single bond; and
the sum of o and p is from 2 to 6.

26. The compound of claim 25, wherein $R^5$ is Link-$(CH_2)_n$-CAP.

27. The compound of claim 25, wherein $R^5$ is Link-$(CH_2)_n$—$(Z)_g$-CAP.

28. The compound of claim 25, wherein $R^5$ is Link-$(CH_2)_n(Z)_g$—$(CH_2)_m$-CAP.

29. The compound of claim 25, wherein $R^5$ is —$(CH_2)_n$—$NR^{10}$—$CH_2(CHOR^8)(CHOR^8)_n$—$CH_2OR_8$.

30. The compound of claim 25, wherein $R^5$ is —O—$(CH_2)_m$—$NR^{10}$—$CH_2(CHOR^8)(CHOR^8)_n$—$CH_2OR^8$.

31. The compound of claim 25, wherein CAP is —$(Z)_gR^{13}$.

32. The compound of claim 25, wherein CAP is —$CR^{10}((Z)_gR^{13})((Z)_gR^{13})$.

33. A pharmaceutical composition, comprising the compound of claim 1 or a pharmaceutically acceptable salt thereof and a pharmaceutically acceptable carrier.

34. The compound of claim 1, which is represented by the formula:

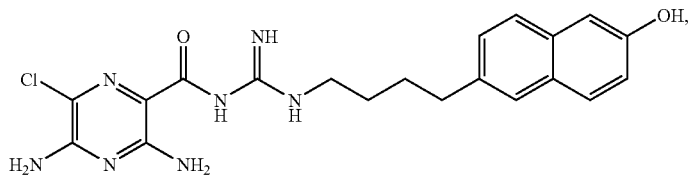

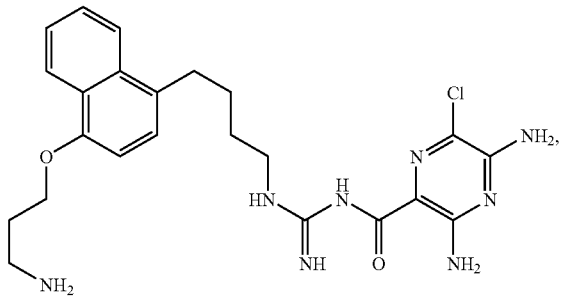

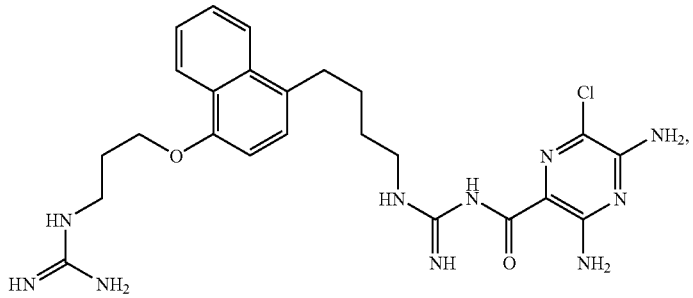

-continued
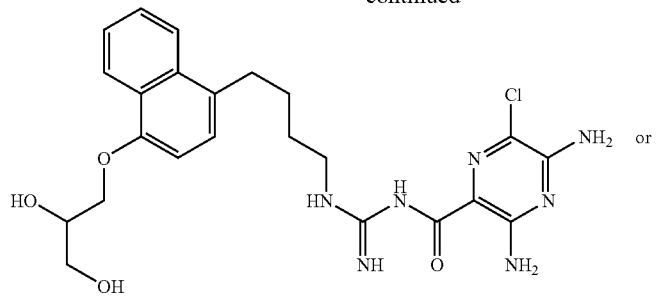
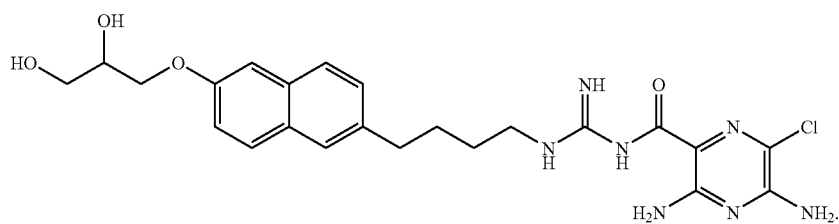
35. The compound of claim 1, which is represented by the formula:
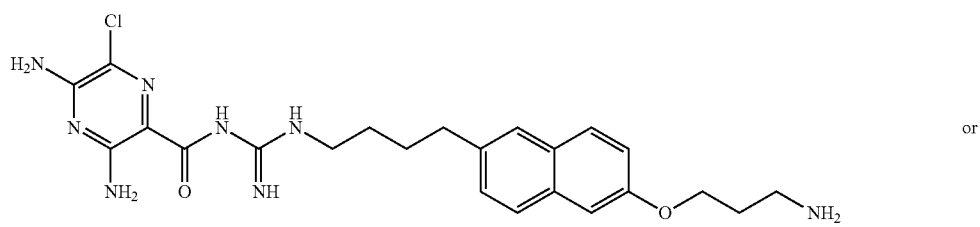
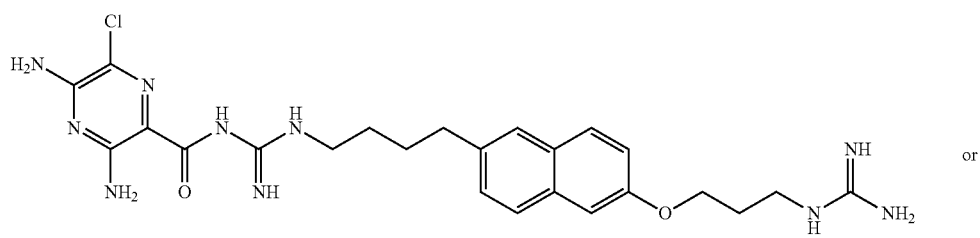
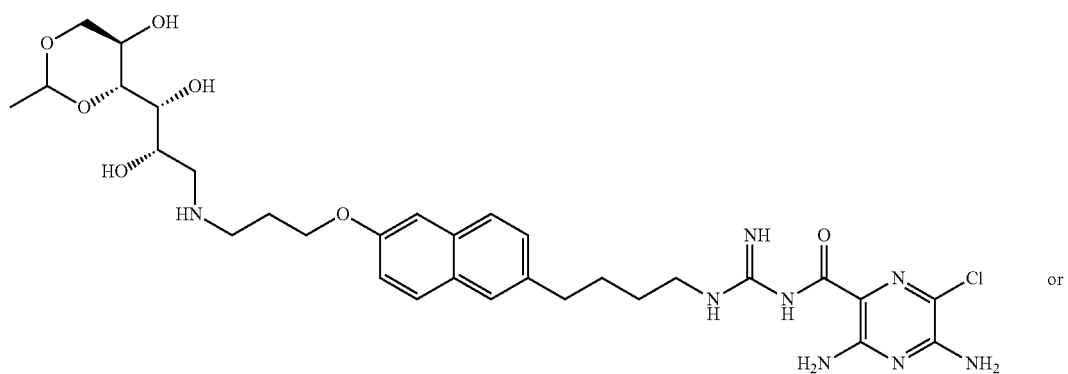

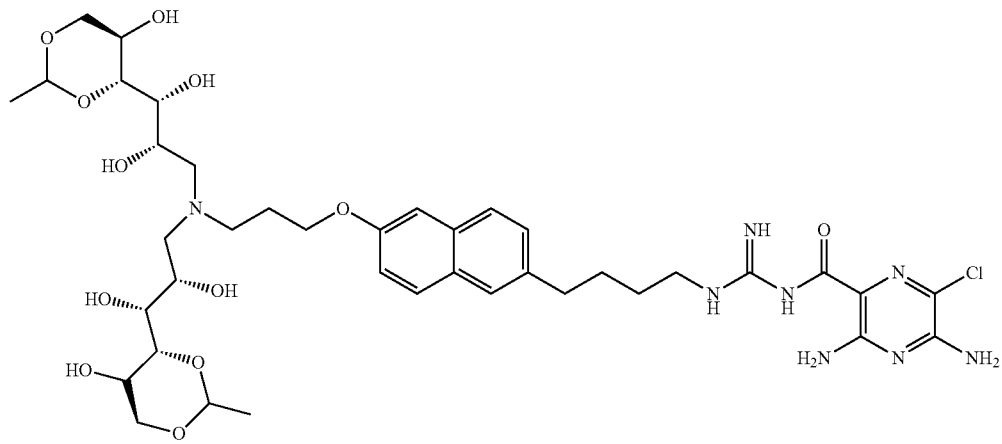
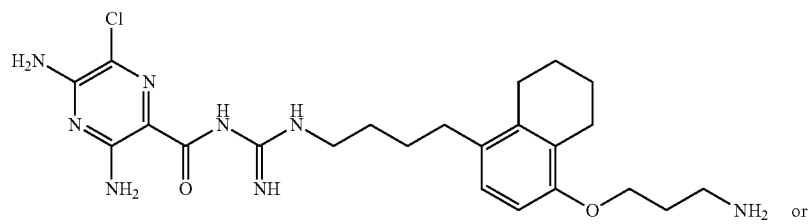
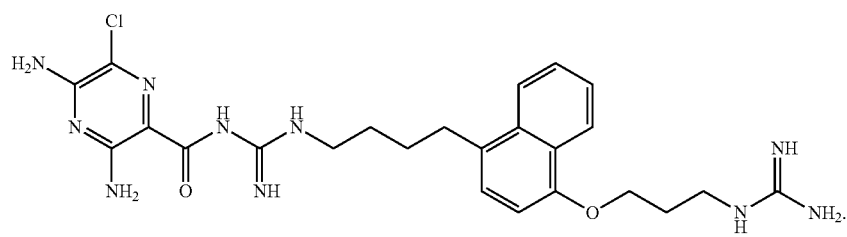
36. The compound of claim 1, which is represented by the formula:
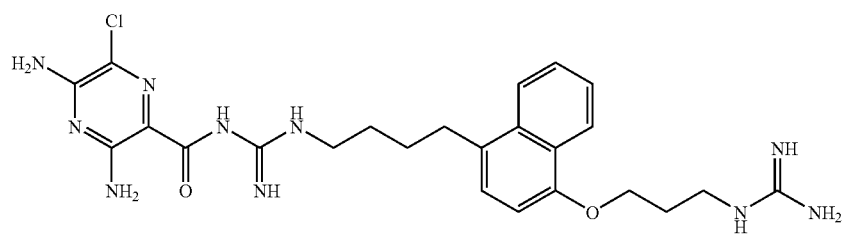
or a pharmaceutically acceptable salt thereof.

37. The compound of claim 1, which is represented by the formula:

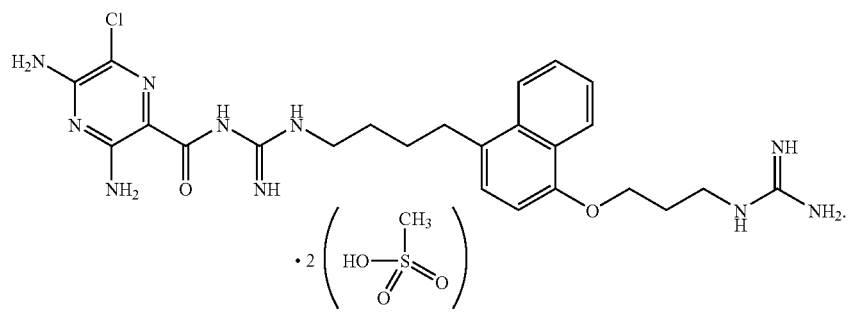

38. A method of promoting hydration of mucosal surfaces, comprising:

administering an effective amount of the compound of claim 1 or a pharmaceutically acceptable salt thereof to a mucosal surface of a subject.

39. A method of blocking sodium channels, comprising:
contacting sodium channels with an effective amount of the compound of claim 1 or a pharmaceutically acceptable salt thereof.

* * * * *